US011413344B2

(12) United States Patent
Cooper et al.

(10) Patent No.: US 11,413,344 B2
(45) Date of Patent: Aug. 16, 2022

(54) IMMUNOGENIC COMPOSITIONS FOR USE IN PNEUMOCOCCAL VACCINES

(71) Applicant: Pfizer Inc., New York, NY (US)

(72) Inventors: David Cooper, Monroe, NY (US); Kathrin Ute Jansen, New York, NY (US); Michael William Pride, Staten Island, NY (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/478,265

(22) PCT Filed: Jan. 5, 2018

(86) PCT No.: PCT/IB2018/050084
§ 371 (c)(1),
(2) Date: Jul. 16, 2019

(87) PCT Pub. No.: WO2018/134693
PCT Pub. Date: Jul. 26, 2018

(65) Prior Publication Data
US 2019/0343946 A1    Nov. 14, 2019

Related U.S. Application Data

(60) Provisional application No. 62/448,485, filed on Jan. 20, 2017.

(51) Int. Cl.
*A61K 39/00* (2006.01)
*A61K 39/09* (2006.01)
*A61K 39/39* (2006.01)

(52) U.S. Cl.
CPC ............ *A61K 39/092* (2013.01); *A61K 39/39* (2013.01); *A61K 2039/55505* (2013.01); *A61K 2039/6037* (2013.01); *A61K 2039/70* (2013.01)

(58) Field of Classification Search
CPC .................................................. A61K 39/092
See application file for complete search history.

(56) References Cited

U.S. PATENT DOCUMENTS

| 4,709,017 | A | 11/1987 | Collier et al. |
| 4,950,740 | A | 8/1990 | Greenfield et al. |
| 5,614,382 | A | 3/1997 | Metcalf |
| 5,843,711 | A | 12/1998 | Collier et al. |
| 5,917,017 | A | 6/1999 | Collier et al. |
| 6,194,388 | B1 | 2/2001 | Krieg et al. |
| 6,207,646 | B1 | 3/2001 | Krieg et al. |
| 6,214,806 | B1 | 4/2001 | Krieg et al. |
| 6,218,371 | B1 | 4/2001 | Krieg et al. |
| 6,239,116 | B1 | 5/2001 | Krieg et al. |
| 6,339,068 | B1 | 1/2002 | Krieg et al. |
| 6,455,673 | B1 | 9/2002 | Collier |
| 10,105,412 | B2 | 10/2018 | Gierahn et al. |
| 2006/0228380 | A1 | 10/2006 | Hausdorff et al. |
| 2006/0228381 | A1 | 10/2006 | Bahler et al. |
| 2007/0184071 | A1 | 8/2007 | Hausdorff et al. |
| 2007/0184072 | A1 | 8/2007 | Hausdorff et al. |
| 2007/0231340 | A1 | 10/2007 | Hausdorff et al. |
| 2008/0102498 | A1 | 5/2008 | Bahler et al. |
| 2008/0286838 | A1 | 11/2008 | Yuan et al. |
| 2015/0202309 | A1* | 7/2015 | Emini ............... A61P 31/04 424/450 |
| 2016/0324949 | A1* | 11/2016 | Han ................... A61K 39/092 |
| 2018/0000922 | A1 | 1/2018 | Cooper et al. |

FOREIGN PATENT DOCUMENTS

| CA | 2004810 | 6/1990 |
| CN | 102068690 | 5/2011 |
| CN | 103495161 A | 1/2014 |
| EP | 0378881 B1 | 6/1993 |
| EP | 0427347 B1 | 2/1995 |
| EP | 0471177 B1 | 10/1995 |
| EP | 0594610 B1 | 9/1998 |
| EP | 0735898 B1 | 3/1999 |
| EP | 0761231 B1 | 1/2000 |
| EP | 0689454 B2 | 2/2005 |
| WO | 90/03184 A1 | 4/1990 |
| WO | 91/01146 A1 | 2/1991 |
| WO | 93/15760 A1 | 8/1993 |
| WO | 93/17712 A2 | 9/1993 |
| WO | 94/03208 A1 | 2/1994 |
| WO | 95/08348 A1 | 3/1995 |
| WO | 96/02555 A1 | 2/1996 |
| WO | 96/11711 A1 | 4/1996 |

(Continued)

OTHER PUBLICATIONS

Tanmoy, A.M., et al., "PCR-Based Serotyping of *Steptococcus pneumonieae* from Culture-Negative Specimens Novel Primers for Detection of Serotypes within Serogroup 18", Journal of Clinical Microbiology, 54(8):2178-2181 (2016).

ClinicalTrials.gov, "Study Comparing a 13-valent Pneumococcal Conjugate Vaccine With 23-valent Pneumococcal Polysaccharide Vaccine in Adults", Pfizer, NCT00427895 Study Details. First Posted Jan. 29, 2007. (accessed Sep. 21, 2021).

ClinicalTrials.gov, "Study Evaluating The Safety, Tolerability and Immunogenicity of a 13-Valent Pneumococcal Conjugate Vaccine (13vPnC)", Pfizer, NCT00546572 Study Details. First posted Oct. 19, 2007. (accessed Sep. 21, 2021).

Pride et al, "Validation of an Immunodiagnostic Assay for Detection of 13 *Streptococcus pneumoniae* Serotype-Specific Polysaccharides in Human Urine", Clinical and Vaccine Immunology 19(8):1131-1141 (2012).

(Continued)

*Primary Examiner* — Albert M Navarro
(74) *Attorney, Agent, or Firm* — Carol A. McKeever

(57) ABSTRACT

An object of the present invention is to provide immunogenic compositions for protection against *S. pneumoniae*, in particular against *S. pneumoniae* serogroup 18, while limiting the number of conjugates. The present invention therefore relates to new immunogenic compositions for use in pneumococcal vaccines and to vaccination of human subjects, in particular infants and elderly, against pneumoccocal infections using said immunogenic compositions.

10 Claims, 6 Drawing Sheets

Figure 1:
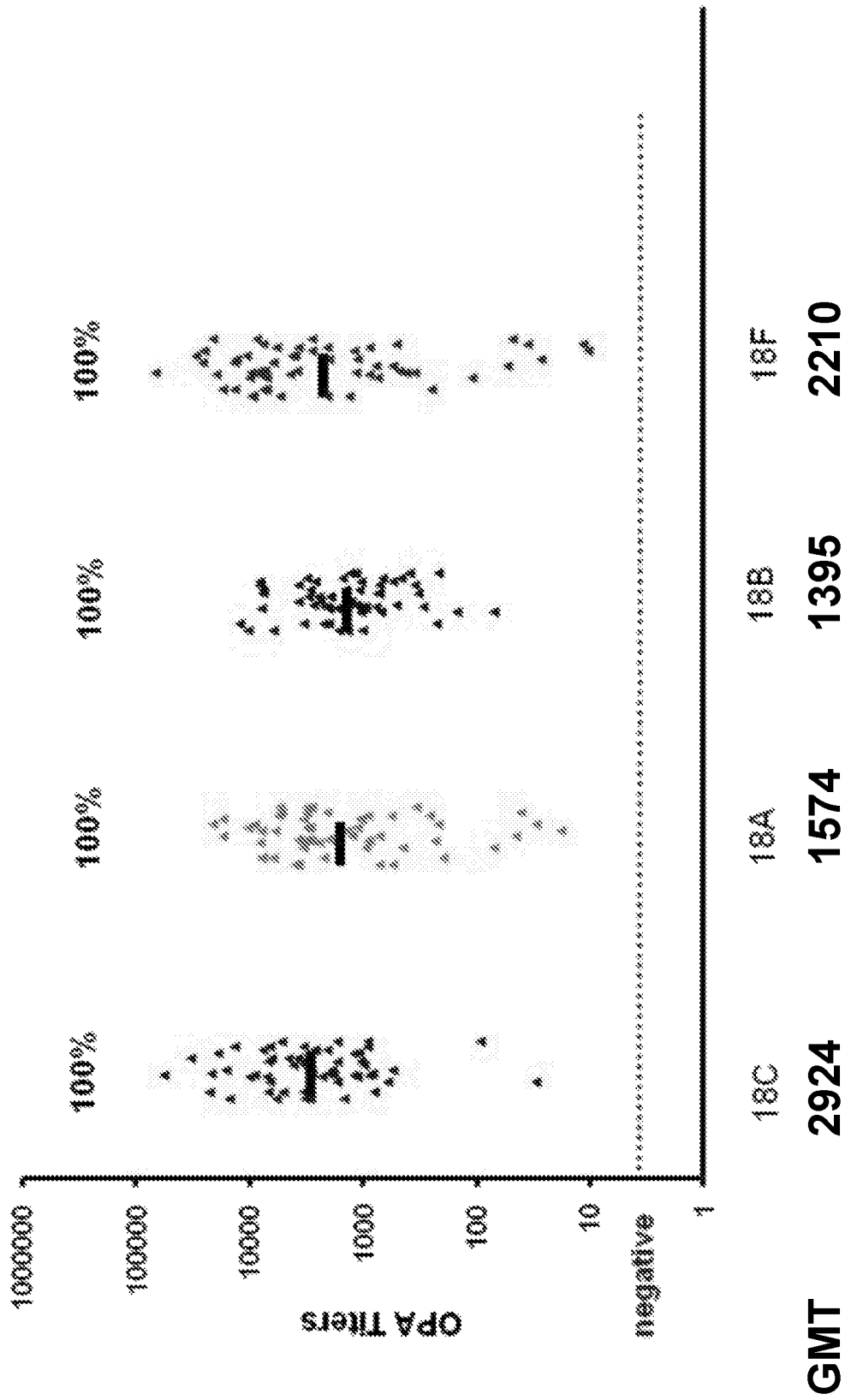

Specification includes a Sequence Listing.

(56) References Cited

FOREIGN PATENT DOCUMENTS

| | | |
|---|---|---|
| WO | 97/01640 A2 | 1/1997 |
| WO | 98/18810 A1 | 5/1998 |
| WO | 98/36772 A1 | 8/1998 |
| WO | 98/42721 A1 | 10/1998 |
| WO | 98/57659 A1 | 12/1998 |
| WO | 98/58668 A2 | 12/1998 |
| WO | 99/11241 A1 | 3/1999 |
| WO | 99/44636 A2 | 9/1999 |
| WO | 99/52549 A1 | 10/1999 |
| WO | 00/07621 A2 | 2/2000 |
| WO | 00/23105 A2 | 4/2000 |
| WO | 00/37105 A2 | 6/2000 |
| WO | 00/39299 A2 | 7/2000 |
| WO | 00/41720 A1 | 7/2000 |
| WO | 00/48630 A1 | 8/2000 |
| WO | 00/56357 A2 | 9/2000 |
| WO | 00/56358 A2 | 9/2000 |
| WO | 00/61761 A2 | 10/2000 |
| WO | 00/62800 A2 | 10/2000 |
| WO | 01/21152 A1 | 3/2001 |
| WO | 01/21207 A2 | 3/2001 |
| WO | 01/72337 A1 | 10/2001 |
| WO | 01/98334 A2 | 12/2001 |
| WO | 02/091998 A2 | 11/2002 |
| WO | 03/024480 A2 | 3/2003 |
| WO | 03/054007 A2 | 7/2003 |
| WO | 2004/081515 A2 | 9/2004 |
| WO | 2004/083251 A2 | 9/2004 |
| WO | 2005/033148 A1 | 4/2005 |
| WO | 2006/032499 A1 | 3/2006 |
| WO | 2006/110352 A2 | 10/2006 |
| WO | 2006/110381 A1 | 10/2006 |
| WO | 2006/134423 A2 | 12/2006 |
| WO | 2007/026190 A2 | 3/2007 |
| WO | 2007/071707 A2 | 6/2007 |
| WO | 2007/116028 A2 | 10/2007 |
| WO | 2008/079653 A1 | 7/2008 |
| WO | 2008/079732 A2 | 7/2008 |
| WO | 2008/118752 A2 | 10/2008 |
| WO | 2008/143709 A2 | 11/2008 |
| WO | 2009/000826 A1 | 12/2008 |
| WO | 2010/109324 A1 | 9/2010 |
| WO | 2010/125480 A1 | 11/2010 |
| WO | 2014/027302 A1 | 2/2014 |
| WO | 2014/097099 A2 | 6/2014 |
| WO | 2016/113644 A1 | 7/2016 |

OTHER PUBLICATIONS

Baraldo et al, "N19 Polyepitope as a Carrier for Enhanced Immunogenicity and Protective Efficacy of Meningococcal Conjugate Vaccines", Infection and Immunity 72(8):4884-4887 (2004).

Bethell et al, "A Novel Method of Activation of Cross-linked Agaroses with 1,1'-Carbonyldiimidazole Which Gives a Matrix for Affinity Chromatography Devoid of Additional Charged Groups", The Journal of Biological Chemistry 254 (8):2572-2574 (1979).

Crooke, et al., "Progress in Antisense Oligonucleotide Therapeutics", Annu. Rev. Pharmacol. Toxicol. 36:107-129 (1996).

Douglas et al, "Exotoxin A of Pseudomonas aeruginosa: Substitution of Glutamic Acid 553 with Aspartic Acid Drastically Reduces Toxicity and Enzymatic Activity", Journal of Bacteriology 169(11):4967-4971 (1987).

Falugi et al, "Rationally designed strings of promiscuous CD4+ T cell epitopes provide help to Haemophilus influenzae type b oligosaccharide: a model for new conjugate vaccines", Eur. J. Immunol. 31:3816-3824 (2001).

Hearn et al, "Application of 1,1'-Carbonyldiimidazole-Activated Matrices for the Purification of Proteins: III. The Use of 1,1'-Carbonyldiimidazole-Activated Agaroses in the Biospecific Affinity Chromatographic Isolation of Serum Antibodies", Journal of Chromatography 218:509-518 (1981).

Hestrin et al, "The Reaction of Acetylcholine and other Carboxylic Acid Derivatives With Hydroxylamine, and Its Analytical Application", J. Biol. Chem. 180:249-261 (1949).

Hsu et al, "Effect of Pneumococcal Conjugate Vaccine on Pneumococcal Meningitidis", The New England Journal of Medicine 360:244-256 (2009).

Hu, et al., "Approach to Validating an Opsonophagocytic Assay for *Streptococcus pneumoniae*", Clin Diagn Lab Immunol 12(2):287-295 (2005).

Hunziker, et al., "Nucleic Acid Analogues: Synthesis and Properties", Mod. Synth. Methods 7:331-417 (1995).

Jones et al, "Use and validation of NMR assays for the identity and O-acetyl content of capsular polysaccharides From Neisseria meningitidis used in vaccine manufacture", Journal of Pharmaceutical and Biomedical Analysis 30 (4):1233-1247 (2002).

Kuo et al, "Characterization of a Recombinant Pneumolysin n and Its Use as a Protein Carrier for Pneumococcal Type 18C Conjugate Vaccines", Infection and Immunity 63(7):2706-2713 (1995).

Lemercinier et al, "Full 1H NMR assignment and detailed O-acetylation patterns of capsular polysaccharides from Neisseria meningitidis used in vaccine production", Carbohydrate Research 296(1-4):83-96 (1996).

Sjölander et al, "ISCOMs: an adjuvant with multiple functions", J Leukoc. Biol. 64:713-723 (1998).

Tanmoy et al, "PCR-Based Serotyping of *Streptococcus pneumoniae* from Culture-Negative Specimens: Novel Primers for Detection of Serotypes within Serogroup 18", Journal of Clinical Microbiology 54(8):2178-2181 (2016).

Uchida et al, "Mutation in the Structural Gene for Diphtheria Toxin Carried by Temperate Phage Beta", Nature New Biology 233:8-11 (1971).

Uchida et al, "Diphtheria Toxin and Related Proteins: I. Isolation and Properties of Mutant Proteins Serologically Related to Diphtheria Toxin", The Journal of Biological Chemistry 248(11):3838-3844 (1973).

Uhlmann et al, "Antisense Oligonucleotides: A New Therapeutic Principle", Chemical Reviews 90(4):543-584 (1990).

* cited by examiner

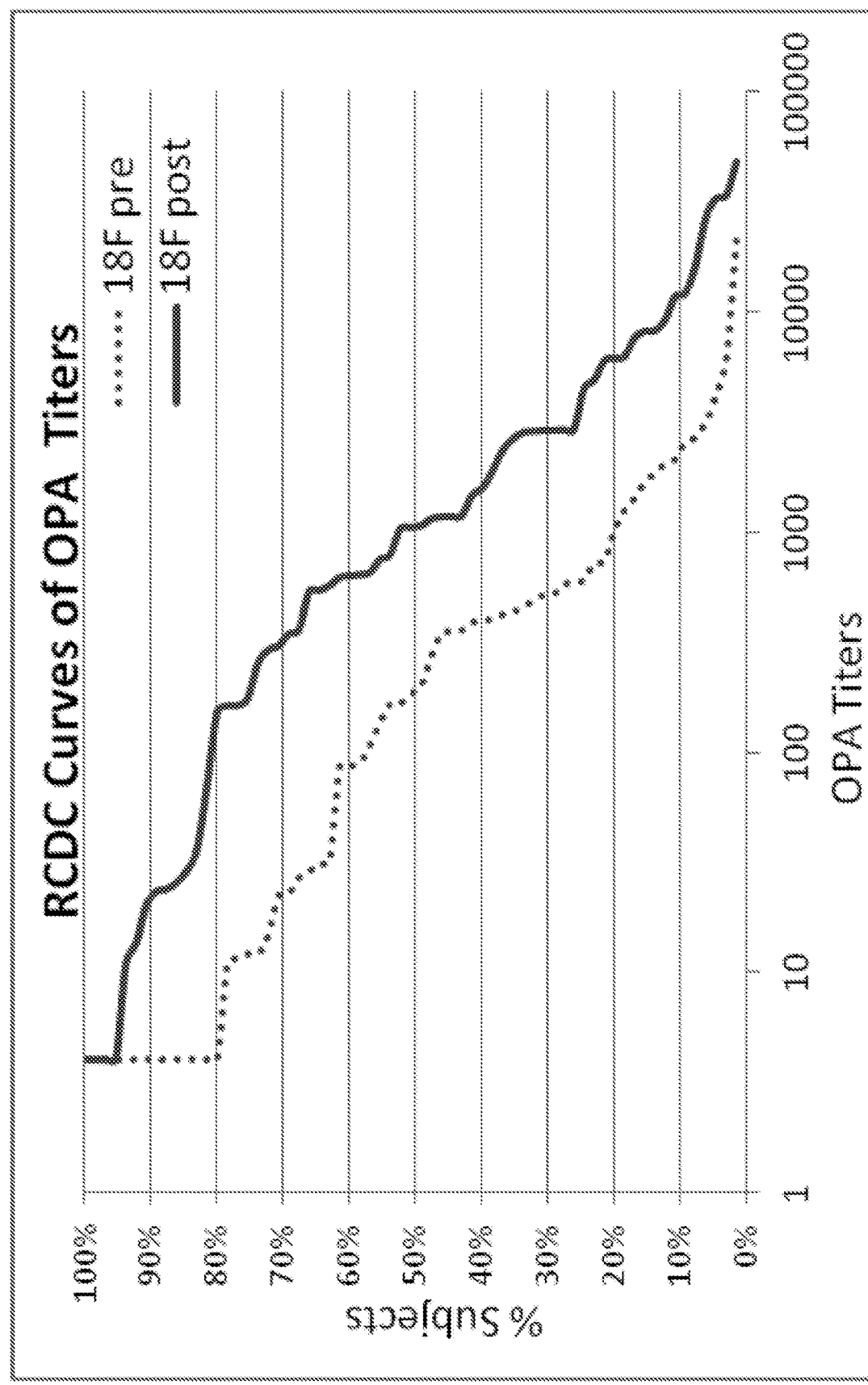

IMMUNOGENIC COMPOSITIONS FOR USE IN PNEUMOCOCCAL VACCINES

This application is the National Stage of International Application No. PCT/IB2018/050084, filed Jan. 5, 2018, which claims the benefit of U.S. Provisional Application No. 62/448,485, filed Jan. 20, 2017, each of which is hereby incorporated by reference in its entirety.

FIELD OF THE INVENTION

An object of the present invention is to provide immunogenic compositions for protection against S. pneumoniae serogroup 18. Immunogenic compositions of the present invention will typically comprise conjugated capsular saccharide antigens (glycoconjugates), wherein the saccharides are derived from serotypes of Streptococcus pneumoniae. The present invention relates to new immunogenic compositions for use in pneumococcal vaccines.

BACKGROUND OF THE INVENTION

Infections caused by pneumococci are a major cause of morbidity and mortality all over the world. Pneumonia, febrile bacteraemia and meningitis are the most common manifestations of invasive pneumococcal disease, whereas bacterial spread within the respiratory tract may result in middle-ear infection, sinusitis or recurrent bronchitis. Compared with invasive disease, the non-invasive manifestations are usually less severe, but considerably more common.

The etiological agent of pneumococcal diseases, Streptococcus pneumoniae (pneumococcus), is a Gram-positive encapsulated coccus, surrounded by a polysaccharide capsule. Differences in the composition of this capsule permit serological differentiation between about 91 capsular types, some of which are frequently associated with pneumococcal disease, others rarely. Invasive pneumococcal infections include pneumonia, meningitis and febrile bacteremia; among the common non-invasive manifestations are otitis media, sinusitis and bronchitis. Pneumococcal conjugate vaccines (PCVs) are pneumococcal vaccines used to protect against disease caused by S. pneumoniae (pneumococcus). There are currently three PCV vaccines available on the global market: PREVNAR® (called Prevenar in some countries) (heptavalent vaccine), SYNFLORIX® (a decavalent vaccine) and PREVNAR 13® (tridecavalent vaccine).

The specific serotypes causing disease beyond the 13 in PREVNAR 13® vary by region, population, and may change over time due to acquisition of antibiotic resistance, pneumococcal vaccine introduction and secular trends of unknown origin.

The addition of conjugates to an immunogenic composition is not a straightforward process as the combination of conjugates into a single multivalent injection may result in competition among the different components and may adversely affect the immunogenicity of any individual conjugate.

This phenomenon of interference may limit the number of conjugates which can be included in a multi-valent vaccine. Therefore protection against a high number of serotypes, while limiting the number of conjugates in the composition, maybe very difficult to obtain despite of the significant value.

An object of the present invention is to provide immunogenic compositions for appropriate protection against S. pneumoniae, in particular against S. pneumoniae serogroup 18, while limiting the number of conjugates.

Streptococcus pneumoniae serogroup 18 consists of four different serotypes, 18F, 18A, 18B, and 18C, each of which produces its own type-specific capsular polysaccharide. It is an object of the present invention to provide immunogenic compositions for appropriate protection against S. pneumoniae serotypes 18F, 18A, 18B, and 18C, with a limited number of conjugates.

SUMMARY OF THE INVENTION

The present invention relates to an immunogenic composition comprising at least one glycoconjugate from S. pneumoniae serotype 18C for use in a method of immunizing a subject against infection by S. pneumoniae serotype 18A, 18B and/or 18F. Preferably said composition does not comprise capsular saccharide from S. pneumoniae serotypes 18A, 18B and 18F.

In one aspect the present invention relates to the use of an immunogenic composition comprising at least one glycoconjugate from S. pneumoniae serotype 18C for the manufacture of a medicament for immunizing a subject against infection by S. pneumoniae serotype 18A, 18B and/or 18F. Preferably said composition does not comprise capsular saccharide from S. pneumoniae serotypes 18A, 18B and/or 18F.

In one aspect, the above immunogenic compositions further comprise at least one glycoconjugate from S. pneumoniae serotypes 4, 6B, 9V, 14, 19F and/or 23F.

In an aspect the above immunogenic compositions further comprise at least one glycoconjugate from S. pneumoniae serotype 1, 5 and/or 7F.

In an aspect the above immunogenic compositions further comprise at least one glycoconjugate from S. pneumoniae serotype 6A and/or 19A.

In an aspect the above immunogenic compositions further comprise at least one glycoconjugate from S. pneumoniae serotype 3, 15B, 22F, 33F, 12F, 10A, 11A and/or 8.

In a further aspect the above immunogenic compositions further comprise at least one glycoconjugate from S. pneumoniae serotype 2, 15C, 17F and/or 20.

In an aspect the above immunogenic compositions further comprise at least one glycoconjugate from S. pneumoniae serotype 9N.

In a further aspect the immunogenic compositions is a 7, 8, 9, 10, 11, 12, 13, 14, 15, 16, 17, 18, 19, 20, 21, 22, 23, 24 or 25-valent pneumococcal conjugate composition.

In a further aspect the glycoconjugates of the immunogenic compositions are individually conjugated to $CRM_{197}$.

In on aspect, the glycoconjugates from S. pneumoniae serotypes 1, 4, 5, 6B, 7F, 9V, 14 and/or 23F of the immunogenic compositions are individually conjugated to PD, and if present, the glycoconjugate from S. pneumoniae serotype 18C is conjugated to TT and the glycoconjugate from S. pneumoniae serotype 19F is conjugated to DT.

In on aspect, the glycoconjugates are prepared using CDAP chemistry or by reductive amination chemistry.

The immunogenic composition may further comprise antigens from other pathogens, and/or at least one adjuvant such as aluminum phosphate, aluminum sulphate or aluminum hydroxide.

In an aspect the immunogenic compositions are able to elicit IgG antibodies in human which are capable of binding S. pneumoniae serotypes 18A, 18B and/or 18F polysaccharide at a concentration of at least 0.35 µg/ml as determined by ELISA assay.

In an aspect the immunogenic compositions are able to elicit a titer of at least 1:8 against S. pneumoniae serotype 18A, 18B and/or 18F in at least 50% of the subjects as determined by in vitro opsonophagocytic killing assay (OPA).

In an aspect the immunogenic compositions are able to significantly increase the proportion of responders against *S. pneumoniae* serotype 18A, 18B and/or 18F as compared to the pre-immunized population.

In an aspect the immunogenic compositions are able to significantly increase the OPA titers of human subjects against *S. pneumoniae* serotype 18A, 18B and/or 18F as compared to the pre-immunized population.

In an aspect the immunogenic compositions are for use in a method of immunizing a subject against infection by *S. pneumoniae* serotype 18A, 18B and/or 18F.

In an aspect the immunogenic compositions are for use in a method for preventing, treating or ameliorating an infection, disease or condition caused by *S. pneumoniae* serotypes 18A, 18B and/or 18F in a subject, for use to prevent serotypes 18A, 18B and/or 18F *S. pneumoniae* infection in a subject or for use in a method to protect or treat a human susceptible to *S. pneumoniae* serotypes 18A, 18B and/or 18F infection, by means of administering said immunogenic compositions via a systemic or mucosal route.

In one aspect the present invention relates to the use of the immunogenic composition disclosed in the present document for the manufacture of a medicament for preventing, treating or ameliorating an infection, disease or condition caused by *S. pneumoniae* serotypes 18A, 18B and/or 18F in a subject, for use to prevent to prevent serotypes 18A, 18B and/or 18F *S. pneumoniae* infection in a subject or for use in a method to protect or treat a human susceptible to *S. pneumoniae* serotypes 18A, 18B and/or 18F infection, by means of administering said immunogenic compositions via a systemic or mucosal route.

In an aspect the invention relates to a method of preventing, treating or ameliorating an infection, disease or condition associated with *S. pneumoniae* serotypes 18A, 18B and/or 18F in a subject, comprising administering to the subject an immunologically effective amount of the immunogenic composition of the invention.

In an aspect the invention relates to a method of preventing an infection by *S. pneumoniae* serotypes 18A, 18B and/or 18F in a subject, comprising administering to the subject an immunologically effective amount of the immunogenic composition of the invention.

The invention further relates to a kit comprising an immunogenic composition disclosed herein and an information leaflet, wherein said information leaflet mentions the ability of the composition to elicit functional antibodies against *S. pneumoniae* serotypes 18A, 18B and/or 18F and process for producing said kit.

It has been surprisingly found that serotype 18C polysaccharide conjugate beyond eliciting functional reactive antibodies to serogroup 18C, can additionnaly elicit functional, cross-reactive antibodies to the other serotypes within the serogroup 18: 18A, 18B and/or 18F.

FIGURES

FIG. 1 Cross-Functional OPA Responses. A subset of 59 sera from adults vaccinated with a 13 valent Pneumococcal Conjugate Vaccine (US Study 6115A1-004; ClinicalTrials.gov Identifier: NCT00427895) was assessed in OPAs for the presence of functional antibodies against serotypes 18C, 18F, 18A, 18B. The percent of samples with OPA positive titer (i.e., ≥1:8) is indicated above each group. Geometric mean titers (GMT) are listed in the x axis below each group.

Figure 2:
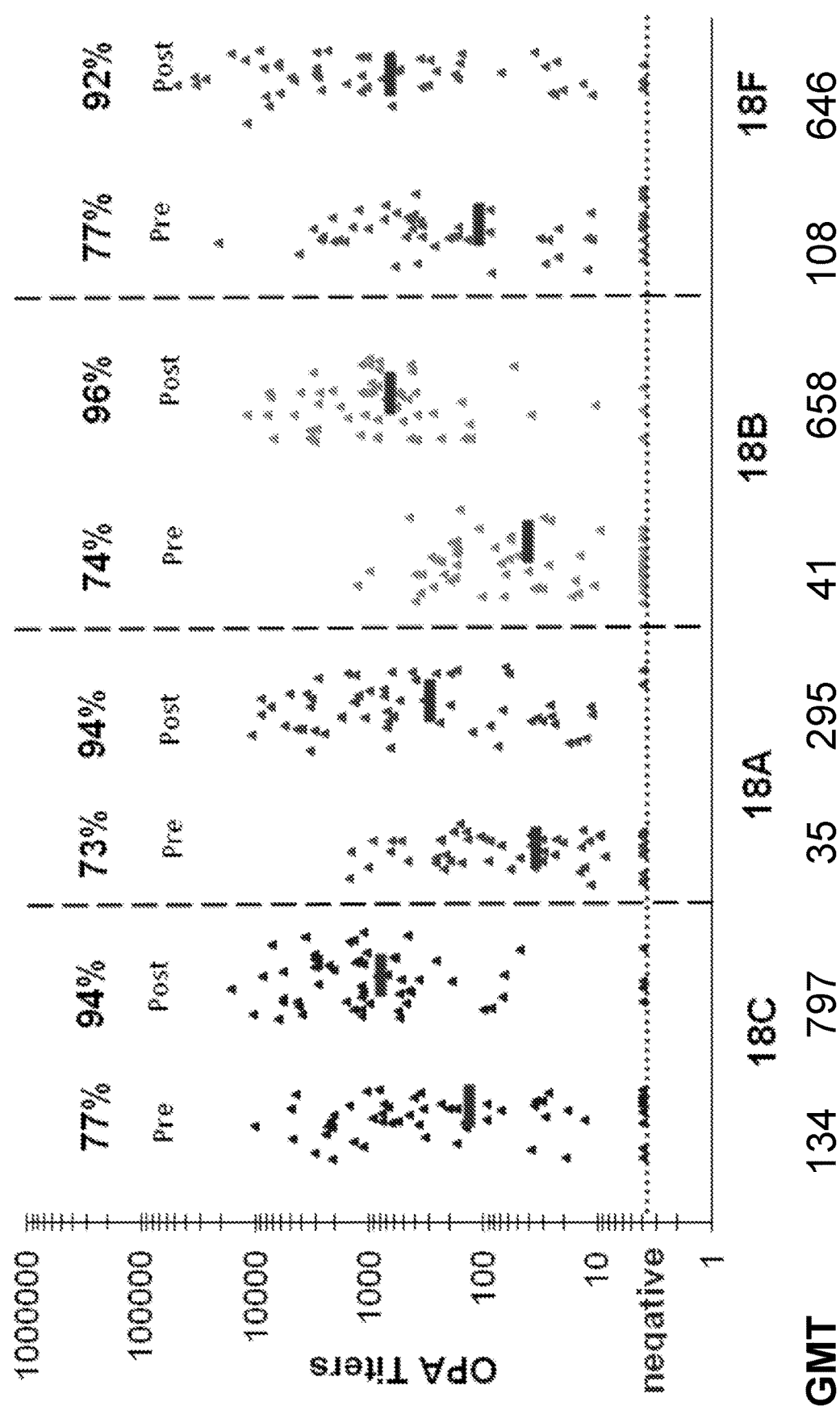

FIG. 2 Cross-Functional OPA Responses of 66 Matched pre/post Sera. A subset of 66 matched pre- and post-vaccinated serum panel from adults vaccinated with a 13 valent Pneumococcal Conjugate Vaccine (study 6115A1-3005; ClinicalTrials.gov Identifier: NCT00546572) were assessed in OPAs for the presence of functional antibodies against serotypes 18C, 18F, 18A, and 18B. The percent of samples with OPA positive titer (i.e., ≥1:8) is indicated above each group. Geometric mean titers (GMT) are listed in the x axis below each group.

Figure 3:
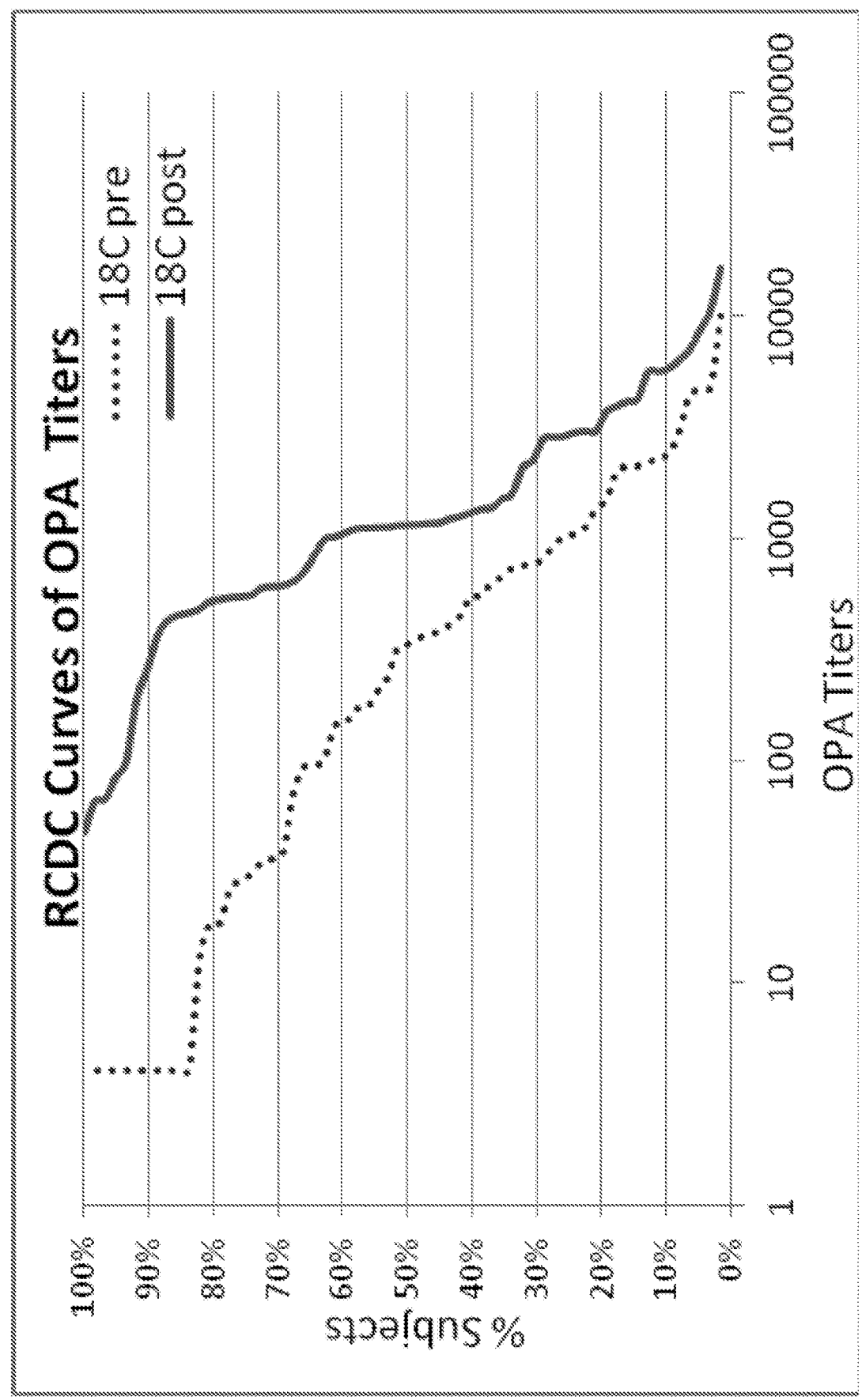

FIG. 3 Reverse cumulative distribution curves (RCDC) of pre and post Immunization—pneumococcal serotype 18C.

Reverse cumulative distribution curves of OPA titers to serotype 18C from a matched pre- and post-vaccination serum panel (N=66) vaccinated with a 13 valent Pneumococcal Conjugate Vaccine (study 6115A1-3005; ClinicalTrials.gov Identifier: NCT00546572). The plots represent the percent of sera with OPA positive titer (i.e., ≥1:8).

Figure 4:
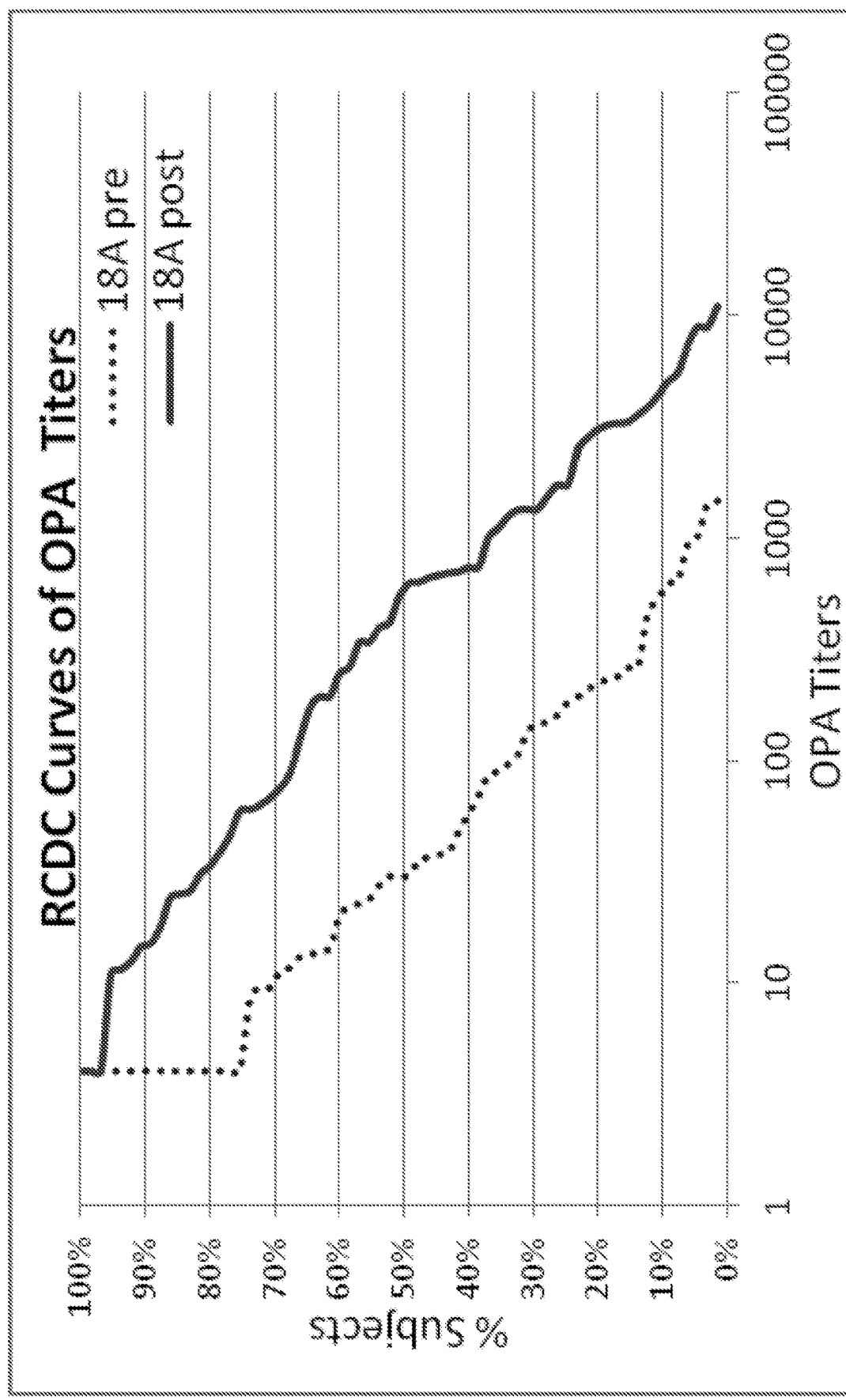

FIG. 4 Reverse cumulative distribution curves (RCDC) of pre and post Immunization—pneumococcal serotype 18A.

Reverse cumulative distribution curves of OPA titers to serotype 18A from a matched pre- and post-vaccination serum panel (N=66) vaccinated with a 13 valent Pneumococcal Conjugate Vaccine (study 6115A1-3005; ClinicalTrials.gov Identifier: NCT00546572). The plots represent the percent of sera with OPA positive titer (i.e., ≥1:8).

Figure 5:
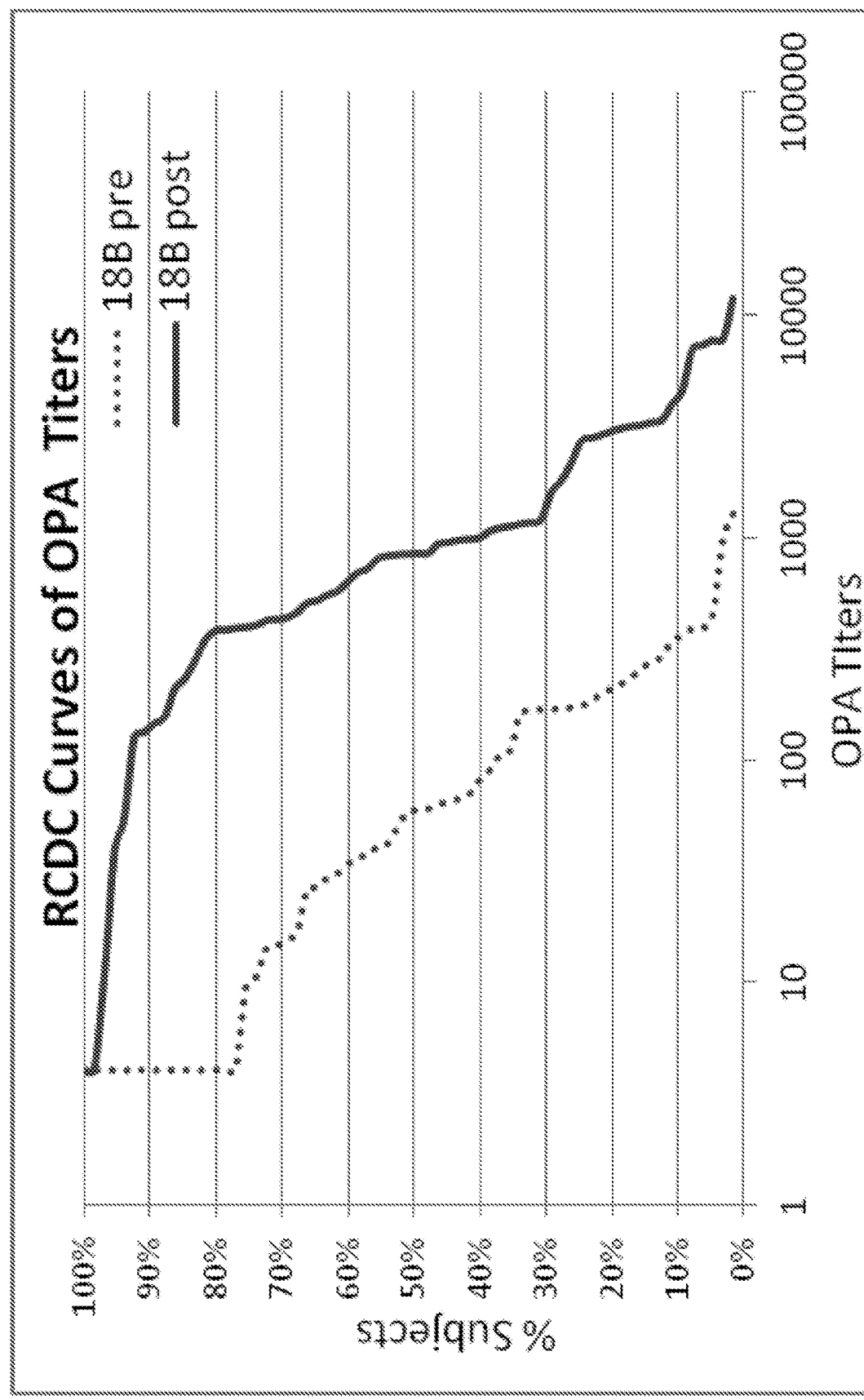

FIG. 5 Reverse cumulative distribution curves (RCDC) of pre and post Immunization—pneumococcal serotype 18B.

Reverse cumulative distribution curves of OPA titers to serotype 18B from a matched pre- and post-vaccination serum panel (N=66) vaccinated with a 13 valent Pneumococcal Conjugate Vaccine (study 6115A1-3005; ClinicalTrials.gov Identifier: NCT00546572). The plots represent the percent of sera with OPA positive titer (i.e., ≥1:8).

FIG. 6 Reverse cumulative distribution curves (RCDC) of pre and post Immunization—pneumococcal serotype 18F.

Reverse cumulative distribution curves of OPA titers to serotype 18F from a matched pre- and post-vaccination serum panel (N=66) vaccinated with a 13 valent Pneumococcal Conjugate Vaccine (study 6115A1-3005; ClinicalTrials.gov Identifier: NCT00546572). The plots represent the percent of sera with OPA positive titer (i.e., ≥1:8).

1 IMMUNOGENIC COMPOSITIONS OF THE INVENTION

Immunogenic compositions of the present invention will typically comprise conjugated capsular saccharide antigens (also named glycoconjugates), wherein the saccharides are derived from serotypes of *S. pneumoniae*.

Preferably, the number of *S. pneumoniae* capsular saccharides can range from 1 serotype (or "v", valences) to 25 different serotypes (25 v). In one embodiment there is one serotype. In one embodiment there are 2 different serotypes. In one embodiment there are 3 different serotypes. In one embodiment there are 4 different serotypes. In one embodiment there are 5 different serotypes. In one embodiment there are 6 different serotypes. In one embodiment there are 7 different serotypes. In one embodiment there are 8 different serotypes. In one embodiment there are 9 different serotypes. In one embodiment there are 10 different serotypes. In one embodiment there are 11 different serotypes. In one embodiment there are 12 different serotypes. In one embodiment there are 13 different serotypes. In one embodiment there are 14 different serotypes. In one embodiment there are 15 different serotypes. In one embodiment there are 16 different serotypes. In an embodiment there are 17 different serotypes. In an embodiment there are 18 different serotypes. In an embodiment there are 19 different serotypes. In an embodiment there are 20 different serotypes. In an embodiment there are 21 different serotypes. In an embodiment there are 22 different serotypes. In an embodiment there are 23 different serotypes. In an embodiment there are 24 different serotypes. In an embodiment there are 25 different serotypes. The capsular saccharides are conjugated to a carrier protein to form glycoconjugates as described here below.

If the protein carrier is the same for 2 or more saccharides in the composition, the saccharides could be conjugated to the same molecule of the protein carrier (carrier molecules having 2 or more different saccharides conjugated to it) [see for instance WO 2004/083251].

In a preferred embodiment though, the saccharides are each individually conjugated to different molecules of the protein carrier (each molecule of protein carrier only having one type of saccharide conjugated to it). In said embodiment, the capsular saccharides are said to be individually conjugated to the carrier protein.

For the purposes of the invention the term 'glycoconjugate' indicates a capsular saccharide linked covalently to a carrier protein. In one embodiment a capsular saccharide is linked directly to a carrier protein. In a second embodiment a bacterial saccharide is linked to a protein through a spacer/linker.

1.1 Carrier Protein of the Invention

A component of the glycoconjugate of the invention is a carrier protein to which the saccharide is conjugated. The terms "protein carrier" or "carrier protein" or "carrier" may be used interchangeably herein. Carrier proteins should be amenable to standard conjugation procedures.

In a preferred embodiment, the carrier protein of the glycoconjugates is selected in the group consisting of: DT (Diphtheria toxin), TT (tetanus toxid) or fragment C of TT, $CRM_{197}$ (a nontoxic but antigenically identical variant of diphtheria toxin), the A chain of diphtheria toxin mutant $CRM_{197}$ (CN103495161), other DT mutants (such as CRM176, CRM228, CRM45 (Uchida et al. (1973) J. Biol. Chem. 218:3838-3844), CRM9, CRM102, CRM103 or CRM107; and other mutations described by Nicholls and Youle in Genetically Engineered Toxins, Ed: Frankel, Maecel Dekker Inc. (1992); deletion or mutation of Glu-148 to Asp, Gln or Ser and/or Ala 158 to Gly and other mutations disclosed in U.S. Pat. Nos. 4,709,017 and 4,950,740; mutation of at least one or more residues Lys 516, Lys 526, Phe 530 and/or Lys 534 and other mutations disclosed in U.S. Pat. Nos. 5,917,017 and 6,455,673; or fragment disclosed in U.S. Pat. No. 5,843,711, pneumococcal pneumolysin (ply) (Kuo et al. (1995) Infect Immun 63:2706-2713) including ply detoxified in some fashion, for example dPLY-GMBS (WO 2004/081515 and WO 2006/032499) or dPLY-formol, PhtX, including PhtA, PhtB, PhtD, PhtE (sequences of PhtA, PhtB, PhtD or PhtE are disclosed in WO 00/37105 and WO 00/39299) and fusions of Pht proteins for example PhtDE fusions, PhtBE fusions, Pht A-E (WO 01/98334, WO 03/054007, WO 2009/000826), OMPC (meningococcal outer membrane protein—usually extracted from *Neisseria meningitidis* serogroup B (EP0372501), PorB (from *N. meningitidis*), PD (*Haemophilus influenzae* protein D; see, e.g., EP0594610 B), or immunologically functional equivalents thereof, synthetic peptides (EP0378881, EP0427347), heat shock proteins (WO 93/17712, WO 94/03208), pertussis proteins (WO 98/58668, EP0471177), cytokines, lymphokines, growth factors or hormones (WO 91/01146), artificial proteins comprising multiple human CD4+ T cell epitopes from various pathogen derived antigens (Falugi et al. (2001) Eur J Immunol 31:3816-3824) such as N19 protein (Baraldoi et al. (2004) Infect Immun 72:4884-4887) pneumococcal surface protein PspA (WO 02/091998), iron uptake proteins (WO 01/72337), toxin A or B of *Clostridium difficile* (WO 00/61761), transferrin binding proteins, pneumococcal adhesion protein (PsaA), recombinant *Pseudomonas aeruginosa* exotoxin A (in particular non-toxic mutants thereof (such as exotoxin A bearing a substitution at glutamic acid 553 (Douglas et al. (1987) J. Bacteriol. 169(11): 4967-4971)). Other proteins, such as ovalbumin, keyhole limpet hemocyanin (KLH), bovine serum albumin (BSA) or purified protein derivative of tuberculin (PPD) also can be used as carrier proteins. Other suitable carrier proteins include inactivated bacterial toxins such as cholera toxoid (e.g., as described in WO 2004/083251), *Escherichia coli* LT, *E. coli* ST, and exotoxin A from *P. aeruginosa*.

In a preferred embodiment, the carrier protein of the glycoconjugates is independently selected from the group consisting of TT, DT, DT mutants (such as $CRM_{197}$), *H. influenzae* protein D, PhtX, PhtD, PhtDE fusions (particularly those described in WO 01/98334 and WO 03/054007), detoxified pneumolysin, PorB, N19 protein, PspA, OMPC, toxin A or B of *C. difficile* and PsaA.

In an embodiment, the carrier protein of the glycoconjugates of the invention is DT (Diphtheria toxoid). In another embodiment, the carrier protein of the glycoconjugates of the invention is TT (tetanus toxid).

In another embodiment, the carrier protein of the glycoconjugates of the invention is PD (*H. influenzae* protein D; see, e.g., EP0594610 B).

The $CRM_{197}$ protein is a nontoxic form of diphtheria toxin but is immunologically indistinguishable from the diphtheria toxin. $CRM_{197}$ is produced by *Corynebacterium diphtheriae* infected by the nontoxigenic phage $\beta197^{tox-}$ created by nitrosoguanidine mutagenesis of the toxigenic corynephage beta (Uchida et al. (1971) Nature New Biology 233:8-11). The $CRM_{197}$ protein has the same molecular weight as the diphtheria toxin but differs therefrom by a single base change (guanine to adenine) in the structural gene. This single base change causes an amino acid substitution (glutamic acid for glycine) in the mature protein and eliminates the toxic properties of diphtheria toxin. The $CRM_{197}$ protein is a safe and effective T-cell dependent carrier for saccharides. Further details about $CRM_{197}$ and production thereof can be found, e.g., in U.S. Pat. No. 5,614,382. In an embodiment, the capsular saccharides of the invention are conjugated to $CRM_{197}$ protein or the A chain of $CRM_{197}$ (see CN103495161). In an embodiment, the capsular saccharides of the invention are conjugated the A chain of $CRM_{197}$ obtained via expression by genetically recombinant *E. coli* (see CN103495161). In an embodiment, the capsular saccharides of the invention are all conjugated to $CRM_{197}$. In an embodiment, the capsular saccharides of the invention are all conjugated to the A chain of $CRM_{197}$.

Accordingly, in frequent embodiments, the glycoconjugates of the invention comprise $CRM_{197}$ as the carrier protein, wherein the capsular polysaccharide is covalently linked to $CRM_{197}$.

1.2 Capsular Saccharide of the Invention

The term "saccharide" throughout this specification may indicate polysaccharide or oligosaccharide and includes both. In frequent embodiments, the saccharide is a polysaccharide, in particular a *S. pneumoniae* capsular polysaccharide. Capsular polysaccharides are prepared by standard techniques known to those of ordinary skill in the art.

In the present invention, capsular polysaccharides may be prepared, e.g., from serotypes 1, 2, 3, 4, 5, 6A, 6B, 7F, 8, 9V, 9N, 10A, 11A, 12F, 14, 15B, 15C, 17F, 18C, 19A, 19F, 20, 22F, 23F and 33F of *S. pneumoniae*. Typically capsular polysaccharides are produced by growing each *S. pneumoniae* serotype in a medium (e.g., in a soy-based medium), the polysaccharides are then prepared from the bacteria culture. Bacterial strains of *S. pneumoniae* used to make the respective polysaccharides that are used in the glycoconjugates of the invention may be obtained from established culture collections or clinical specimens.

The population of the organism (each *S. pneumoniae* serotype) is often scaled up from a seed vial to seed bottles and passaged through one or more seed fermentors of increasing volume until production scale fermentation volumes are reached. At the end of the growth cycle the cells are lysed and the lysate broth is then harvested for downstream (purification) processing (see for example WO 2006/110381, WO 2008/118752, and U.S. Patent App. Pub. Nos. 2006/0228380, 2006/0228381, 2008/0102498 and 2008/0286838).

The individual polysaccharides are typically purified through centrifugation, precipitation, ultra-filtration, and/or column chromatography (see for example WO 2006/110352 and WO 2008/118752).

Purified polysaccharides may be activated (e.g., chemically activated) to make them capable of reacting (e.g., either directly to the carrier protein of via a linker such as an eTEC spacer) and then incorporated into glycoconjugates of the invention, as further described herein.

*S. pneumoniae* capsular polysaccharides comprise repeating oligosaccharide units which may contain up to 8 sugar residues.

In an embodiment, capsular saccharide of the invention may be one oligosaccharide unit, or a shorter than native length saccharide chain of repeating oligosaccharide units.

In an embodiment, capsular saccharide of the invention is one repeating oligosaccharide unit of the relevant serotype.

In an embodiment, capsular saccharide of the invention may be oligosaccharides. Oligosaccharides have a low number of repeat units (typically 5-15 repeat units) and are typically derived synthetically or by hydrolysis of polysaccharides.

In an embodiment, all of the capsular saccharides of the present invention and in the immunogenic compositions of the present invention are polysaccharides. High molecular weight capsular polysaccharides are able to induce certain antibody immune responses due to the epitopes present on the antigenic surface. The isolation and purification of high molecular weight capsular polysaccharides is preferably contemplated for use in the conjugates, compositions and methods of the present invention.

In some embodiments, the purified polysaccharides before conjugation have a molecular weight of between 5 kDa and 4,000 kDa. In other such embodiments, the polysaccharide has a molecular weight of between 10 kDa and 4,000 kDa; between 50 kDa and 4,000 kDa; between 50 kDa and 3,000 kDa; between 50 kDa and 2,000 kDa; between 50 kDa and 1,500 kDa; between 50 kDa and 1,000 kDa; between 50 kDa and 750 kDa; between 50 kDa and 500 kDa; between 100 kDa and 4,000 kDa; between 100 kDa and 3,000 kDa; 100 kDa and 2,000 kDa; between 100 kDa and 1,500 kDa; between 100 kDa and 1,000 kDa; between 100 kDa and 750 kDa; between 100 kDa and 500 kDa; between 100 and 400 kDa; between 200 kDa and 4,000 kDa; between 200 kDa and 3,000 kDa; between 200 kDa and 2,000 kDa; between 200 kDa and 1,500 kDa; between 200 kDa and 1,000 kDa; or between 200 kDa and 500 kDa.

In further embodiments, the capsular polysaccharide has a molecular weight of between 70 kDa to 150 kDa; 80 kDa to 160 kDa; 90 kDa to 250 kDa; 100 kDa to 1,000; 100 kDa to 500 kDa; 100 kDa to 400 kDa; 100 kDa to 160 kDa; 150 kDa to 600 kDa; 200 kDa to 1,000 kDa; 200 kDa to 600 kDa; 200 kDa to 400 kDa; 300 kDa to 1,000 KDa; 300 kDa to 600 kDa; 300 kDa to 500 kDa or 500 kDa to 600 kDa.

In further embodiments, the capsular polysaccharide has a molecular weight of between 5 kDa to 100 kDa; 7 kDa to 100 kDa; 10 kDa to 100 kDa; 20 kDa to 100 kDa; 30 kDa to 100 kDa; 40 kDa to 100 kDa; 50 kDa to 100 kDa; 60 kDa to 100 kDa; 70 kDa to 100 kDa; 80 kDa to 100 kDa; 90 kDa to 100 kDa; 5 kDa to 90 KDa; 5 kDa to 80 kDa; 5 kDa to 70 kDa; 5 kDa to 60 kDa; 5 kDa to 50 kDa; 5 kDa to 40 kDa; 5 kDa to 30 kDa; 5 kDa to 20 kDa or 5 kDa to 10 kDa. Any whole number integer within any of the above ranges is contemplated as an embodiment of the disclosure.

A polysaccharide can become slightly reduced in size during normal purification procedures. Additionally, as described herein, polysaccharide can be subjected to sizing techniques before conjugation. Mechanical or chemical sizing maybe employed. Chemical hydrolysis maybe conducted using acetic acid. For example, saccharides of serotype 18C can be sized (and de-O-acetylated) by acetic acid treatment (see e.g. WO2006/110381, page 37 lines 1-4). Mechanical sizing maybe conducted using High Pressure Homogenization Shearing. The molecular weight ranges mentioned above refer to purified polysaccharides before conjugation (e.g., before activation).

In a preferred embodiment the purified polysaccharides, are capsular polysaccharide from serotypes 1, 2, 3, 4, 5, 6A, 6B, 7F, 8, 9V, 9N, 10A, 11A, 12F, 14, 15B, 15C, 17F, 18C, 19A, 19F, 20, 22F, 23F or 33F of *S. pneumoniae*, wherein the capsular polysaccharide has a molecular weight falling within one of the molecular weight ranges as described here above.

As used herein, the term "molecular weight" of polysaccharide or of carrier protein-polysaccharide conjugate refers to molecular weight calculated by size exclusion chromatography (SEC) combined with multiangle laser light scattering detector (MALLS).

In some embodiments, the pneumococcal saccharides from serotypes 9V, 18C, 11A, 15B, 22F and/or 33F of the invention are O-acetylated. In some embodiments, the pneumococcal saccharides from serotypes 9V, 11A, 15B, 22F and/or 33F of the invention are O-acetylated. In a preferred embodiment, the pneumococcal saccharide from serotype 18C of the invention is de-O-acetylated. For example, saccharides of serotype 18C can be de-O-acetylated by acidic treatment (see e.g. WO2006/110381, page 37 lines 1-4).

The degree of O-acetylation of the polysaccharide can be determined by any method known in the art, for example, by proton NMR (see for example Lemercinier et al. (1996) Carbohydrate Research 296:83-96, Jones et al. (2002) J. Pharmaceutical and Biomedical Analysis 30:1233-1247, WO 2005/033148 and WO 00/56357). Another commonly used method is described in Hestrin (1949) J. Biol. Chem. 180:249-261. Preferably, the presence of O-acetyl groups is determined by ion-HPLC analysis. The purified polysaccharides described herein are chemically activated to make the saccharides capable of reacting with the carrier protein.

These pneumococcal conjugates are prepared by separate processes and formulated into a single dosage formulation as described below.

1.3 Glycoconjugates of the Invention

The purified saccharides are chemically activated to make the saccharides (i.e., activated saccharides) capable of reacting with the carrier protein, either directly or via a linker. Once activated, each capsular saccharide is separately conjugated to a carrier protein to form a glycoconjugate. In one embodiment, each capsular saccharide is conjugated to the same carrier protein. The chemical activation of the saccharides and subsequent conjugation to the carrier protein can be achieved by the activation and conjugation methods disclosed herein.

1.3.1 Glycoconjugates of the Invention

Capsular polysaccharides from serotypes 1, 2, 3, 4, 5, 6A, 6B, 7F, 8, 9V, 9N, 10A, 11A, 12F, 14, 15B, 15C, 17F, 18C, 19A, 19F, 20, 22F, 23F and/or 33F of S. pneumoniae are prepared as disclosed above.

In an embodiment, the polysaccharides are activated with 1-cyano-4-dimethylamino pyridinium tetrafluoroborate (CDAP) to form a cyanate ester. The activated polysaccharide is then coupled directly or via a spacer (linker) group to an amino group on the carrier protein (preferably $CRM_{197}$). For example, the spacer could be cystamine or cysteamine to give a thiolated polysaccharide which could be coupled to the carrier via a thioether linkage obtained after reaction with a maleimide-activated carrier protein (for example using N-[γ-maleimidobutyrloxy]succinimide ester (GMBS)) or a haloacetylated carrier protein (for example using iodoacetimide, N-succinimidyl bromoacetate (SBA; SIB), N-succinimidyl(4-iodoacetyl)aminobenzoate (SIAB), sulfo-succinimidyl(4-iodoacetyl)aminobenzoate (sulfo-SIAB), N-succinimidyl iodoacetate (SIA), or succinimidyl 3-[bromoacetamido]proprionate (SBAP)). Preferably, the cyanate ester (optionally made by CDAP chemistry) is coupled with hexane diamine or adipic acid dihydrazide (ADH) and the amino-derivatised saccharide is conjugated to the carrier protein (e.g., $CRM_{197}$) using carbodiimide (e.g., EDAC or EDC) chemistry via a carboxyl group on the protein carrier. Such conjugates are described for example in WO 93/15760, WO 95/08348 and WO 96/129094.

In an embodiment of the present invention, the glycoconjugates from S. pneumoniae serotypes 1, 2, 3, 4, 5, 6A, 6B, 7F, 8, 9V, 9N, 10A, 11A, 12F, 14, 15B, 15C, 17F, 18C, 19A, 19F, 20, 22F, 23F and/or 33F are prepared using CDAP chemistry. In an embodiment of the present invention, the glycoconjugates from S. pneumoniae serotypes 1, 4, 5, 6B, 7F, 9V, 14, 18C, 19F, and 23F are prepared using CDAP chemistry. In an embodiment of the present invention, the glycoconjugates from S. pneumoniae serotypes 1, 4, 5, 6A, 6B, 7F, 9V, 14, 18C, 19F, and 23F are prepared using CDAP chemistry. In an embodiment of the present invention, the glycoconjugates from S. pneumoniae serotypes 1, 4, 5, 6B, 7F, 9V, 14, 18C, 19A, 19F, and 23F are prepared using CDAP chemistry. In an embodiment of the present invention, the glycoconjugates from S. pneumoniae serotypes 1, 4, 5, 6A, 6B, 7F, 9V, 14, 18C, 19A, 19F, and 23F are prepared using CDAP chemistry. In an embodiment of the present invention, the glycoconjugates from S. pneumoniae serotypes 1, 3, 4, 5, 6A, 6B, 7F, 9V, 14, 18C, 19A, 19F, and 23F are prepared using CDAP chemistry.

Other suitable techniques for conjugation use carbodiimides, hydrazides, active esters, norborane, p-nitrobenzoic acid, N-hydroxysuccinimide, S—NHS, EDC, TSTU. Many are described in International Patent Application Publication No. WO 98/42721. Conjugation may involve a carbonyl linker which may be formed by reaction of a free hydroxyl group of the saccharide with CDI (see Bethell et al. (1979) 1. Biol. Chem. 254:2572-2574; Hearn et al. (1981) J. Chromatogr. 218:509-518) followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

In an preferred embodiment, at least one of capsular polysaccharides from serotypes 1, 2, 3, 4, 5, 6A, 6B, 7F, 8, 9V, 9N, 10A, 11A, 12F, 14, 15B, 15C, 17F, 18C, 19A, 19F, 20, 22F, 23F and 33F of S. pneumoniae is conjugated to the carrier protein by reductive amination (such as described in U.S. Patent Appl. Pub. Nos. 2006/0228380, 2007/184072, 2007/0231340 and 2007/0184071, WO 2006/110381, WO 2008/079653, and WO 2008/143709).

In an embodiment of the present invention, the glycoconjugate from S. pneumoniae serotype 18C is prepared by reductive amination. In an embodiment of the present invention, the glycoconjugate from S. pneumoniae serotype 6A is prepared by reductive amination. In an embodiment of the present invention, the glycoconjugate from S. pneumoniae serotype 19A is prepared by reductive amination. In an embodiment of the present invention, the glycoconjugate from S. pneumoniae serotype 3 is prepared by reductive amination. In an embodiment of the present invention, the glycoconjugates from S. pneumoniae serotypes 6A and 19A are prepared by reductive amination. In an embodiment of the present invention, the glycoconjugates from S. pneumoniae serotypes 3, 6A and 19A are prepared by reductive amination.

In a preferred embodiment of the present invention, the glycoconjugates from S. pneumoniae serotypes 4, 6B, 9V, 14, 18C, 19F and 23F are prepared by reductive amination. In an embodiment of the present invention, the glycoconjugates from S. pneumoniae serotypes 1, 4, 6B, 9V, 14, 18C, 19F and 23F are prepared by reductive amination. In an embodiment of the present invention, the glycoconjugates from S. pneumoniae serotypes 1, 4, 5, 6B, 9V, 14, 18C, 19F and 23F are prepared by reductive amination. In an embodiment of the present invention, the glycoconjugates from S. pneumoniae serotypes 1, 4, 5, 6B, 7F, 9V, 14, 18C, 19F and 23F are prepared by reductive amination. In an embodiment of the present invention, the glycoconjugates from S. pneumoniae serotypes 1, 4, 5, 6A, 6B, 7F, 9V, 14, 18C, 19F and 23F are prepared by reductive amination. In an embodiment of the present invention, the glycoconjugates from S. pneumoniae serotypes 1, 4, 5, 6A, 6B, 7F, 9V, 14, 18C, 19A, 19F and 23F are prepared by reductive amination. In an embodiment of the present invention, the glycoconjugates from S. pneumoniae serotypes 1, 3, 4, 5, 6A, 6B, 7F, 9V, 14, 18C, 19A, 19F and 23F are all prepared by reductive amination.

In another preferred embodiment, the glycoconjugates from S. pneumoniae serotypes 1, 3, 4, 5, 6A, 6B, 7F, 9V, 14, 18C, 19A, 19F, 22F and 23F are all prepared by reductive amination.

In another preferred embodiment, the glycoconjugates from S. pneumoniae serotypes 1, 3, 4, 5, 6A, 6B, 7F, 9V, 14, 15B, 18C, 19A, 19F, 22F and 23F are all prepared by reductive amination.

In another preferred embodiment, the glycoconjugates from S. pneumoniae serotypes 1, 3, 4, 5, 6A, 6B, 7F, 8, 9V, 10A, 11A, 12F, 14, 15B, 18C, 19A, 19F, 22F and 23F are all prepared by reductive amination.

In another preferred embodiment, the glycoconjugates from S. pneumoniae serotypes 1, 2, 3, 4, 5, 6A, 6B, 7F, 9V, 14, 18C, 19A, 19F and 23F are all prepared by reductive amination.

In another preferred embodiment, the glycoconjugates from S. pneumoniae serotypes 1, 4, 5, 6A, 6B, 7F, 9V, 12F, 14, 15C, 18C, 19A, 19F, 22F, 23F and 33F are all prepared by reductive amination.

In another preferred embodiment, the glycoconjugates from S. pneumoniae serotypes 1, 3, 4, 5, 6A, 6B, 7F, 8, 9V, 10A, 11A, 14, 15B, 18C, 19A, 19F, 22F and 23F are all prepared by reductive amination.

In another preferred embodiment, the glycoconjugates from S. pneumoniae serotypes 1, 3, 4, 5, 6A, 6B, 7F, 8, 9V, 10A, 11A, 12F, 14, 15B, 18C, 19A, 19F, 22F and 23F are all prepared by reductive amination.

In another preferred embodiment, the glycoconjugates from S. pneumoniae serotypes 1, 3, 4, 5, 6A, 6B, 7F, 8, 9V, 10A, 11A, 12F, 14, 15B, 18C, 19A, 19F, 22F, 23F and 33F are all prepared by reductive amination.

In another preferred embodiment, the glycoconjugates from S. pneumoniae serotypes 1, 2, 3, 4, 5, 6A, 6B, 7F, 8, 9V, 10A, 11A, 12F, 14, 15B, 15C, 17F, 18C, 19A, 19F, 20, 22F, 23F and 33F are all prepared by reductive amination.

In another preferred embodiment, the glycoconjugates from S. pneumoniae serotypes 1, 2, 3, 4, 5, 6A, 6B, 7F, 8, 9V, 9N, 10A, 11A, 12F, 14, 15B, 15C, 17F, 18C, 19A, 19F, 20, 22F, 23F and 33F are all prepared by reductive amination.

Reductive amination involves two steps, (1) oxidation of the polysaccharide, (2) reduction of the activated polysaccharide and a carrier protein to form a conjugate. Before oxidation, the polysaccharide is optionally hydrolyzed. Mechanical or chemical hydrolysis maybe employed. Chemical hydrolysis maybe conducted using acetic acid.

The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and includes the various salts of periodate (e.g., sodium periodate and potassium periodate). In an embodiment the capsular polysaccharide is oxidized in the presence of metaperiodate, preferably in the presence of sodium periodate ($NaIO_4$). In another embodiment the capsular polysaccharide is oxydized in the presence of orthoperiodate, preferably in the presence of periodic acid.

In an embodiment, the oxidizing agent is a stable nitroxyl or nitroxide radical compound, such as piperidine-N-oxy or pyrrolidine-N-oxy compounds, in the presence of an oxidant to selectively oxidize primary hydroxyls (as described in WO 2014/097099). In said reaction, the actual oxidant is the N-oxoammonium salt, in a catalytic cycle. In an aspect, said stable nitroxyl or nitroxide radical compound are piperidine-N-oxy or pyrrolidine-N-oxy compounds. In an aspect, said stable nitroxyl or nitroxide radical compound bears a TEMPO (2,2,6,6-tetramethyl-1-piperidinyloxy) or a PROXYL (2,2,5,5-tetramethyl-1-pyrrolidinyloxy) moiety. In an aspect, said stable nitroxyl radical compound is TEMPO or a derivative thereof. In an aspect, said oxidant is a molecule bearing a N-halo moiety. In an aspect, said oxidant is selected from the group consisting of N-Chloro-Succinimide, N-Bromosuccinimide, N-Iodosuccinimide, Dichloroisocyanuric acid, 1,3,5-trichloro-1,3,5-triazinane-2,4,6-trione, Dibromoisocyanuric acid, 1,3,5-tribromo-1,3,5-triazinane-2,4,6-trione, Diiodoisocyanuric acid and 1,3,5-triiodo-1,3,5-triazinane-2,4,6-trione. Preferably said oxidant is N-Chlorosuccinimide.

In a preferred embodiment, capsular polysaccharides from serotypes 12F S. pneumoniae are conjugated to the carrier protein by reductive amination, wherein the oxidizing agent is 2,2,6,6-Tetramethyl-1-piperidinyloxy (TEMPO) free radical and N-Chlorosuccinimide (NCS) as the cooxidant (as described in WO 2014/097099). Therefore in one aspect, the glycoconjugates from S. pneumoniae serotype 12F are obtainable by a method comprising the steps of: a) reacting a 12F saccharide with 2,2,6,6-tetramethyl-1-piperidinyloxy (TEMPO) and N-chlorosuccinimide (NCS) in an aqueous solvent to produce an activated saccharide; and b) reacting the activated saccharide with a carrier protein comprising one or more amine groups (said method is designated "TEMPO/NCS-reductive amination" thereafter).

Optionally the oxidation reaction is quenched by addition of a quenching agent. The quenching agent maybe selected from vicinal diols, 1,2-aminoalcohols, amino acids, glutathione, sulfite, bisulfate, dithionite, metabisulfite, thiosulfate, phosphites, hypophosphites or phosphorous acid (such as glycerol, ethylene glycol, propan-1,2-diol, butan-1,2-diol or butan-2,3-diol, ascorbic acid).

Following the oxidation step of the polysaccharide, the polysaccharide is said to be activated and is referred to an "activated polysaccharide" here below. The activated polysaccharide and the carrier protein may be lyophilised (freeze-dried), either independently (discrete lyophilization) or together (co-lyophilized). In one embodiment the activated polysaccharide and the carrier protein are co-lyophilized. In another embodiment the activated polysaccharide and the carrier protein are lyophilized independently.

In one embodiment the lyophilization takes place in the presence of a non-reducing sugar, possible non-reducing sugars include sucrose, trehalose, raffinose, stachyose, melezitose, dextran, mannitol, lactitol and palatinit.

The second step of the conjugation process is the reduction of the activated polysaccharide and a carrier protein to form a conjugate (so-called reductive amination), using a reducing agent. Reducing agents which are suitable include the cyanoborohydrides (such as sodium cyanoborohydride, sodium triacetoxyborohydride or sodium or zinc borohydride in the presence of Bronsted or Lewis acids), amine boranes such as pyridine borane, 2-Picoline Borane, 2,6-diborane-methanol, dimethylamine-borane, t-BuMe$^i$PrN-BH$_3$, benzylamine-BH$_3$ or 5-ethyl-2-methylpyridine borane (PEMB) or borohydride exchange resin. In one embodiment the reducing agent is sodium cyanoborohydride.

In an embodiment, the reduction reaction is carried out in aqueous solvent (e.g., selected from PBS, MES, HEPES, Bis-tris, ADA, PIPES, MOPSO, BES, MOPS, DIPSO, MOBS, HEPPSO, POPSO, TEA, EPPS, Bicine or HEPB, at a pH between 6.0 and 8.5, 7.0 and 8.0, or 7.0 and 7.5), in another embodiment the reaction is carried out in aprotic solvent. In an embodiment, the reduction reaction is carried out in DMSO (dimethylsulfoxide) or in DMF (dimethylformamide) solvent. The DMSO or DMF solvent may be used to reconstitute the activated polysaccharide and carrier protein which has been lyophilized.

At the end of the reduction reaction, there may be unreacted aldehyde groups remaining in the conjugates, these may be capped using a suitable capping agent. In one embodiment this capping agent is sodium borohydride (NaBH$_4$). Following the conjugation (the reduction reaction and optionally the capping), the glycoconjugates may be purified (enriched with respect to the amount of polysaccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration. In an embodiment, the glycoconjugates are purified by diafiltration or ion exchange chromatography or size exclusion chromatography.

In one embodiment the glycoconjugates are sterile filtered.

In an embodiment of the present invention, the glycoconjugates from S. pneumoniae serotypes 1, 4, 5, 6B, 7F, 9V, 14, 18C, 19F, and 23F are prepared using CDAP chemistry and the glycoconjugate from S. pneumoniae serotype 6A is prepared by reductive amination.

In an embodiment of the present invention, the glycoconjugates from S. pneumoniae serotypes 1, 4, 5, 6B, 7F, 9V, 14, 18C, 19F, and 23F are prepared using CDAP chemistry and the glycoconjugate from S. pneumoniae serotype 19A is prepared by reductive amination.

In an embodiment of the present invention, the glycoconjugates from S. pneumoniae serotypes 1, 4, 5, 6B, 7F, 9V, 14, 18C, 19F, and 23F are prepared using CDAP chemistry and the glycoconjugates from S. pneumoniae serotype 6A and 19A are prepared by reductive amination.

In an embodiment of the present invention, the glycoconjugates from S. pneumoniae serotypes 1, 4, 5, 6B, 7F, 9V, 14, 18C, 19F, and 23F are prepared using CDAP chemistry and the glycoconjugates from S. pneumoniae serotype 3, 6A and 19A are prepared by reductive amination.

In an embodiment of the present invention, the glycoconjugates from S. pneumoniae serotypes 1, 4, 5, 6B, 7F, 9V, 14, 18C, 19F, 22F and 23F are prepared using CDAP chemistry and the glycoconjugate from S. pneumoniae serotype 6A is prepared by reductive amination.

In an embodiment of the present invention, the glycoconjugates from S. pneumoniae serotypes 1, 4, 5, 6B, 7F, 9V, 14, 18C, 19F, 22F, and 23F are prepared using CDAP chemistry and the glycoconjugate from S. pneumoniae serotype 19A is prepared by reductive amination.

In an embodiment of the present invention, the glycoconjugates from S. pneumoniae serotypes 1, 4, 5, 6B, 7F, 9V, 14, 18C, 19F, 22F, and 23F are prepared using CDAP chemistry and the glycoconjugates from S. pneumoniae serotype 6A and 19A are prepared by reductive amination.

In an embodiment of the present invention, the glycoconjugates from S. pneumoniae serotypes 1, 4, 5, 6B, 7F, 8, 9V, 14, 18C, 19F, 22F and 23F are prepared using CDAP chemistry and the glycoconjugates from S. pneumoniae serotype 3, 6A and 19A are prepared by reductive amination.

In an embodiment, the glycoconjugates of the invention are prepared using the eTEC conjugation, such as described in WO 2014/027302. Said glycoconjugates comprise a saccharide covalently conjugated to a carrier protein through one or more eTEC spacers, wherein the saccharide is covalently conjugated to the eTEC spacer through a carbamate linkage, and wherein the carrier protein is covalently conjugated to the eTEC spacer through an amide linkage. The eTEC linked glycoconjugates of the invention may be represented by the general formula (I):

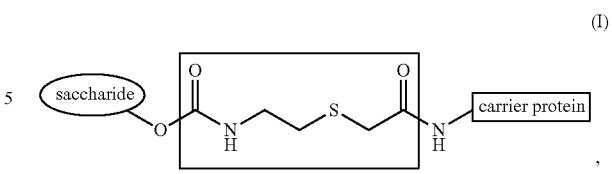

(I)

where the atoms that comprise the eTEC spacer are contained in the central box.

The eTEC spacer includes seven linear atoms (i.e., —C(O)NH(CH$_2$)$_2$SCH$_2$C(O)—) and provides stable thioether and amide bonds between the saccharide and carrier protein. Synthesis of the eTEC linked glycoconjugate involves reaction of an activated hydroxyl group of the saccharide with the amino group of a thioalkylamine reagent, e.g., cystamine or cysteinamine or a salt thereof, forming a carbamate linkage to the saccharide to provide a thiolated saccharide. Generation of one or more free sulfhydryl groups is accomplished by reaction with a reducing agent to provide an activated thiolated saccharide. Reaction of the free sulfhydryl groups of the activated thiolated saccharide with an activated carrier protein having one or more α-haloacetamide groups on amine containing residues generates a thioether bond to form the conjugate, wherein the carrier protein is attached to the eTEC spacer through an amide bond.

In said glycoconjugates of the invention, the saccharide may be a polysaccharide or an oligosaccharide. The carrier protein may be selected from any suitable carrier as described herein or known to those of skill in the art. In frequent embodiments, the saccharide is a polysaccharide. In some such embodiments, the carrier protein is CRM$_{197}$. In some such embodiments, the eTEC linked glycoconjugate comprises a S. pneumoniae serotype 33F capsular polysaccharide.

In particularly preferred embodiments, the eTEC linked glycoconjugate comprises a pneumococcal serotype 33F (Pn33F) capsular polysaccharide, which is covalently conjugated to CRM$_{197}$ through an eTEC spacer (serotype 33F eTEC linked glycoconjugates).

In some embodiments, the glycoconjugate from S. pneumoniae serotypes 1, 7F, 9V and/or 18C of the invention are O-acetylated. In some embodiments, the glycoconjugate from S. pneumoniae serotypes 1, 7F and 9V is O-acetylated and the glycoconjugate from S. pneumoniae serotype 18C is de-O-acetylated.

In some embodiments, the glycoconjugate from S. pneumoniae serotype 1 comprise a saccharide which has a degree of O-acetylation of between 10 and 100%, between 20 and 100%, between 30 and 100%, between 40 and 100%, between 50 and 100%, between 60 and 100%, between 70 and 100%, between 75 and 100%, 80 and 100%, 90 and 100%, 50 and 90%, 60 and 90%, 70 and 90% or 80 and 90%. In other embodiments, the degree of O-acetylation is ≥10%, ≥20%, ≥30%, ≥40%, ≥50%, ≥60%, ≥70%, ≥80%, ≥90%, or about 100%.

In some embodiments, the glycoconjugate from S. pneumoniae serotype 7F comprise a saccharide which has a degree of O-acetylation of between 10 and 100%, between 20 and 100%, between 30 and 100%, between 40 and 100%, between 50 and 100%, between 60 and 100%, between 70 and 100%, between 75 and 100%, 80 and 100%, 90 and 100%, 50 and 90%, 60 and 90%, 70 and 90% or 80 and 90%.

In other embodiments, the degree of O-acetylation is ≥10%, ≥20%, ≥30%, ≥40%, ≥50%, ≥60%, ≥70%, ≥80%, ≥90%, or about 100%.

In some embodiments, the glycoconjugate from *S. pneumoniae* serotype 9V comprise a saccharide which has a degree of O-acetylation of between 10 and 100%, between 20 and 100%, between 30 and 100%, between 40 and 100%, between 50 and 100%, between 60 and 100%, between 70 and 100%, between 75 and 100%, 80 and 100%, 90 and 100%, 50 and 90%, 60 and 90%, 70 and 90% or 80 and 90%. In other embodiments, the degree of O-acetylation is ≥10%, ≥20%, ≥30%, ≥40%, ≥50%, ≥60%, ≥70%, ≥80%, ≥90%, or about 100%.

In some embodiments, the glycoconjugate from *S. pneumoniae* serotype 18C comprise a saccharide which has a degree of O-acetylation of between 10 and 100%, between 20 and 100%, between 30 and 100%, between 40 and 100%, between 50 and 100%, between 60 and 100%, between 70 and 100%, between 75 and 100%, 80 and 100%, 90 and 100%, 50 and 90%, 60 and 90%, 70 and 90% or 80 and 90%. In other embodiments, the degree of O-acetylation is ≥10%, ≥20%, ≥30%, ≥40%, ≥50%, ≥60%, ≥70%, ≥80%, ≥90%, or about 100%. Preferably though, the glycoconjugate from *S. pneumoniae* serotype 18C is de-O-acetylated. In some said embodiments, the glycoconjugate from *S. pneumoniae* serotype 18C comprise a saccharide which has a degree of O-acetylation of between 0 and 50%, between 0 and 40%, between 0 and 30%, between 0 and 20%, between 0 and 10%, between 0 and 5%, or between 0 and 2%. In other embodiments, the degree of O-acetylation is ≤50%, ≤40%, ≤30%, ≤20%, ≤10%, ≤5%, ≤2%, or ≤1%.

By % of O-acetylation it is meant the percentage of a given saccharide relative to 100% (where each repeat unit is fully acetylated relative to its acetylated structure).

In some embodiments, the glycoconjugates of the present invention comprise a saccharide having a molecular weight of between 5 kDa and 2,000 kDa. In other such embodiments, the saccharide has a molecular weight of between 50 kDa and 1,000 kDa. In other such embodiments, the saccharide has a molecular weight of between 70 kDa and 900 kDa. In other such embodiments, the saccharide has a molecular weight of between 100 kDa and 800 kDa. In other such embodiments, the saccharide has a molecular weight of between 200 kDa and 600 kDa. In further such embodiments, the saccharide has a molecular weight of between 100 kDa to 1000 kDa; 100 kDa to 900 kDa; 100 kDa to 800 kDa; 100 kDa to 700 kDa; 100 kDa to 600 kDa; 100 kDa to 500 kDa; 100 kDa to 400 kDa; 100 kDa to 300 kDa; 150 kDa to 1,000 kDa; 150 kDa to 900 kDa; 150 kDa to 800 kDa; 150 kDa to 700 kDa; 150 kDa to 600 kDa; 150 kDa to 500 kDa; 150 kDa to 400 kDa; 150 kDa to 300 kDa; 200 kDa to 1,000 kDa; 200 kDa to 900 kDa; 200 kDa to 800 kDa; 200 kDa to 700 kDa; 200 kDa to 600 kDa; 200 kDa to 500 kDa; 200 kDa to 400 kDa; 200 kDa to 300; 250 kDa to 1,000 kDa; 250 kDa to 900 kDa; 250 kDa to 800 kDa; 250 kDa to 700 kDa; 250 kDa to 600 kDa; 250 kDa to 500 kDa; 250 kDa to 400 kDa; 250 kDa to 350 kDa; 300 kDa to 1,000 kDa; 300 kDa to 900 kDa; 300 kDa to 800 kDa; 300 kDa to 700 kDa; 300 kDa to 600 kDa; 300 kDa to 500 kDa; 300 kDa to 400 kDa; 400 kDa to 1,000 kDa; 400 kDa to 900 kDa; 400 kDa to 800 kDa; 400 kDa to 700 kDa; 400 kDa to 600 kDa; 500 kDa to 600 kDa. In further embodiments, the saccharide has a molecular weight of between 5 kDa to 100 kDa; 7 kDa to 100 kDa; 10 kDa to 100 kDa; 20 kDa to 100 kDa; 30 kDa to 100 kDa; 40 kDa to 100 kDa; 50 kDa to 100 kDa; 60 kDa to 100 kDa; 70 kDa to 100 kDa; 80 kDa to 100 kDa; 90 kDa to 100 kDa; 5 kDa to 90 KDa; 5 kDa to 80 kDa; 5 kDa to 70 kDa; 5 kDa to 60 kDa; 5 kDa to 50 kDa; 5 kDa to 40 kDa; 5 kDa to 30 kDa; 5 kDa to 20 kDa or 5 kDa to 10 kDa. Any whole number integer within any of the above ranges is contemplated as an embodiment of the disclosure. In some such embodiments, the glycoconjugate is prepared using reductive amination.

In some embodiments, the glycoconjugate of the invention has a molecular weight of between 100 kDa and 15,000 kDa; between 500 kDa and 10,000 kDa; between 2,000 kDa and 10,000 kDa; between 3,000 kDa and 8,000 kDa kDa; or between 3,000 kDa and 5,000 kDa. In other embodiments, the glycoconjugate has a molecular weight of between 500 kDa and 10,000 kDa. In other embodiments, glycoconjugate has a molecular weight of between 1,000 kDa and 8,000 kDa. In still other embodiments, the glycoconjugate has a molecular weight of between 2,000 kDa and 8,000 kDa or between 3,000 kDa and 7,000 kDa. In further embodiments, the glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa.

In further embodiments, the glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa.

In further embodiments, the glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

In further embodiments, the glycoconjugate of the invention has a molecular weight of between 100 kDa and 250 kDa; between 100 kDa and 500 kDa; between 100 kDa and 750 kDa; between 100 kDa and 1000 kDa; between 100 kDa and 1500 kDa; between 100 kDa and 2000 kDa; between 100 kDa and 2500 kDa; between 100 kDa and 3000 kDa; between 250 kDa and 500 kDa; between 250 kDa and 1000 kDa; between 250 kDa and 1500 kDa; between 250 kDa and 2000 kDa or between 250 kDa and 2500 kDa.

The molecular weight of the glycoconjugate is measured by SEC-MALLS. Any whole number integer within any of the above ranges is contemplated as an embodiment of the disclosure.

In a preferred embodiment, the serotype 22F glycoconjugate of the invention comprises at least 0.1, 0.2, 0.3, 0.4, 0.5, 0.6 or 0.7 or about 0.8 mM acetate per mM serotype 22F polysaccharide. In a preferred embodiment, the glycoconjugate comprises at least 0.5, 0.6 or 0.7 mM acetate per mM serotype 22F polysaccharide. In a preferred embodiment, the glycoconjugate comprises at least 0.6 mM acetate per mM serotype 22F polysaccharide. In a preferred embodiment, the glycoconjugate comprises at least 0.7 mM acetate per mM serotype 22F polysaccharide.

In a preferred embodiment, the serotype 33F glycoconjugate of the invention comprises at least 0.1, 0.2, 0.3, 0.4, 0.5, 0.6, 0.7 or 0.8 mM acetate per mM serotype 33F capsular polysaccharide. In a preferred embodiment, the glycoconjugate comprises at least 0.5, 0.6 or 0.7 mM acetate per mM serotype 33F capsular polysaccharide. In a preferred embodiment, the glycoconjugate comprises at least 0.6 mM acetate per mM serotype 33F capsular polysaccharide. In a preferred embodiment, the glycoconjugate comprises at least 0.7 mM acetate per mM serotype 33F capsular polysaccharide. In a preferred embodiment, the presence of O-acetyl groups is determined by ion-HPLC analysis.

In a preferred embodiment, the serotype 15B glycoconjugate of the invention comprises at least 0.1, 0.2, 0.3, 0.4, 0.5, 0.6, 0.7 or 0.8 mM acetate per mM serotype 15B capsular polysaccharide. In a preferred embodiment, the glycoconjugate comprises at least 0.5, 0.6 or 0.7 mM acetate per mM serotype 15B capsular polysaccharide. In a preferred embodiment, the glycoconjugate comprises at least 0.6 mM acetate per mM serotype 15B capsular polysaccharide. In a preferred embodiment, the glycoconjugate comprises at least 0.7 mM acetate per mM serotype 15B capsular polysaccharide. In a preferred embodiment, the presence of O-acetyl groups is determined by ion-HPLC analysis.

In a preferred embodiment, the serotype 15B glycoconjugate of the invention comprises at least 0.1, 0.2, 0.3, 0.4, 0.5, 0.6, 0.7 or 0.8 mM glycerol per mM serotype 15B capsular polysaccharide. In a preferred embodiment, the serotype 15B glycoconjugate of the invention comprises at least 0.5, 0.6 or 0.7 mM glycerol per mM serotype 15B capsular polysaccharide. In a preferred embodiment, the serotype 15B glycoconjugate of the invention comprises at least 0.6 mM glycerol per mM serotype 15B capsular polysaccharide. In a preferred embodiment, the serotype 15B glycoconjugate of the invention comprises at least 0.7 mM glycerol per mM serotype 15B capsular polysaccharide.

In a preferred embodiment, the serotype 11A glycoconjugate of the invention comprises at least 0.3, 0.5, 0.6, 1.0, 1.4, 1.8, 2.2, 2.6, 3.0, 3.4, 3.8, 4.2, 4.6 or about 5.0 mM acetate per mM serotype 11A polysaccharide. In a preferred embodiment, the serotype 11A glycoconjugate comprises at least 1.8, 2.2 or 2.6 mM acetate per mM serotype 11A polysaccharide. In an embodiment, the glycoconjugate comprises at least 0.6 mM acetate per mM serotype 11A polysaccharide. In a preferred embodiment, the serotype 11A glycoconjugate of the invention comprises at least 0.6, 1.0, 1.4, 1.8, 2.2, 2.6, 3.0, 3.4, 3.8, 4.2 or about 4.6 mM acetate per mM serotype 11A polysaccharide and less than about 5.0 mM acetate per mM serotype 11A polysaccharide. In an embodiment, the serotype 11A glycoconjugate of the invention comprises at least 0.6, 1.0, 1.4, 1.8, 2.2, 2.6, or about 3.0 mM acetate per mM serotype 11A polysaccharide and less than about 3.4 mM acetate per mM serotype 11A polysaccharide. In an embodiment, the serotype 11A glycoconjugate of the invention comprises at least 0.6, 1.0, 1.4, 1.8, 2.2, 2.6, or about 3.0 mM acetate per mM serotype 11A polysaccharide and less than about 3.3 mM acetate per mM serotype 11A polysaccharide. Any of the above number is contemplated as an embodiment of the disclosure.

In a preferred embodiment, the serotype 11A glycoconjugate of the invention comprises at least 0.1, 0.2, 0.3, 0.4, 0.5, 0.6, 0.7, 0.8, 0.9 or about 1.0 mM glycerol per mM serotype 11A polysaccharide. In a preferred embodiment, the serotype 11A glycoconjugate comprises at least 0.2, 0.3 or 0.4 mM glycerol per mM serotype 11A polysaccharide. In a preferred embodiment, the serotype 11A glycoconjugate of the invention comprises at least 0.1, 0.2, 0.3, 0.4, 0.5, 0.6, 0.7, 0.8 or about 0.9 mM glycerol per mM serotype 11A polysaccharide and less than about 1.0 mM glycerol per mM serotype 11A polysaccharide. In a preferred embodiment, the serotype 11A glycoconjugate of the invention comprises at least 0.3, 0.4, 0.5, 0.6, or about 0.7 mM glycerol per mM serotype 11A polysaccharide and less than about 0.8 mM glycerol per mM serotype 11A polysaccharide. Any of the above number is contemplated as an embodiment of the disclosure.

Another way to characterize the glycoconjugates of the invention is by the number of lysine residues in the carrier protein (e.g., $CRM_{197}$) that become conjugated to the saccharide which can be characterized as a range of conjugated lysines (degree of conjugation). The evidence for lysine modification of the carrier protein, due to covalent linkages to the polysaccharides, can be obtained by amino acid analysis using routine methods known to those of skill in the art. Conjugation results in a reduction in the number of lysine residues recovered, compared to the carrier protein starting material used to generate the conjugate materials. In a preferred embodiment, the degree of conjugation of the glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the glycoconjugate of the invention is about 2, about 3, about 4, about 5, about 6, about 7, about 8, about 9, about 10, about 11, about 12, about 13, about 14 or about 15. In a preferred embodiment, the degree of conjugation of the glycoconjugate of the invention is between 4 and 7. In some such embodiments, the carrier protein is $CRM_{197}$.

The glycoconjugates of the invention may also be characterized by the ratio (weight/weight) of saccharide to carrier protein. In some embodiments, the ratio of polysaccharide to carrier protein in the glycoconjugate (w/w) is between 0.5 and 3 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of capsular polysaccharide to carrier protein in the conjugate is between 0.9 and 1.1. In some such embodiments, the carrier protein is $CRM_{197}$.

The glycoconjugates and immunogenic compositions of the invention may contain free saccharide that is not covalently conjugated to the carrier protein, but is nevertheless present in the glycoconjugate composition. The free saccharide may be non-covalently associated with (i.e., non-covalently bound to, adsorbed to, or entrapped in or with) the glycoconjugate.

In a preferred embodiment, the glycoconjugate comprises less than about 50%, 45%, 40%, 35%, 30%, 25%, 20% or 15% of free polysaccharide compared to the total amount of polysaccharide. In a preferred embodiment the glycoconjugate comprises less than about 25% of free polysaccharide compared to the total amount of polysaccharide. In a preferred embodiment the glycoconjugate comprises less than about 20% of free polysaccharide compared to the total amount of polysaccharide. In a preferred embodiment the glycoconjugate comprises less than about 15% of free polysaccharide compared to the total amount of polysaccharide.

The glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates.

Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d=0$), and the fraction representing the maximum retention ($V_i$), ($K_d=1$). The fraction at which a specified sample attribute is reached ($V_e$), is related to $K_d$ by the expression, $K_d=(V_e-V_0)/(V_i-V_0)$.

In a preferred embodiment, at least 30% of the glycoconjugate has a $K_d$ below or equal to 0.3 in a CL-4B column. In a preferred embodiment, at least 40% of the glycoconjugate has a $K_d$ below or equal to 0.3 in a CL-4B column. In a preferred embodiment, at least 45%, 50%, 55%, 60%, 65%, 70%, 75%, 80% or 85% of the glycoconjugate has a $K_d$ below or equal to 0.3 in a CL-4B column. In a preferred embodiment, at least 60% of the glycoconjugate has a $K_d$ below or equal to 0.3 in a CL-4B column. In a preferred embodiment, between 50% and 80% of the glycoconjugate has a $K_d$ below or equal to 0.3 in a CL-4B column. In a preferred embodiment, between 65% and 80% of the glycoconjugate has a $K_d$ below or equal to 0.3 in a CL-4B column. The frequency of attachment of the saccharide chain to a lysine on the carrier protein is another parameter for characterizing the glycoconjugates of the invention. For example, in some embodiments, at least one covalent linkage between the carrier protein and the polysaccharide occurs for every 4 saccharide repeat units of the polysaccharide. In another embodiment, the covalent linkage between the carrier protein and the polysaccharide occurs at least once in every 10 saccharide repeat units of the polysaccharide. In another embodiment, the covalent linkage between the carrier protein and the polysaccharide occurs at least once in every 15 saccharide repeat units of the polysaccharide. In a further embodiment, the covalent linkage between the carrier protein and the polysaccharide occurs at least once in every 25 saccharide repeat units of the polysaccharide.

In frequent embodiments, the carrier protein is $CRM_{197}$ and the covalent linkage via an eTEC spacer between the $CRM_{197}$ and the polysaccharide occurs at least once in every 4, 10, 15 or 25 saccharide repeat units of the polysaccharide.

In other embodiments, the conjugate comprises at least one covalent linkage between the carrier protein and saccharide for every 5 to 10 saccharide repeat units; every 2 to 7 saccharide repeat units; every 3 to 8 saccharide repeat units; every 4 to 9 saccharide repeat units; every 6 to 11 saccharide repeat units; every 7 to 12 saccharide repeat units; every 8 to 13 saccharide repeat units; every 9 to 14 saccharide repeat units; every 10 to 15 saccharide repeat units; every 2 to 6 saccharide repeat units, every 3 to 7 saccharide repeat units; every 4 to 8 saccharide repeat units; every 6 to 10 saccharide repeat units; every 7 to 11 saccharide repeat units; every 8 to 12 saccharide repeat units; every 9 to 13 saccharide repeat units; every 10 to 14 saccharide repeat units; every 10 to 20 saccharide repeat units; every 4 to 25 saccharide repeat units or every 2 to 25 saccharide repeat units. In frequent embodiments, the carrier protein is $CRM_{197}$.

In another embodiment, at least one linkage between carrier protein and saccharide occurs for every 2, 3, 4, 5, 6, 7, 8, 9, 10, 11, 12, 13, 14, 15, 16, 17, 18, 19, 20, 21, 22, 23, 24 or 25 saccharide repeat units of the polysaccharide. In an embodiment, the carrier protein is $CRM_{197}$. Any whole number integer within any of the above ranges is contemplated as an embodiment of the disclosure.

1.3.2 Serotype 18C Glycoconjugates of the Invention

In one embodiment, the 18C glycoconjugates of the invention are as defined in the present section.

Capsular polysaccharides from serotype 18C of *S. pneumoniae* are prepared as disclosed above.

In an embodiment, the polysaccharides are activated with 1-cyano-4-dimethylamino pyridinium tetrafluoroborate (CDAP) to form a cyanate ester. The activated polysaccharide is then coupled directly or via a spacer (linker) group to an amino group on the carrier protein (preferably $CRM_{197}$). For example, the spacer could be cystamine or cysteamine to give a thiolated polysaccharide which could be coupled to the carrier via a thioether linkage obtained after reaction with a maleimide-activated carrier protein (for example using N-[γ-maleimidobutyrloxy]succinimide ester (GMBS)) or a haloacetylated carrier protein (for example using iodoacetimide, N-succinimidyl bromoacetate (SBA; SIB), N-succinimidyl(4-iodoacetyl)aminobenzoate (SIAB), sulfosuccinimidyl(4-iodoacetyl)aminobenzoate (sulfo-SIAB), N-succinimidyl iodoacetate (SIA), or succinimidyl 3-[bromoacetamido]proprionate (SBAP)). Preferably, the cyanate ester (optionally made by CDAP chemistry) is coupled with hexane diamine or adipic acid dihydrazide (ADH) and the amino-derivatised saccharide is conjugated to the carrier protein (e.g., $CRM_{197}$) using carbodiimide (e.g., EDAC or EDC) chemistry via a carboxyl group on the protein carrier. Such conjugates are described for example in WO 93/15760, WO 95/08348 and WO 96/129094.

In an embodiment of the present invention, the glycoconjugate from *S. pneumoniae* serotype 18C is prepared using CDAP chemistry.

Other suitable techniques for conjugation use carbodiimides, hydrazides, active esters, norborane, p-nitrobenzoic acid, N-hydroxysuccinimide, S—NHS, EDC, TSTU. Many are described in International Patent Application Publication No. WO 98/42721. Conjugation may involve a carbonyl linker which may be formed by reaction of a free hydroxyl group of the saccharide with CDI (see Bethell et al. (1979) 1. Biol. Chem. 254:2572-2574; Hearn et al. (1981) J. Chromatogr. 218:509-518) followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

In an preferred embodiment, capsular polysaccharide from serotype 18C of *S. pneumoniae* is conjugated to the carrier protein by reductive amination (such as described in U.S. Patent Appl. Pub. Nos. 2006/0228380, 2007/184072, 2007/0231340 and 2007/0184071, WO 2006/110381, WO 2008/079653, and WO 2008/143709).

Reductive amination involves two steps as disclosed above.

In some embodiments, the glycoconjugate from *S. pneumoniae* serotype 18C of the invention is O-acetylated. In some embodiments, the glycoconjugate from *S. pneumoniae* serotype 18C is de-O-acetylated.

In some embodiments, the glycoconjugate from *S. pneumoniae* serotype 18C comprise a saccharide which has a degree of O-acetylation of between 10 and 100%, between 20 and 100%, between 30 and 100%, between 40 and 100%, between 50 and 100%, between 60 and 100%, between 70 and 100%, between 75 and 100%, 80 and 100%, 90 and 100%, 50 and 90%, 60 and 90%, 70 and 90% or 80 and 90%. In other embodiments, the degree of O-acetylation is ≥10%, ≥20%, ≥30%, ≥40%, ≥50%, ≥60%, ≥70%, ≥80%, ≥90%, or about 100%. Preferably though, the glycoconjugate from *S. pneumoniae* serotype 18C is de-O-acetylated. In some said embodiments, the glycoconjugate from *S. pneumoniae* serotype 18C comprise a saccharide which has a degree of O-acetylation of between 0 and 50%, between 0 and 40%, between 0 and 30%, between 0 and 20%, between 0 and 10%, between 0 and 5%, or between 0 and 2%. In other embodiments, the degree of O-acetylation is ≤50%, ≤40%, ≤30%, ≤20%, ≤10%, ≤5%, ≤2%, or ≤1%.

By % of O-acetylation it is meant the percentage of a given saccharide relative to 100% (where each repeat unit is fully acetylated relative to its acetylated structure).

In some embodiments, the glycoconjugate from *S. pneumoniae* serotype 18C of the present invention comprises a saccharide having a molecular weight of between 5 kDa and 2,000 kDa. In other such embodiments, the saccharide has a molecular weight of between 10 kDa and 1,000 kDa. In other such embodiments, the saccharide has a molecular weight of between 15 kDa and 900 kDa. In other such embodiments, the saccharide has a molecular weight of between 20 kDa and 800 kDa. In further such embodiments, the saccharide has a molecular weight of between 100 kDa to 1000 kDa; 100 kDa to 900 kDa; 100 kDa to 800 kDa; 100 kDa to 700 kDa; 100 kDa to 600 kDa; 100 kDa to 500 kDa; 100 kDa to 400 kDa; 100 kDa to 300 kDa; 150 kDa to 1,000 kDa; 150 kDa to 900 kDa; 150 kDa to 800 kDa; 150 kDa to 700 kDa; 150 kDa to 600 kDa; 150 kDa to 500 kDa; 150 kDa to 400 kDa; 150 kDa to 300 kDa; 200 kDa to 1,000 kDa; 200 kDa to 900 kDa; 200 kDa to 800 kDa; 200 kDa to 700 kDa; 200 kDa to 600 kDa; 200 kDa to 500 kDa; 200 kDa to 400 kDa; 200 kDa to 300; 250 kDa to 1,000 kDa; 250 kDa to 900 kDa; 250 kDa to 800 kDa; 250 kDa to 700 kDa; 250 kDa to 600 kDa; 250 kDa to 500 kDa; 250 kDa to 400 kDa; 250 kDa to 350 kDa; 300 kDa to 1,000 kDa; 300 kDa to 900 kDa; 300 kDa to 800 kDa; 300 kDa to 700 kDa; 300 kDa to 600 kDa; 300 kDa to 500 kDa; 300 kDa to 400 kDa; 400 kDa to 1,000 kDa; 400 kDa to 900 kDa; 400 kDa to 800 kDa; 400 kDa to 700 kDa; 400 kDa to 600 kDa; 500 kDa to 600 kDa. In further preferred embodiments, the saccharide has a molecular weight of between 5 kDa to 100 kDa; 7 kDa to 100 kDa; 10 kDa to 100 kDa; 20 kDa to 100 kDa; 30 kDa to 100 kDa; 40 kDa to 100 kDa; 50 kDa to 100 kDa; 60 kDa to 100 kDa; 70 kDa to 100 kDa; 80 kDa to 100 kDa or 90 kDa to 100 kDa. In further preferred embodiments, the saccharide has a molecular weight of between 5 kDa to 90 KDa; 5 kDa to 80 kDa; 5 kDa to 70 kDa; 5 kDa to 60 kDa; 5 kDa to 50 kDa; 5 kDa to 40 kDa; 5 kDa to 30 kDa; 5 kDa to 20 kDa, 5 kDa to 10 kDa, 10 kDa to 90 KDa; 10 kDa to 80 kDa; 10 kDa to 70 kDa; 10 kDa to 60 kDa; 10 kDa to 50 kDa; 10 kDa to 40 kDa; 10 kDa to 30 kDa; 10 kDa to 20 kDa, 20 kDa to 90 KDa; 20 kDa to 80 kDa; 20 kDa to 70 kDa; 20 kDa to 60 kDa; 20 kDa to 50 kDa; 20 kDa to 40 kDa or 20 kDa to 30 kDa. In further preferred embodiments, the saccharide has a molecular weight of between 30 kDa to 90 KDa; 30 kDa to 80 kDa; 30 kDa to 70 kDa; 30 kDa to 60 kDa; 30 kDa to 50 kDa; 30 kDa to 40 kDa; 40 kDa to 90 KDa; 40 kDa to 80 kDa; 40 kDa to 70 kDa; 40 kDa to 60 kDa; 40 kDa to 50 kDa; 50 kDa to 90 KDa; 50 kDa to 80 kDa; 50 kDa to 70 kDa or 50 kDa to 60 kDa. Any whole number integer within any of the above ranges is contemplated as an embodiment of the disclosure. In some such embodiments, the glycoconjugate is prepared using reductive amination.

In some embodiments, the glycoconjugate from *S. pneumoniae* serotype 18C of the present invention has a molecular weight of between 100 kDa and 20,000 kDa; between 200 kDa and 10,000 kDa or between 300 kDa and 5,000 kDa. In further embodiments, the glycoconjugate from *S. pneumoniae* serotype 18C of the invention has a molecular weight of between 100 kDa and 5,000 kDa; between 150 kDa and 4,000 kDa; between 200 kDa and 3,000 kDa or between 250 kDa and 2,000 kDa. In further embodiments, the glycoconjugate from *S. pneumoniae* serotype 18C of the invention has a molecular weight of between 100 kDa and 2,000 kDa; between 150 kDa and 2,000 kDa; between 200 kDa and 2,000 kDa; between 250 kDa and 2,000 kDa; between 300 kDa and 2,000 kDa; between 350 kDa and 2,000 kDa; between 400 kDa and 2,000 kDa; between 450 kDa and 2,000 kDa; between 500 kDa and 2,000 kDa; between 550 kDa and 2,000 kDa; between 600 kDa and 2,000 kDa; between 700 kDa and 2,000 kDa; between 800 kDa and 2,000 kDa; between 900 kDa and 2,000 kDa; between 1,000 kDa and 2,000 kDa; between 1,250 kDa and 2,000 kDa; between 1,500 kDa and 2,000 kDa or between 1,750 kDa and 2,000 kDa. In further embodiments, the glycoconjugate from *S. pneumoniae* serotype 18C of the invention has a molecular weight of between 150 kDa and 2,000 kDa; between 150 kDa and 1,900 kDa; between 150 kDa and 1,800 kDa; between 150 kDa and 1,700 kDa; between 150 kDa and 1,600 kDa; between 150 kDa and 1,500 kDa; between 150 kDa and 1,400 kDa; between 150 kDa and 1,300 kDa; between 150 kDa and 1,200 kDa; between 150 kDa and 1,100 kDa; between 150 kDa and 1,000 kDa; between 150 kDa and 900 kDa; between 150 kDa and 800 kDa; between 150 kDa and 700 kDa; between 150 kDa and 600 kDa; between 150 kDa and 500 kDa; between 150 kDa and 400 kDa; between 150 kDa and 300 kDa or between 150 kDa and 200 kDa. In further embodiments, the glycoconjugate from *S. pneumoniae* serotype 18C of the invention has a molecular weight of between 200 kDa and 2,000 kDa; between 200 kDa and 1,900 kDa; between 200 kDa and 1,800 kDa; between 200 kDa and 1,700 kDa; between 200 kDa and 1,600 kDa; between 200 kDa and 1,500 kDa; between 200 kDa and 1,400 kDa; between 200 kDa and 1,300 kDa; between 200 kDa and 1,200 kDa; between 200 kDa and 1,100 kDa; between 200 kDa and 1,000 kDa; between 200 kDa and 900 kDa; between 200 kDa and 800 kDa; between 200 kDa and 700 kDa; between 200 kDa and 600 kDa; between 200 kDa and 500 kDa; between 200 kDa and 400 kDa or between 200 kDa and 300 kDa. In further embodiments, the glycoconjugate from S. pneumoniae serotype 18C of the invention has a molecular weight of between 250 kDa and 2,000 kDa; between 250 kDa and 1,900 kDa; between 250 kDa and 1,800 kDa; between 250 kDa and 1,700 kDa; between 250 kDa and 1,600 kDa; between 250 kDa and 1,500 kDa; between 250 kDa and 1,400 kDa; between 250 kDa and 1,300 kDa; between 250 kDa and 1,200 kDa; between 250 kDa and 1,100 kDa; between 250 kDa and 1,000 kDa; between 250 kDa and 900 kDa; between 250 kDa and 800 kDa; between 250 kDa and 700 kDa; between 250 kDa and 600 kDa; between 250 kDa and 500 kDa; between 250 kDa and 400 kDa or between 250 kDa and 300 kDa. In further embodiments, the glycoconjugate from S. pneumoniae serotype 18C of the invention has a molecular weight of between 300 kDa and 2,000 kDa; between 300 kDa and 1,900 kDa; between 300 kDa and 1,800 kDa; between 300 kDa and 1,700 kDa; between 300 kDa and 1,600 kDa; between 300 kDa and 1,500 kDa; between 300 kDa and 1,400 kDa; between 300 kDa and 1,300 kDa; between 300 kDa and 1,200 kDa; between 300 kDa and 1,100 kDa; between 300 kDa and 1,000 kDa; between 300 kDa and 900 kDa; between 300 kDa and 800 kDa; between 300 kDa and 700 kDa; between 300 kDa and 600 kDa; between 300 kDa and 500 kDa or between 300 kDa and 400 kDa. In further embodiments, the glycoconjugate from S. pneumoniae serotype 18C of the invention has a molecular weight of between 400 kDa and 2,000 kDa; between 400 kDa and 1,900 kDa; between 400 kDa and 1,800 kDa; between 400 kDa and 1,700 kDa; between 400 kDa and 1,600 kDa; between 400 kDa and 1,500 kDa; between 400 kDa and 1,400 kDa; between 400 kDa and 1,300 kDa; between 400 kDa and 1,200 kDa; between 400 kDa and 1,100 kDa; between 400 kDa and 1,000 kDa; between 400 kDa and 900 kDa; between 400 kDa and 800 kDa; between 400 kDa and 700 kDa; between 400 kDa and 600 kDa or between 400 kDa and 500 kDa. In further embodiments, the glycoconjugate from S. pneumoniae serotype 18C of the invention has a molecular weight of between 500 kDa and 2,000 kDa; between 500 kDa and 1,900 kDa; between 500 kDa and 1,800 kDa; between 500 kDa and 1,700 kDa; between 500 kDa and 1,600 kDa; between 500 kDa and 1,500 kDa; between 500 kDa and 1,400 kDa; between 500 kDa and 1,300 kDa; between 500 kDa and 1,200 kDa; between 500 kDa and 1,100 kDa; between 500 kDa and 1,000 kDa; between 500 kDa and 900 kDa; between 500 kDa and 800 kDa; between 500 kDa and 700 kDa or between 500 kDa and 600 kDa.

The molecular weight of the glycoconjugate is measured by SEC-MALLS. Any whole number integer within any of the above ranges is contemplated as an embodiment of the disclosure.

Another way to characterize the glycoconjugates of the invention is by the number of lysine residues in the carrier protein (e.g., $CRM_{197}$) that become conjugated to the saccharide which can be characterized as a range of conjugated lysines (degree of conjugation). The evidence for lysine modification of the carrier protein, due to covalent linkages to the polysaccharides, can be obtained by amino acid analysis using routine methods known to those of skill in the art. Conjugation results in a reduction in the number of lysine residues recovered, compared to the carrier protein starting material used to generate the conjugate materials. In a preferred embodiment, the degree of conjugation of the glycoconjugate from S. pneumoniae serotype 18C of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the glycoconjugate from S. pneumoniae serotype 18C of the invention is about 2, about 3, about 4, about 5, about 6, about 7, about 8, about 9, about 10, about 11, about 12, about 13, about 14 or about 15. In a preferred embodiment, the degree of conjugation of the glycoconjugate from S. pneumoniae serotype 18C of the invention is between 4 and 7. In some such embodiments, the carrier protein is $CRM_{197}$.

The glycoconjugate from S. pneumoniae serotype 18C of the invention may also be characterized by the ratio (weight/weight) of saccharide to carrier protein. In some embodiments, the ratio of polysaccharide to carrier protein in the glycoconjugate from S. pneumoniae serotype 18C of the invention (w/w) is between 0.5 and 3 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of capsular polysaccharide to carrier protein in the conjugate is between 0.9 and 1.1. In some such embodiments, the carrier protein is $CRM_{197}$.

In a preferred embodiment, the glycoconjugate from S. pneumoniae serotype 18C of the invention comprises less than about 50%, 45%, 40%, 35%, 30%, 25%, 20% or 15% of free polysaccharide compared to the total amount of polysaccharide. In a preferred embodiment the glycoconjugate comprises less than about 25% of free polysaccharide compared to the total amount of polysaccharide. In a preferred embodiment the glycoconjugate comprises less than about 20% of free polysaccharide compared to the total amount of polysaccharide. In a preferred embodiment the glycoconjugate comprises less than about 15% of free polysaccharide compared to the total amount of polysaccharide.

The glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d=0$), and the fraction representing the maximum retention ($V_i$), ($K_d=1$). The fraction at which a specified sample attribute is reached ($V_e$), is related to $K_d$ by the expression, $K_d=(V_e-V_o)/(V_i-V_o)$.

In a preferred embodiment, at least 30% of the glycoconjugate from *S. pneumoniae* serotype 18C of the invention has a $K_d$ below or equal to 0.3 in a CL-4B column. In a preferred embodiment, at least 40% of the glycoconjugate has a $K_d$ below or equal to 0.3 in a CL-4B column. In a preferred embodiment, at least 45%, 50%, 55%, 60%, 65%, 70%, 75%, 80%, or 85% of the glycoconjugate has a $K_d$ below or equal to 0.3 in a CL-4B column. In a preferred embodiment, at least 60% of the glycoconjugate has a $K_d$ below or equal to 0.3 in a CL-4B column. In a preferred embodiment, between 50% and 80% of the glycoconjugate has a $K_d$ below or equal to 0.3 in a CL-4B column. In a preferred embodiment, between 65% and 80% of the glycoconjugate has a $K_d$ below or equal to 0.3 in a CL-4B column.

The frequency of attachment of the saccharide chain to a lysine on the carrier protein is another parameter for characterizing the glycoconjugate from *S. pneumoniae* serotype 18C of the invention. For example, in some embodiments, at least one covalent linkage between the carrier protein and the polysaccharide occurs for every 4 saccharide repeat units of the polysaccharide. In another embodiment, the covalent linkage between the carrier protein and the polysaccharide occurs at least once in every 10 saccharide repeat units of the polysaccharide. In another embodiment, the covalent linkage between the carrier protein and the polysaccharide occurs at least once in every 15 saccharide repeat units of the polysaccharide. In a further embodiment, the covalent linkage between the carrier protein and the polysaccharide occurs at least once in every 25 saccharide repeat units of the polysaccharide.

In other embodiments, the conjugate comprises at least one covalent linkage between the carrier protein and saccharide for every 5 to 10 saccharide repeat units; every 2 to 7 saccharide repeat units; every 3 to 8 saccharide repeat units; every 4 to 9 saccharide repeat units; every 6 to 11 saccharide repeat units; every 7 to 12 saccharide repeat units; every 8 to 13 saccharide repeat units; every 9 to 14 saccharide repeat units; every 10 to 15 saccharide repeat units; every 2 to 6 saccharide repeat units, every 3 to 7 saccharide repeat units; every 4 to 8 saccharide repeat units; every 6 to 10 saccharide repeat units; every 7 to 11 saccharide repeat units; every 8 to 12 saccharide repeat units; every 9 to 13 saccharide repeat units; every 10 to 14 saccharide repeat units; every 10 to 20 saccharide repeat units; every 4 to 25 saccharide repeat units or every 2 to 25 saccharide repeat units. In frequent embodiments, the carrier protein is $CRM_{197}$.

In another embodiment, at least one linkage between carrier protein and saccharide occurs for every 2, 3, 4, 5, 6, 7, 8, 9, 10, 11, 12, 13, 14, 15, 16, 17, 18, 19, 20, 21, 22, 23, 24 or 25 saccharide repeat units of the polysaccharide. In an embodiment, the carrier protein is $CRM_{197}$. Any whole number integer within any of the above ranges is contemplated as an embodiment of the disclosure.

1.4 Combination of Glycoconjugates of the Invention

In an embodiment the immunogenic composition of the invention comprises any of the glycoconjugates disclosed herein.

1.4.1 Combinations of Glycoconjugates

In an embodiment the immunogenic composition of the invention comprises at least one glycoconjugate from *S. pneumoniae* serotype 18C.

In an embodiment the immunogenic composition of the invention comprises at least one glycoconjugate of each of the two following *S. pneumoniae* serotypes: 18C and 4, 18C and 6B, 18C and 14, 18C and 9V, 18C and 19F or 18C and 23F.

In an embodiment the immunogenic composition of the invention comprises at least one glycoconjugate of each of the seven following *S. pneumoniae* serotypes: 18C, 4, 6B, 9V, 14, 19F and 23F.

In an embodiment the immunogenic composition of the invention comprises at least one glycoconjugate of each of the eight following *S. pneumoniae* serotypes: 1, 4, 6B, 9V, 14, 18C, 19F, and 23F; 4, 5, 6B, 9V, 14, 18C, 19F, and 23F; 4, 6B, 7F, 9V, 14, 18C, 19F, and 23F.

In an embodiment the immunogenic composition of the invention comprises at least one glycoconjugate of each of the ten following *S. pneumoniae* serotypes: 1, 5, 4, 6B, 7F, 9V, 14, 18C, 19F and 23F.

In an embodiment the immunogenic composition of the invention comprises at least one glycoconjugate of each of the eleven following *S. pneumoniae* serotypes: 1, 4, 5, 6A, 6B, 7F, 9V, 14, 18C, 19F, and 23F; 1, 4, 5, 6B, 7F, 9V, 14, 18C, 19A, 19F, and 23F.

In an embodiment the immunogenic composition of the invention comprises at least one glycoconjugate of each of the twelve following *S. pneumoniae* serotypes: 1, 4, 5, 6A, 6B, 7F, 9V, 14, 18C, 19A, 19F, and 23F.

In an embodiment the immunogenic composition of the invention comprises at least one glycoconjugate of each of the thirteen following *S. pneumoniae* serotypes: 1, 3, 4, 5, 6A, 6B, 7F, 9V, 14, 18C, 19A, 19F, and 23F.

1.4.2 Additional Combinations of Glycoconjugates

In an embodiment any of the immunogenic composition defined at 1.4.1 above comprises in addition at least one glycoconjugate of *S. pneumoniae* serotype 15B.

In an embodiment any of the immunogenic composition defined at 1.4.1 above comprises in addition at least one glycoconjugate of *S. pneumoniae* serotype 22F.

In an embodiment any of the immunogenic composition defined at 1.4.1 above comprises in addition at least one glycoconjugate of *S. pneumoniae* serotype 33F.

In an embodiment any of the immunogenic composition defined at 1.4.1 above comprises in addition at least one glycoconjugate of *S. pneumoniae* serotype 8.

In an embodiment any of the immunogenic composition defined at 1.4.1 above comprises in addition at least one glycoconjugate of *S. pneumoniae* serotype 10A.

In an embodiment any of the immunogenic composition defined at 1.4.1 above comprises in addition at least one glycoconjugate of *S. pneumoniae* serotype 11A.

In an embodiment any of the immunogenic composition defined at 1.4.1 above comprises in addition at least one glycoconjugate of *S. pneumoniae* serotype 12F.

In an embodiment any of the immunogenic composition defined at 1.4.1 above comprises in addition at least one glycoconjugate of each of the two following *S. pneumoniae* serotypes:
15B and 22F,
15B and 33F,
15B and 12F,
15B and 10A,
15B and 11A,
15B and 8,
22F and 33F,
22F and 12F, 22F and 10A,
22F and 11A,
22F and 8,
33F and 12F,
33F and 10A,
33F and 11A,
33F and 8,
12F and 10A,
12F and 11A,
12F and 8,
10A and 11A,
10A and 8, or
11A and 8.

In an embodiment any of the immunogenic composition defined at 1.4.1 above comprises in addition at least one glycoconjugate of each of the three following S. pneumoniae serotypes:
15B and 22F and 33F,
15B and 22F and 12F,
15B and 22F and 10A,
15B and 22F and 11A,
15B and 22F and 8,
15B and 33F and 12F,
15B and 33F and 10A,
15B and 33F and 11A,
15B and 33F and 8,
15B and 12F and 10A,
15B and 12F and 11A,
15B and 12F and 8,
15B and 10A and 11A,
15B and 10A and 8,
15B and 11A and 8,
22F and 33F and 12F,
22F and 33F and 10A,
22F and 33F and 11A,
22F and 33F and 8,
22F and 12F and 10A,
22F and 12F and 11A,
22F and 12F and 8,
22F and 10A and 11A,
22F and 10A and 8,
22F and 11A and 8,
33F and 12F and 10A,
33F and 12F and 11A,
33F and 12F and 8,
33F and 10A and 11A,
33F and 10A and 8,
33F and 11A and 8,
12F and 10A and 11A,
12F and 10A and 8,
12F and 11A and 8, or
10A and 11A and 8.

In an embodiment any of the immunogenic composition defined at 1.4.1 above comprises in addition at least one glycoconjugate of each of the four following S. pneumoniae serotypes:
15B and 22F and 33F and 12F,
15B and 22F and 33F and 10A,
15B and 22F and 33F and 11A,
15B and 22F and 33F and 8,
15B and 22F and 12F and 10A,
15B and 22F and 12F and 11A,
15B and 22F and 12F and 8,
15B and 22F and 10A and 11A,
15B and 22F and 10A and 8,
15B and 22F and 11A and 8,
15B and 33F and 12F and 10A,
15B and 33F and 12F and 11A,
15B and 33F and 12F and 8,
15B and 33F and 10A and 11A,
15B and 33F and 10A and 8,
15B and 33F and 11A and 8,
15B and 12F and 10A and 11A,
15B and 12F and 10A and 8,
15B and 12F and 11A and 8,
15B and 10A and 11A and 8,
22F and 33F and 12F and 10A,
22F and 33F and 12F and 11A,
22F and 33F and 12F and 8,
22F and 33F and 10A and 11A,
22F and 33F and 10A and 8,
22F and 33F and 11A and 8,
22F and 12F and 10A and 11A,
22F and 12F and 10A and 8,
22F and 12F and 11A and 8,
22F and 10A and 11A and 8,
33F and 12F and 10A and 11A,
33F and 12F and 10A and 8,
33F and 12F and 11A and 8,
33F and 10A and 11A and 8 or
12F and 10A and 11A and 8.

In an embodiment any of the immunogenic composition defined at 1.4.1 above comprises in addition at least one glycoconjugate of each of the five following S. pneumoniae serotypes:
15B and 22F and 33F and 12F and 10A,
15B and 22F and 33F and 12F and 11A,
15B and 22F and 33F and 12F and 8,
15B and 22F and 33F and 10A and 11A,
15B and 22F and 33F and 10A and 8,
15B and 22F and 33F and 11A and 8,
15B and 22F and 12F and 10A and 11A,
15B and 22F and 12F and 10A and 8,
15B and 22F and 12F and 11A and 8,
15B and 22F and 10A and 11A and 8,
15B and 33F and 12F and 10A and 11A,
15B and 33F and 12F and 10A and 8,
15B and 33F and 12F and 11A and 8,
15B and 33F and 10A and 11A and 8,
15B and 12F and 10A and 11A and 8,
22F and 33F and 12F and 10A and 11A,
22F and 33F and 12F and 10A and 8,
22F and 33F and 12F and 11A and 8,
22F and 33F and 10A and 11A and 8,
22F and 12F and 10A and 11A and 8 or
33F and 12F and 10A and 11A and 8.

In an embodiment any of the immunogenic composition defined at 1.4.1 above comprises in addition at least one glycoconjugate of each of the six following S. pneumoniae serotypes:
15B and 22F and 33F and 12F and 10A and 11A,
15B and 22F and 33F and 12F and 10A and 8,
15B and 22F and 33F and 12F and 11A and 8,
15B and 22F and 33F and 10A and 11A and 8,
15B and 22F and 12F and 10A and 11A and 8,
15B and 33F and 12F and 10A and 11A and 8 or
22F and 33F and 12F and 10A and 11A and 8.

In an embodiment any of the immunogenic composition defined at 1.4.1 above comprises in addition at least one glycoconjugate of each of the seven following S. pneumoniae serotypes: 15B and 22F and 33F and 12F and 10A and 11A and 8.

In an embodiment any of the immunogenic composition above comprises in addition glycoconjugates from *S. pneumoniae* serotype 2.

In an embodiment any of the immunogenic composition above comprises in addition glycoconjugates from *S. pneumoniae* serotype 17F.

In an embodiment any of the immunogenic composition above comprises in addition glycoconjugates from *S. pneumoniae* serotype 20.

In an embodiment any of the immunogenic composition above comprises in addition glycoconjugates from *S. pneumoniae* serotype 15C.

Preferably, all the glycoconjugates of the above immunogenic composition are individually conjugated to the carrier protein.

In an embodiment of any of the above immunogenic composition, the glycoconjugates from *S. pneumoniae* serotype 18C is conjugated to $CRM_{197}$. In an embodiment of any of the above immunogenic compositions, the glycoconjugates from *S. pneumoniae* serotype 22F is conjugated to $CRM_{197}$. In an embodiment of any of the above immunogenic composition, the glycoconjugates from *S. pneumoniae* serotype 33F is conjugated to $CRM_{197}$. In an embodiment of any of the above immunogenic composition, the glycoconjugates from *S. pneumoniae* serotype 15B is conjugated to $CRM_{197}$. In an embodiment of any of the above immunogenic composition, the glycoconjugates from *S. pneumoniae* serotype 12F is conjugated to $CRM_{197}$. In an embodiment of any of the above immunogenic composition, the glycoconjugates from *S. pneumoniae* serotype 10A is conjugated to $CRM_{197}$. In an embodiment of any of the above immunogenic composition, the glycoconjugates from *S. pneumoniae* serotype 11A is conjugated to $CRM_{197}$. In an embodiment of any of the above immunogenic composition, the glycoconjugates from *S. pneumoniae* serotype 8 is conjugated to $CRM_{197}$. In an embodiment of any of the above immunogenic composition, the glycoconjugates from *S. pneumoniae* serotypes 4, 6B, 9V, 14, 19F and 23F are conjugated to $CRM_{197}$. In an embodiment of any of the above immunogenic composition, the glycoconjugates from *S. pneumoniae* serotypes 1, 5 and 7F are conjugated to $CRM_{197}$. In an embodiment of any of the above immunogenic composition, the glycoconjugates from *S. pneumoniae* serotypes 6A and 19A are conjugated to $CRM_{197}$. In an embodiment of any of the above immunogenic composition, the glycoconjugates from *S. pneumoniae* serotype 3 is conjugated to $CRM_{197}$. In an embodiment of any of the above immunogenic compositions, the glycoconjugates from *S. pneumoniae* serotype 2 is conjugated to $CRM_{197}$. In an embodiment of any of the above immunogenic compositions, the glycoconjugates from *S. pneumoniae* serotype 17F is conjugated to $CRM_{197}$. In an embodiment of any of the above immunogenic compositions, the glycoconjugates from *S. pneumoniae* serotype 20 is conjugated to $CRM_{197}$. In an embodiment of any of the above immunogenic compositions, the glycoconjugates from *S. pneumoniae* serotype 15C is conjugated to $CRM_{197}$.

In an embodiment, the glycoconjugates of the above immunogenic compositions are all individually conjugated to $CRM_{197}$.

In an embodiment, the glycoconjugate from *S. pneumoniae* serotype 18C of any of the above immunogenic composition is individually conjugated to TT.

In an embodiment, the glycoconjugates from *S. pneumoniae* serotypes 1, 4, 5, 6B, 7F, 9V, 14 and/or 23F of any of the above immunogenic compositions are individually conjugated to PD.

In an embodiment, the glycoconjugate from *S. pneumoniae* serotype 19F of any of the above immunogenic compositions is conjugated to DT.

In an embodiment, the glycoconjugates from *S. pneumoniae* serotypes 1, 4, 5, 6B, 7F, 9V, 14 and/or 23F of any of the above immunogenic compositions are individually conjugated to PD, the glycoconjugate from *S. pneumoniae* serotype 18C is conjugated to TT and the glycoconjugate from *S. pneumoniae* serotype 19F is conjugated to DT.

In an embodiment the above immunogenic composition comprises from 7 to 25 different serotypes of *S. pneumoniae*. In one embodiment the above immunogenic composition comprises glycoconjugates from 7, 8, 9, 10, 11, 12, 13, 14, 15, 16, 17, 18, 19, 20, 21, 22, 23, 24 or 25 different serotypes.

In an embodiment the above immunogenic composition comprises from 7 to 20 different serotypes of *S. pneumoniae*. In one embodiment the above immunogenic composition comprises glycoconjugates from 7, 8, 9, 10, 11, 12, 13, 14, 15, 16, 17, 18, 19 or 20 different serotypes. In one embodiment the above immunogenic composition comprises glycoconjugates from 16 or 20 different serotypes.

In an embodiment the above immunogenic composition is a 8, 9, 10, 11, 12, 13, 14, 15, 16, 17, 18, 19 or 20-valent pneumococcal conjugate composition. In an embodiment the above immunogenic composition is a 14, 15, 16, 17, 18 or 19 valent pneumococcal conjugate composition. In an embodiment the above immunogenic composition is a 16-valent pneumococcal conjugate composition. In an embodiment the above immunogenic composition is a 19-valent pneumococcal conjugate composition. In an embodiment the above immunogenic composition is a 20-valent pneumococcal conjugate composition.

In an embodiment, the immunogenic composition of the invention comprises glycoconjugates from *S. pneumoniae* serotypes 1, 3, 4, 5, 6A, 6B, 7F, 9V, 14, 15B, 18C, 19A, 19F, 22F, 23F and 33F.

In an embodiment, the immunogenic composition of the invention comprises glycoconjugates from *S. pneumoniae* serotypes 1, 4, 5, 6A, 6B, 7F, 9V, 14, 15B, 18C, 19A, 19F, 22F, 23F and 33F.

In an embodiment, the immunogenic composition of the invention comprises conjugated *S. pneumoniae* saccharides from serotypes 1, 3, 4, 5, 6A, 6B, 7F, 8, 9V, 10A, 11A, 12F, 14, 15B, 18C, 19A, 19F, 22F, 23F and 33F.

In an embodiment, the immunogenic composition of the invention comprises conjugated *S. pneumoniae* saccharides from serotypes 1, 4, 5, 6A, 6B, 7F, 8, 9V, 10A, 11A, 12F, 14, 15B, 18C, 19A, 19F, 22F, 23F and 33F.

In an embodiment, the glycoconjugates of the immunogenic composition of the invention consists of glycoconjugates from *S. pneumoniae* serotypes 1, 3, 4, 5, 6A, 6B, 7F, 9V, 14, 15B, 18C, 19A, 19F, 22F, 23F and 33F. In an embodiment, the glycoconjugates of the immunogenic composition of the invention consists of glycoconjugates from serotypes 1, 4, 5, 6A, 6B, 7F, 9V, 14, 15B, 18C, 19A, 19F, 22F, 23F and 33F. In an embodiment, the glycoconjugates of the immunogenic composition of the invention consists of glycoconjugates from serotypes 1, 3, 4, 5, 6A, 6B, 7F, 8, 9V, 10A, 11A, 12F, 14, 15B, 18C, 19A, 19F, 22F, 23F and 33F. In an embodiment, the glycoconjugates of the immunogenic composition of the invention consists of glycoconjugates from 1, 4, 5, 6A, 6B, 7F, 8, 9V, 10A, 11A, 12F, 14, 15B, 18C, 19A, 19F, 22F, 23F and 33F.

Preferably, all the glycoconjugates of the immunogenic composition of the invention are individually conjugated to the carrier protein. In an embodiment, the glycoconjugates of the immunogenic composition above are individually conjugated to $CRM_{197}$.

1.4.3 Further Combinations of Glycoconjugates

In an embodiment any of the immunogenic compositions defined at 1.4.1 or 1.4.2 above do not comprise capsular saccharide from *S. pneumoniae* serotype 18F.

In an embodiment any of the immunogenic compositions defined at 1.4.1 or 1.4.2 above do not comprise capsular saccharide from *S. pneumoniae* serotype 18A.

In an embodiment any of the immunogenic compositions defined at 1.4.1 or 1.4.2 above do not comprise capsular saccharide from *S. pneumoniae* serotype 18B.

In an embodiment any of the immunogenic compositions defined at 1.4.1 or 1.4.2 above do not comprise capsular saccharide from *S. pneumoniae* serotypes 18F and 18A.

In an embodiment any of the immunogenic compositions defined at 1.4.1 or 1.4.2 above do not comprise capsular saccharide from *S. pneumoniae* serotypes 18F and 18B.

In an embodiment any of the immunogenic compositions defined at 1.4.1 or 1.4.2 above do not comprise capsular saccharide from *S. pneumoniae* serotypes 18A and 18B.

In an embodiment any of the immunogenic compositions defined at 1.4.1 or 1.4.2 above do not comprise capsular saccharide from *S. pneumoniae* serotypes 18F, 18A and 18B.

2 Dosage of the Immunogenic Compositions

2.1 Polysaccharide Amount

The amount of glycoconjugate(s) in each dose is selected as an amount which induces an immunoprotective response without significant, adverse side effects in typical vaccines. Such amount will vary depending upon which specific immunogen is employed and how it is presented.

The amount of a particular glycoconjugate in an immunogenic composition can be calculated based on total polysaccharide for that conjugate (conjugated and non-conjugated). For example, a glycoconjugate with 20% free polysaccharide will have about 80 μg of conjugated polysaccharide and about 20 μg of non-conjugated polysaccharide in a 100 μg polysaccharide dose. The amount of glycoconjugate can vary depending upon the streptococcal serotype. The saccharide concentration can be determined by the uronic acid assay.

The "immunogenic amount" of the different polysaccharide components in the immunogenic composition, may diverge and each may comprise about 1.0 μg, about 2.0 μg, about 3.0 μg, about 4.0 μg, about 5.0 μg, about 6.0 μg, about 7.0 μg, about 8.0 μg, about 9.0 μg, about 10.0 μg, about 15.0 μg, about 20.0 μg, about 30.0 μg, about 40.0 μg, about 50.0 μg, about 60.0 μg, about 70.0 μg, about 80.0 μg, about 90.0 μg, or about 100.0 μg of any particular polysaccharide antigen.

Generally, each dose will comprise 0.1 μg to 100 μg of polysaccharide for a given serotype, particularly 0.5 μg to 20 μg, more particularly 1 μg to 10 μg, and even more particularly 2 μg to 5 μg. Any whole number integer within any of the above ranges is contemplated as an embodiment of the disclosure.

In an embodiment, each dose will comprise 1 μg, 2 μg, 3 μg, 4 μg, 5 μg, 6 μg, 7 μg, 8 μg, 9 μg, 10 μg, 15 μg or 20 μg of polysaccharide for a given serotype.

2.2 Carrier Amount

Generally, each dose will comprise 5 μg to 150 μg of carrier protein, particularly 10 μg to 100 μg of carrier protein, more particularly 15 μg to 100 μg of carrier protein, more particularly 25 to 75 μg of carrier protein, more particularly 30 μg to 70 μg of carrier protein, more particularly 30 to 60 μg of carrier protein, more particularly 30 μg to 50 μg of carrier protein and even more particularly 40 to 60 μg of carrier protein. In an embodiment, said carrier protein is $CRM_{197}$.

In an embodiment, each dose will comprise about 25 μg, about 26 μg, about 27 μg, about 28 μg, about 29 μg, about 30 μg, about 31 μg, about 32 μg, about 33 μg, about 34 μg, about 35 μg, about 36 μg, about 37 μg, about 38 μg, about 39 μg, about 40 μg, about 41 μg, about 42 μg, about 43 μg, about 44 μg, about 45 μg, about 46 μg, about 47 μg, about 48 μg, about 49 μg, about 50 μg, about 51 μg, about 52 μg, about 53 μg, about 54 μg, about 55 μg, about 56 μg, about 57 μg, about 58 μg, about 59 μg, about 60 μg, about 61 μg, about 62 μg, about 63 μg, about 64 μg, about 65 μg, about 66 μg, about 67 μg, 68 μg, about 69 μg, about 70 μg, about 71 μg, about 72 μg, about 73 μg, about 74 μg or about 75 μg of carrier protein. In an embodiment, said carrier protein is $CRM_{197}$.

3 Further Antigens

Immunogenic compositions of the invention comprise conjugated *S. pneumoniae* saccharide antigens (glycoconjugates). They may also further include antigens from other pathogens, particularly from bacteria and/or viruses. Preferred further antigens are selected from: a diphtheria toxoid (D), a tetanus toxoid (T), a pertussis antigen (P), which is typically acellular (Pa), a hepatitis B virus (HBV) surface antigen (HBsAg), a hepatitis A virus (HAV) antigen, a conjugated *Haemophilus influenzae* type b capsular saccharide (Hib), inactivated poliovirus vaccine (IPV).

In an embodiment, the immunogenic compositions of the invention comprise D-T-Pa. In an embodiment, the immunogenic compositions of the invention comprise D-T-Pa-Hib, D-T-Pa-IPV or D-T-Pa-HBsAg. In an embodiment, the immunogenic compositions of the invention comprise D-T-Pa-HBsAg-IPV or D-T-Pa-HBsAg-Hib. In an embodiment, the immunogenic compositions of the invention comprise D-T-Pa-HBsAg-IPV-Hib.

Pertussis antigens: *Bordetella pertussis* causes whooping cough. Pertussis antigens in vaccines are either cellular (whole cell, in the form of inactivated *B. pertussis* cells) or acellular. Preparation of cellular pertussis antigens is well documented (e.g., it may be obtained by heat inactivation of phase I culture of *B. pertussis*). Preferably, however, the invention uses acellular antigens. Where acellular antigens are used, it is preferred to use one, two or (preferably) three of the following antigens: (1) detoxified pertussis toxin (pertussis toxoid, or PT); (2) filamentous hemagglutinin (FHA); (3) pertactin (also known as the 69 kiloDalton outer membrane protein). FHA and pertactin may be treated with formaldehyde prior to use according to the invention. PT is preferably detoxified by treatment with formaldehyde and/or glutaraldehyde. Acellular pertussis antigens are preferably adsorbed onto one or more aluminum salt adjuvants. As an alternative, they may be added in an unadsorbed state. Where pertactin is added then it is preferably already adsorbed onto an aluminum hydroxide adjuvant. PT and FHA may be adsorbed onto an aluminum hydroxide adjuvant or an aluminum phosphate. Adsorption of all of PT, FHA and pertactin to aluminum hydroxide is most preferred.

Inactivated poliovirus vaccine: Poliovirus causes poliomyelitis. Rather than use oral poliovirus vaccine, preferred embodiments of the invention use IPV. Prior to administration to patients, polioviruses must be inactivated, and this can be achieved by treatment with formaldehyde. Poliomyelitis can be caused by one of three types of poliovirus. The three types are similar and cause identical symptoms, but they are antigenically different and infection by one type does not protect against infection by others. It is therefore preferred to use three poliovirus antigens in the invention: poliovirus Type 1 (e.g., Mahoney strain), poliovirus Type 2 (e.g., MEF-1 strain), and poliovirus Type 3 (e.g., Saukett strain). The viruses are preferably grown, purified and inactivated individually, and are then combined to give a bulk trivalent mixture for use with the invention.

Diphtheria toxoid: *Corynebacterium diphtheriae* causes diphtheria. Diphtheria toxin can be treated (e.g., using formalin or formaldehyde) to remove toxicity while retaining the ability to induce specific anti-toxin antibodies after injection. These diphtheria toxoids are used in diphtheria vaccines. Preferred diphtheria toxoids are those prepared by formaldehyde treatment. The diphtheria toxoid can be obtained by growing *C. diphtheriae* in growth medium, followed by formaldehyde treatment, ultrafiltration and precipitation. The toxoided material may then be treated by a process comprising sterile filtration and/or dialysis. The diphtheria toxoid is preferably adsorbed onto an aluminum hydroxide adjuvant.

Tetanus toxoid: *Clostridium tetani* causes tetanus. Tetanus toxin can be treated to give a protective toxoid. The toxoids are used in tetanus vaccines. Preferred tetanus toxoids are those prepared by formaldehyde treatment. The tetanus toxoid can be obtained by growing *C. tetani* in growth medium, followed by formaldehyde treatment, ultrafiltration and precipitation. The material may then be treated by a process comprising sterile filtration and/or dialysis.

Hepatitis A virus antigens: Hepatitis A virus (HAV) is one of the known agents which causes viral hepatitis. A preferred HAV component is based on inactivated virus, and inactivation can be achieved by formalin treatment.

Hepatitis B virus (HBV) is one of the known agents which causes viral hepatitis. The major component of the capsid is a protein known as HBV surface antigen or, more commonly, HBsAg, which is typically a 226-amino acid polypeptide with a molecular weight of ~24 kDa. All existing hepatitis B vaccines contain HBsAg, and when this antigen is administered to a normal vaccine it stimulates the production of anti-HBsAg antibodies which protect against HBV infection.

For vaccine manufacture, HBsAg has been made in two ways: purification of the antigen in particulate form from the plasma of chronic hepatitis B carriers or expression of the protein by recombinant DNA methods (e.g., recombinant expression in yeast cells). Unlike native HBsAg (i.e., as in the plasma-purified product), yeast-expressed HBsAg is generally non-glycosylated, and this is the most preferred form of HBsAg for use with the invention.

Conjugated *Haemophilus influenzae* type b antigens: *Haemophilus influenzae* type b (Hib) causes bacterial meningitis. Hib vaccines are typically based on the capsular saccharide antigen, the preparation of which is well documented. The Hib saccharide can be conjugated to a carrier protein in order to enhance its immunogenicity, especially in children. Typical carrier proteins are tetanus toxoid, diphtheria toxoid, CRM197, *H. influenzae* protein D, and an outer membrane protein complex from serogroup B meningococcus. The saccharide moiety of the conjugate may comprise full-length polyribosylribitol phosphate (PRP) as prepared from Hib bacteria, and/or fragments of full-length PRP. Hib conjugates may or may not be adsorbed to an aluminum salt adjuvant.

In an embodiment the immunogenic compositions of the invention further include a conjugated *N. meningitidis* serogroup Y capsular saccharide (MenY), and/or a conjugated *N. meningitidis* serogroup C capsular saccharide (MenC).

In an embodiment the immunogenic compositions of the invention further include a conjugated *N. meningitidis* serogroup A capsular saccharide (MenA), a conjugated *N. meningitidis* serogroup W135 capsular saccharide (MenW135), a conjugated *N. meningitidis* serogroup Y capsular saccharide (MenY), and/or a conjugated *N. meningitidis* serogroup C capsular saccharide (MenC).

In an embodiment the immunogenic compositions of the invention further include a conjugated *N. meningitidis* serogroup W135 capsular saccharide (MenW135), a conjugated *N. meningitidis* serogroup Y capsular saccharide (MenY), and/or a conjugated *N. meningitidis* serogroup C capsular saccharide (MenC).

4 Adjuvant(s)

In some embodiments, the immunogenic compositions disclosed herein may further comprise at least one adjuvant (e.g., one, two or three adjuvants). The term "adjuvant" refers to a compound or mixture that enhances the immune response to an antigen.

Antigens may act primarily as a delivery system, primarily as an immune modulator or have strong features of both. Suitable adjuvants include those suitable for use in mammals, including humans.

Examples of known suitable delivery-system type adjuvants that can be used in humans include, but are not limited to, alum (e.g., aluminum phosphate, aluminum sulfate or aluminum hydroxide), calcium phosphate, liposomes, oil-in-water emulsions such as MF59 (4.3% w/v squalene, 0.5% w/v polysorbate 80 (Tween 80), 0.5% w/v sorbitan trioleate (Span 85)), water-in-oil emulsions such as Montanide, and poly(D,L-lactide-co-glycolide) (PLG) microparticles or nanoparticles.

In an embodiment, the immunogenic compositions disclosed herein comprise aluminum salts (alum) as adjuvant (e.g., aluminum phosphate, aluminum sulfate or aluminum hydroxide). In a preferred embodiment, the immunogenic compositions disclosed herein comprise aluminum phosphate or aluminum hydroxide as adjuvant. In an embodiment, the immunogenic compositions disclosed herein comprise from 0.1 mg/mL to 1 mg/mL or from 0.2 mg/mL to 0.3 mg/ml of elemental aluminum in the form of aluminum phosphate. In an embodiment, the immunogenic compositions disclosed herein comprise about 0.25 mg/mL of elemental aluminum in the form of aluminum phosphate. Examples of known suitable immune modulatory type adjuvants that can be used in humans include, but are not limited to, saponin extracts from the bark of the Aquilla tree (QS21, Quil A), TLR4 agonists such as MPL (Monophosphoryl Lipid A), 3DMPL (3-O-deacylated MPL) or GLA-AQ, LT/CT mutants, cytokines such as the various interleukins (e.g., IL-2, IL-12) or GM-CSF, and the like.

Examples of known suitable immune modulatory type adjuvants with both delivery and immune modulatory features that can be used in humans include, but are not limited to ISCOMS (see, e.g., Sjölander et al. (1998) J. Leukocyte Biol. 64:713; WO 90/03184, WO 96/11711, WO 00/48630, WO 98/36772, WO 00/41720, WO 2006/134423 and WO 2007/026190) or GLA-EM which is a combination of a TLR4 agonist and an oil-in-water emulsion.

For veterinary applications including but not limited to animal experimentation, one can use Complete Freund's Adjuvant (CFA), Freund's Incomplete Adjuvant (IFA), Emulsigen, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further exemplary adjuvants to enhance effectiveness of the pneumococcal vaccines as disclosed herein include, but are not limited to: (1) oil-in-water emulsion formulations (with or without other specific immunostimulating agents such as muramyl peptides (see below) or bacterial cell wall components), such as for example (a) SAF, containing 10% Squalane, 0.4% Tween 80, 5% pluronic-blocked polymer L121, and thr-MDP either microfluidized into a submicron emulsion or vortexed to generate a larger particle size emulsion, and (b) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21, STIMULON™ (Cambridge Bioscience, Worcester, Mass.), Abisco® (Isconova, Sweden), or Iscomatrix® (Commonwealth Serum Laboratories, Australia), may be used or particles generated therefrom such as ISCOMs (immunostimulating complexes), which ISCOMS may be devoid of additional detergent (e.g., WO 00/07621); (3) Complete Freund's Adjuvant (CFA) and Incomplete Freund's Adjuvant (IFA); (4) cytokines, such as interleukins (e.g., IL-1, IL-2, IL-4, IL-5, IL-6, IL-7, IL-12 (WO 99/44636)), interferons (e.g., gamma interferon), macrophage colony stimulating factor (M-CSF), tumor necrosis factor (TNF), etc.; (5) monophosphoryl lipid A (MPL) or 3-O-deacylated MPL (3dMPL) (see, e.g., GB-2220221, EP0689454), optionally in the substantial absence of alum when used with pneumococcal saccharides (see, e.g., WO 00/56358); (6) combinations of 3dMPL with, for example, QS21 and/or oil-in-water emulsions (see, e.g., EP0835318, EP0735898, EP0761231); (7) a polyoxyethylene ether or a polyoxyethylene ester (see, e.g., WO99/52549); (8) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (9) a saponin and an immunostimulatory oligonucleotide (e.g., a CpG oligonucleotide) (WO 00/62800); (10) an immunostimulant and a particle of metal salt (see e.g., WO00/23105); (11) a saponin and an oil-in-water emulsion e.g., WO 99/11241; (12) a saponin (e.g., QS21)+3dMPL+IM2 (optionally+a sterol) e.g., WO 98/57659; (13) other substances that act as immunostimulating agents to enhance the efficacy of the composition. Muramyl peptides include N-acetyl-muramyl-L-threonyl-D-isoglutamine (thr-MDP), N–25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc.

In an embodiment of the present invention, the immunogenic compositions as disclosed herein comprise a CpG Oligonucleotide as adjuvant. A CpG oligonucleotide as used herein refers to an immunostimulatory CpG oligodeoxynucleotide (CpG ODN), and accordingly these terms are used interchangeably unless otherwise indicated. Immunostimulatory CpG oligodeoxynucleotides contain one or more immunostimulatory CpG motifs that are unmethylated cytosine-guanine dinucleotides, optionally within certain preferred base contexts. The methylation status of the CpG immunostimulatory motif generally refers to the cytosine residue in the dinucleotide. An immunostimulatory oligonucleotide containing at least one unmethylated CpG dinucleotide is an oligonucleotide which contains a 5' unmethylated cytosine linked by a phosphate bond to a 3' guanine, and which activates the immune system through binding to Toll-like receptor 9 (TLR-9). In another embodiment the immunostimulatory oligonucleotide may contain one or more methylated CpG dinucleotides, which will activate the immune system through TLR9 but not as strongly as if the CpG motif(s) was/were unmethylated. CpG immunostimulatory oligonucleotides may comprise one or more palindromes that in turn may encompass the CpG dinucleotide. CpG oligonucleotides have been described in a number of issued patents, published patent applications, and other publications, including U.S. Pat. Nos. 6,194,388; 6,207,646; 6,214,806; 6,218,371; 6,239,116; and 6,339,068.

In an embodiment of the present invention, the immunogenic compositions as disclosed herein comprise any of the CpG Oligonucleotide described at pages 3, lines 22, to page 12, line 36, of WO 2010/125480.

Different classes of CpG immunostimulatory oligonucleotides have been identified. These are referred to as A, B, C and P class, and are described in greater detail at pages 3, lines 22, to page 12, line 36, of WO 2010/125480. Methods of the invention embrace the use of these different classes of CpG immunostimulatory oligonucleotides. In an embodiment of the present invention, the immunogenic compositions as disclosed herein comprise an A class CpG oligonucleotide. In an embodiment of the present invention, the immunogenic compositions as disclosed herein comprise a B class CpG Oligonucleotide.

The B class CpG oligonucleotide sequences of the invention are those broadly described above as well as disclosed in published WO 96/02555, WO 98/18810, and in U.S. Pat. Nos. 6,194,388; 6,207,646; 6,214,806; 6,218,371; 6,239,116; and 6,339,068. Exemplary sequences include but are not limited to those disclosed in these latter applications and patents.

In an embodiment, the "B class" CpG oligonucleotide of the invention has the following nucleic acid sequence:

```
                                          (SEQ ID NO: 1)
5' TCGTCGTTTTTCGGTGCTTTT 3',
or (SEQ ID NO: 2)
5' TCGTCGTTTTTCGGTCGTTTT 3',
or (SEQ ID NO: 3)
5' TCGTCGTTTTGTCGTTTTGTCGTT 3',
or
```

```
                                                (SEQ ID NO: 4)
5' TCGTCGTTTCGTCGTTTTGTCGTT 3',
or (SEQ ID NO: 5)
5' TCGTCGTTTTGTCGTTTTTTTCGA 3'.
```

In any of these sequences, all of the linkages may be all phosphorothioate bonds. In another embodiment, in any of these sequences, one or more of the linkages may be phosphodiester, preferably between the "C" and the "G" of the CpG motif making a semi-soft CpG oligonucleotide. In any of these sequences, an ethyl-uridine or a halogen may substitute for the 5' T; examples of halogen substitutions include but are not limited to bromo-uridine or iodo-uridine substitutions.

Some non-limiting examples of B-Class oligonucleotides include:

```
                                                (SEQ ID NO: 6)
5' T*C*G*T*C*G*T*T*T*T*T*C*G*G*T*G*C*T*T*T*T 3',
or (SEQ ID NO: 7)
5' T*C*G*T*C*G*T*T*T*T*T*C*G*T*C*G*T*T*T*T 3',
or (SEQ ID NO: 8)
5' T*C*G*T*C*G*T*T*T*T*G*T*C*G*T*T*T*T*G*T*C*G*T*T 3',
or (SEQ ID NO: 9)
5' T*C*G*T*C*G*T*T*T*C*G*T*C*G*T*T*T*T*G*T*C*G*T*T 3',
or (SEQ ID NO: 10)
5' T*C*G*T*C*G*T*T*T*T*G*T*C*G*T*T*T*T*T*T*C*G*A 3'.
``` wherein "*" refers to a phosphorothioate bond.

In an embodiment of the present invention, the immunogenic compositions as disclosed herein comprise a C class CpG oligonucleotide.

In an embodiment of the present invention, the immunogenic compositions as disclosed herein comprise a P class CpG oligonucleotide.

In one embodiment the oligonucleotide includes at least one phosphorothioate linkage. In another embodiment all internucleotide linkages of the oligonucleotide are phosphorothioate linkages. In another embodiment the oligonucleotide includes at least one phosphodiester-like linkage. In another embodiment the phosphodiester-like linkage is a phosphodiester linkage. In another embodiment a lipophilic group is conjugated to the oligonucleotide. In one embodiment the lipophilic group is cholesterol.

In an embodiment, all the internucleotide linkage of the CpG oligonucleotides disclosed herein are phosphodiester bonds ("soft" oligonucleotides, as described in WO 2007/026190). In another embodiment, CpG oligonucleotides of the invention are rendered resistant to degradation (e.g., are stabilized). A "stabilized oligonucleotide" refers to an oligonucleotide that is relatively resistant to in vivo degradation (e.g., via an exo- or endo-nuclease). Nucleic acid stabilization can be accomplished via backbone modifications. Oligonucleotides having phosphorothioate linkages provide maximal activity and protect the oligonucleotide from degradation by intracellular exo- and endo-nucleases.

The immunostimulatory oligonucleotides may have a chimeric backbone, which have combinations of phosphodiester and phosphorothioate linkages. For purposes of the instant invention, a chimeric backbone refers to a partially stabilized backbone, wherein at least one internucleotide linkage is phosphodiester or phosphodiester-like, and wherein at least one other internucleotide linkage is a stabilized internucleotide linkage, wherein the at least one phosphodiester or phosphodiester-like linkage and the at least one stabilized linkage are different. When the phosphodiester linkage is preferentially located within the CpG motif such molecules are called "semi-soft" as described in WO 2007/026190.

Other modified oligonucleotides include combinations of phosphodiester, phosphorothioate, methylphosphonate, methylphosphorothioate, phosphorodithioate, and/or p-ethoxy linkages.

Mixed backbone modified ODN may be synthesized as described in WO 2007/026190. The size of the CpG oligonucleotide (i.e., the number of nucleotide residues along the length of the oligonucleotide) also may contribute to the stimulatory activity of the oligonucleotide. For facilitating uptake into cells, CpG oligonucleotide of the invention preferably have a minimum length of 6 nucleotide residues. Oligonucleotides of any size greater than 6 nucleotides (even many kb long) are capable of inducing an immune response if sufficient immunostimulatory motifs are present, because larger oligonucleotides are degraded inside cells. In certain embodiments, the CpG oligonucleotides are 6 to 100 nucleotides long, preferentially 8 to 30 nucleotides long. In important embodiments, nucleic acids and oligonucleotides of the invention are not plasmids or expression vectors.

In an embodiment, the CpG oligonucleotide disclosed herein comprise substitutions or modifications, such as in the bases and/or sugars as described at paragraphs 134 to 147 of WO 2007/026190.

In an embodiment, the CpG oligonucleotide of the present invention is chemically modified. Examples of chemical modifications are known to the skilled person and are described, for example in Uhlmann et al. (1990) Chem. Rev. 90:543; S. Agrawal, Ed., Humana Press, Totowa, USA 1993; Crooke. et al. (1996) Annu. Rev. Pharmacol. Toxicol. 36:107-129; and Hunziker et al., (1995) Mod. Synth. Methods 7:331-417. An oligonucleotide according to the invention may have one or more modifications, wherein each modification is located at a particular phosphodiester internucleoside bridge and/or at a particular β-D-ribose unit and/or at a particular natural nucleoside base position in comparison to an oligonucleotide of the same sequence which is composed of natural DNA or RNA.

In some embodiments of the invention, CpG-containing nucleic acids might be simply mixed with immunogenic carriers according to methods known to those skilled in the art (see, e.g., WO 03/024480).

In a particular embodiment of the present invention, any of the immunogenic composition disclosed herein comprises from 2 µg to 100 mg of CpG oligonucleotide, preferably from 0.1 mg to 50 mg CpG oligonucleotide, preferably from 0.2 mg to 10 mg CpG oligonucleotide, preferably from 0.3 mg to 5 mg CpG oligonucleotide, preferably from 0.3 mg to 5 mg CpG oligonucleotide, even preferably from 0.5 mg to 2 mg CpG oligonucleotide, even preferably from 0.75 mg to 1.5 mg CpG oligonucleotide. In a preferred embodiment, any of the immunogenic composition disclosed herein comprises about 1 mg CpG oligonucleotide.

5 Formulation

The immunogenic compositions of the invention may be formulated in liquid form (i.e., solutions or suspensions) or in a lyophilized form. Liquid formulations may advantageously be administered directly from their packaged form and are thus ideal for injection without the need for reconstitution in aqueous medium as otherwise required for lyophilized compositions of the invention.

Formulation of the immunogenic composition of the present invention can be accomplished using art-recognized methods. For instance, the individual pneumococcal conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

The present disclosure provides an immunogenic composition comprising any of combination of glycoconjugates disclosed herein and a pharmaceutically acceptable excipient, carrier, or diluent.

In an embodiment, the immunogenic composition of the invention is in liquid form, preferably in aqueous liquid form.

Immunogenic compositions of the disclosure may comprise one or more of a buffer, a salt, a divalent cation, a non-ionic detergent, a cryoprotectant such as a sugar, and an anti-oxidant such as a free radical scavenger or chelating agent, or any multiple combinations thereof.

In an embodiment, the immunogenic composition of the invention comprises a buffer. In an embodiment, said buffer has a pKa of about 3.5 to about 7.5. In some embodiments, the buffer is phosphate, succinate, histidine or citrate. In certain embodiments, the buffer is succinate at a final concentration of 1 mM to 10 mM. In one particular embodiment, the final concentration of the succinate buffer is about 5 mM.

In an embodiment, the immunogenic composition of the invention comprises a salt. In some embodiments, the salt is selected from the groups consisting of magnesium chloride, potassium chloride, sodium chloride and a combination thereof. In one particular embodiment, the salt is sodium chloride. In one particular embodiment, the immunogenic composition of the invention comprises sodium chloride at 150 mM.

In an embodiment, the immunogenic compositions of the invention comprise a surfactant. In an embodiment, the surfactant is selected from the group consisting of polysorbate 20 (TWEEN™ 20), polysorbate 40 (TWEEN™ 40), polysorbate 60 (TWEEN™ 60), polysorbate 65 (TWEEN™ 65), polysorbate 80 (TWEEN™ 80), polysorbate 85 (TWEEN™ 85), TRITON™ N-1 01, TRITON™ X-100, oxtoxynol 40, nonoxynol-9, triethanolamine, triethanolamine polypeptide oleate, polyoxyethylene-660 hydroxystearate (PEG-15, Solutol H 15), polyoxyethylene-35-ricinoleate (CREMOPHOR® EL), soy lecithin and a poloxamer. In one particular embodiment, the surfactant is polysorbate 80. In some said embodiment, the final concentration of polysorbate 80 in the formulation is at least 0.0001% to 10% polysorbate 80 weight to weight (w/w). In some said embodiments, the final concentration of polysorbate 80 in the formulation is at least 0.001% to 1% polysorbate 80 weight to weight (w/w). In some said embodiments, the final concentration of polysorbate 80 in the formulation is at least 0.01% to 1% polysorbate 80 weight to weight (w/w). In other embodiments, the final concentration of polysorbate 80 in the formulation is 0.01%, 0.02%, 0.03%, 0.04%, 0.05%, 0.06%, 0.07%, 0.08%, 0.09% or 0.1% polysorbate 80 (w/w). In another embodiment, the final concentration of the polysorbate 80 in the formulation is 1% polysorbate 80 (w/w).

In certain embodiments, the immunogenic composition of the invention has a pH of 5.5 to 7.5, more preferably a pH of 5.6 to 7.0, even more preferably a pH of 5.8 to 6.0. In one embodiment, the present invention provides a container filled with any of the immunogenic compositions disclosed herein. In one embodiment, the container is selected from the group consisting of a vial, a syringe, a flask, a fermentor, a bioreactor, a bag, a jar, an ampoule, a cartridge and a disposable pen. In certain embodiments, the container is siliconized.

In an embodiment, the container of the present invention is made of glass, metals (e.g., steel, stainless steel, aluminum, etc.) and/or polymers (e.g., thermoplastics, elastomers, thermoplastic-elastomers). In an embodiment, the container of the present invention is made of glass.

In one embodiment, the present invention provides a syringe filled with any of the immunogenic compositions disclosed herein. In certain embodiments, the syringe is siliconized and/or is made of glass.

A typical dose of the immunogenic composition of the invention for injection has a volume of 0.1 mL to 2 mL, more preferable 0.2 mL to 1 mL, even more preferably a volume of about 0.5 mL.

Therefore the container or syringe as defined above is filed with a volume of 0.1 mL to 2 mL, more preferably 0.2 mL to 1 mL, even more preferably a volume of about 0.5 mL of any of the immunogenic composition defined herein.

6 Ability of the Immunogenic Compositions of the Invention to Elicit Cross-Reactive Antibodies In an embodiment, the immunogenic composition of the invention is able to elicit IgG antibodies in human which are capable of binding *S. pneumoniae* serotypes 18A, 18B and/or 18F polysaccharide as determined by ELISA assay.

In the ELISA (Enzyme-linked Immunosorbent Assay) method, antibodies from the sera of vaccinated subjects are incubated with polysaccharides which have been adsorbed to a solid support. The bound antibodies are detected using enzyme-conjugated secondary detection antibodies.

In an embodiment said ELISA assay is the standardized ELISA assay as defined by the WHO in the "Training Manual For Enzyme Linked Immunosorbent Assay For The Quantitation Of *Streptococcus pneumoniae* Serotype Specific IgG (Pn PS ELISA)." (available at http://www.vaccine.uab.edu/ELISA%20protocol.pdf, accessed on Mar. 31, 2014).

The ELISA measures type specific IgG anti-*S. pneumoniae* capsular polysaccharide (PS) antibodies present in human serum. When dilutions of human sera are added to type-specific capsular PS-coated microtiter plates, antibodies specific for that capsular PS bind to the microtiter plates. The antibodies bound to the plates are detected using a goat anti-human IgG alkaline phosphatase-labeled antibody followed by a p-nitrophenyl phosphate substrate. The optical density of the colored end product is proportional to the amount of anticapsular PS antibody present in the serum.

In an embodiment, the immunogenic composition of the invention is able to elicit IgG antibodies in human which are capable of binding *S. pneumoniae* serotypes 18A polysaccharide at a concentration of at least 0.05 µg/ml, 0.1 µg/ml, 0.2 µg/ml, 0.3 µg/ml, 0.35 µg/ml, 0.4 µg/ml or 0.5 µg/ml as determined by ELISA assay.

In an embodiment, the immunogenic composition of the invention is able to elicit IgG antibodies in human which are capable of binding *S. pneumoniae* serotypes 18B polysaccharide at a concentration of at least 0.05 µg/ml, 0.1 µg/ml, 0.2 µg/ml, 0.3 µg/ml, 0.35 µg/ml, 0.4 µg/ml or 0.5 µg/ml as determined by ELISA assay.

In an embodiment, the immunogenic composition of the invention is able to elicit IgG antibodies in human which are capable of binding S. pneumoniae serotypes 18F polysaccharide at a concentration of at least 0.05 µg/ml, 0.1 µg/ml, 0.2 µg/ml, 0.3 µg/ml, 0.35 µg/ml, 0.4 µg/ml or 0.5 µg/ml as determined by ELISA assay.

In an embodiment, the immunogenic composition of the invention is able to elicit functional antibodies in humans which are capable of killing S. pneumoniae serotype 18A, 18B and/or 18F as determined by in vitro opsonophagocytic assay (OPA) (see Example 1). In an embodiment, the immunogenic composition of the invention is able to elicit functional antibodies in humans which are capable of killing S. pneumoniae serotype 18A as determined by in vitro opsonophagocytic assay (OPA). In an embodiment, the immunogenic composition of the invention is able to elicit functional antibodies in humans which are capable of killing S. pneumoniae serotype 18B as determined by in vitro opsonophagocytic assay (OPA). In an embodiment, the immunogenic composition of the invention is able to elicit functional antibodies in human which are capable of killing S. pneumoniae serotype 18F as determined by in vitro opsonophagocytic assay (OPA). In an embodiment, the immunogenic composition of the invention is able to elicit functional antibodies in humans which are capable of killing S. pneumoniae serotype 18A and 18B as determined by in vitro opsonophagocytic assay (OPA). In an embodiment, the immunogenic composition of the invention is able to elicit functional antibodies in humans which are capable of killing S. pneumoniae serotype 18A and 18F as determined by in vitro opsonophagocytic assay (OPA). In an embodiment, the immunogenic composition of the invention is able to elicit functional antibodies in humans which are capable of killing S. pneumoniae serotype 18B and 18F as determined by in vitro opsonophagocytic assay (OPA).

The pneumococcal opsonophagocytic assay (OPA), which measures killing of S. pneumoniae cells by phagocytic effector cells in the presence of functional antibody and complement, is considered to be an important surrogate for evaluating the effectiveness of pneumococcal vaccines.

In vitro opsonophagocytic assay (OPA) can be conducted by incubating together a mixture of Streptococcus pneumoniae cells, a heat inactivated human serum to be tested, differentiated HL-60 cells (phagocytes) and an exogenous complement source (e.g., baby rabbit complement). Opsonophagocytosis proceeds during incubation and bacterial cells that are coated with antibody and complement are killed upon opsonophagocytosis. Colony forming units (cfu) of surviving bacteria that escape from opsonophagocytosis are determined by plating the assay mixture. The OPA titer is defined as the reciprocal dilution that results in a 50% reduction in bacterial count over control wells without test serum. The OPA titer is interpolated from the two dilutions that encompass this 50% killing cut-off.

An endpoint titer of 1:8 or greater is considered a positive result in these killing type OPA.

In an embodiment, the immunogenic composition of the invention is able to elicit a titer of at least 1:8 against S. pneumoniae serotype 18A in at least 50% of the subjects as determined by in vitro opsonophagocytic killing assay (OPA). In an embodiment, the immunogenic composition of the invention is able to elicit a titer of at least 1:8 against S. pneumoniae serotype 18A in at least 60% 70% 80% 90% 95% 98% or at least 99% of the subjects as determined by in vitro opsonophagocytic killing assay (OPA).

In an embodiment, the immunogenic composition of the invention is able to elicit a titer of at least 1:8 against S. pneumoniae serotype 18B in at least 50% of the subjects as determined by in vitro opsonophagocytic killing assay (OPA). In an embodiment, the immunogenic composition of the invention is able to elicit a titer of at least 1:8 against S. pneumoniae serotype 18B in at least 60% 70% 80% 90% 95% 98% or at least 99% of the subjects as determined by in vitro opsonophagocytic killing assay (OPA).

In an embodiment, the immunogenic composition of the invention is able to elicit a titer of at least 1:8 against S. pneumoniae serotype 18F in at least 50% of the subjects as determined by in vitro opsonophagocytic killing assay (OPA). In an embodiment, the immunogenic composition of the invention is able to elicit a titer of at least 1:8 against S. pneumoniae serotype 18F in at least 60%, 70%, 80%, 90%, 95%, 98% or at least 99%, of the subjects as determined by in vitro opsonophagocytic killing assay (OPA).

In some embodiment, the subjects may have serotype specific OPA titers prior to pneumococcal vaccination due for example to natural exposures to S. pneumoniae (e.g., in case of adult subjects).

Therefore, comparison of OPA activity of pre- and post-immunization serum with the immunogenic composition of the invention can be conducted and compared for their response to serotypes 18A, 18B, and 18F to assess the potential increase of responders (see Example 1).

In an embodiment the immunogenic composition of the invention significantly increases the proportion of responders (i.e., individual with a serum having a titer of at least 1:8 as determined by in vitro OPA) as compared to the pre-immunized population.

Therefore in an embodiment, the immunogenic composition of the invention is able to significantly increase the proportion of responders against S. pneumoniae serotype 18A (i.e., individual with a serum having a titer of at least 1:8 as determined by in vitro OPA) as compared to the pre-immunized population.

In an embodiment, the immunogenic composition of the invention is able to significantly increase the proportion of responders against S. pneumoniae serotype 18B (i.e., individual with a serum having a titer of at least 1:8 as determined by in vitro OPA) as compared to the pre-immunized population.

In an embodiment, the immunogenic composition of the invention is able to significantly increase the proportion of responders against S. pneumoniae serotype 18F (i.e., individual with a serum having a titer of at least 1:8 as determined by in vitro OPA) as compared to the pre-immunized population.

In an embodiment, the immunogenic composition of the invention is able to significantly increase the proportion of responders against S. pneumoniae serotypes 18A and 18B (i.e., individual with a serum having a titer of at least 1:8 as determined by in vitro OPA) as compared to the pre-immunized population.

In an embodiment, the immunogenic composition of the invention is able to significantly increase the proportion of responders against S. pneumoniae serotypes 18A and 18F (i.e., individual with a serum having a titer of at least 1:8 as determined by in vitro OPA) as compared to the pre-immunized population.

In an embodiment, the immunogenic composition of the invention is able to significantly increase the proportion of responders against S. pneumoniae serotypes 18B and 18F (i.e., individual with a serum having a titer of at least 1:8 as determined by in vitro OPA) as compared to the pre-immunized population.

In an embodiment, the immunogenic composition of the invention is able to significantly increase the proportion of responders against S. pneumoniae serotypes 18A, 18B and 18F (i.e., individual with a serum having a titer of at least 1:8 as determined by in vitro OPA) as compared to the pre-immunized population.

Comparison of OPA activity of pre- and post-immunization serum with the immunogenic composition of the invention can also be done by comparing the potential increase in OPA titers.

Therefore, comparison of OPA activity of pre- and post-immunization serum with the immunogenic composition of the invention can be conducted and compared for their response to serotypes 18A, 18B, and 18F to assess the potential for increase in OPA titers (see Example 1).

In an embodiment the immunogenic compositions of the invention are able to significantly increase the OPA titer of human subjects as compared to the pre-immunized population.

Therefore in an embodiment, the immunogenic composition of the invention is able to significantly increase the OPA titers of human subjects against S. pneumoniae serotype 18A as compared to the pre-immunized population. In an embodiment, the fold-rise in OPA titer against S. pneumoniae serotype 18A is at least 1.5, 2.0, 3.0, 4.0, 5.0, 6.0, 7.0 7.5, 8.0 or 8.4.

In an embodiment, the immunogenic composition of the invention is able to significantly increase the OPA titers of human subjects against S. pneumoniae serotype 18B as compared to the pre-immunized population. In an embodiment, the fold-rise in OPA titer against S. pneumoniae serotype 18B is at least 2.0, 3.0, 4.0, 5.0, 6.0, 7.0, 8.0, 9.0, 10.0, 11.0, 12.0, 13.0, 14.0, 15.0, 15.5 or 16.0.

In an embodiment, the immunogenic composition of the invention is able to significantly increase the OPA titers of human subjects against S. pneumoniae serotype 18F as compared to the pre-immunized population. In an embodiment, the fold-rise in OPA titer against S. pneumoniae serotype 18F is at least 2.0, 3.0, 3.5, 4.0, 4.5, 5.0, 5.5, 5.7 or 5.9.

In an embodiment, the immunogenic composition of the invention is able to significantly increase the OPA titers of human subjects against S. pneumoniae serotypes 18A and 18B as compared to the pre-immunized population. In an embodiment, the fold-rise in OPA titer against S. pneumoniae serotype 18A is at least 1.5, 2.0, 3.0, 4.0, 5.0, 6.0, 7.0 7.5, 8.0 or 8.4 and the fold-rise in OPA titer against S. pneumoniae serotype 18B is at least 2.0, 3.0, 4.0, 5.0, 6.0, 7.0, 8.0, 9.0, 10.0, 11.0, 12.0, 13.0, 14.0, 15.0, 15.5 or 16.0. In an embodiment, the fold-rise in OPA titer against S. pneumoniae serotype 18A is at least 8.4 and the fold-rise in OPA titer against S. pneumoniae serotype 18B is at least 16.0.

In an embodiment, the immunogenic composition of the invention is able to significantly increase the OPA titers of human subjects against S. pneumoniae serotypes 18A and 18F as compared to the pre-immunized population. In an embodiment, the fold-rise in OPA titer against S. pneumoniae serotype 18A is at least 1.5, 2.0, 3.0, 4.0, 5.0, 6.0, 7.0 7.5, 8.0 or 8.4 and the fold-rise in OPA titer against S. pneumoniae serotype 18F is at least 2.0, 3.0, 3.5, 4.0, 4.5, 5.0, 5.5, 5.7 or 5.9. In an embodiment, the fold-rise in OPA titer against S. pneumoniae serotype 18A is at least 8.4 and the fold-rise in OPA titer against S. pneumoniae serotype 18F is at least 5.9.

In an embodiment, the immunogenic composition of the invention is able to significantly increase the OPA titers of human subjects against S. pneumoniae serotypes 18B and 18F as compared to the pre-immunized population. In an embodiment, the fold-rise in OPA titer against S. pneumoniae serotype 18B is at least 2.0, 3.0, 4.0, 5.0, 6.0, 7.0, 8.0, 9.0, 10.0, 11.0, 12.0, 13.0, 14.0, 15.0, 15.5 or 16.0 and the fold-rise in OPA titer against S. pneumoniae serotype 18F is at least 2.0, 3.0, 3.5, 4.0, 4.5, 5.0, 5.5, 5.7 or 5.9. In an embodiment, the fold-rise in OPA titer against S. pneumoniae serotype 18B is at least 16.0 and the fold-rise in OPA titer against S. pneumoniae serotype 18F is at least 5.9.

In an embodiment, the immunogenic composition of the invention is able to significantly increase the OPA titers of human subjects against S. pneumoniae serotypes 18A, 18B and 18F as compared to the pre-immunized population. In an embodiment, the fold-rise in OPA titer against S. pneumoniae serotype 18A is at least 1.5, 2.0, 3.0, 4.0, 5.0, 6.0, 7.0 7.5, 8.0 or 8.4, the fold-rise in OPA titer against S. pneumoniae serotype 18B is at least 2.0, 3.0, 4.0, 5.0, 6.0, 7.0, 8.0, 9.0, 10.0, 11.0, 12.0, 13.0, 14.0, 15.0, 15.5 or 16.0 and the fold-rise in OPA titer against S. pneumoniae serotype 18F is at least 2.0, 3.0, 3.5, 4.0, 4.5, 5.0, 5.5, 5.7 or 5.9. In an embodiment, the fold-rise in OPA titer against S. pneumoniae serotype 18A is at least 8.4, the fold-rise in OPA titer against S. pneumoniae serotype 18B is at least 16.0 and the fold-rise in OPA titer against S. pneumoniae serotype 18F is at least 5.9.

7 Uses of the Immunogenic Compositions of the Invention

In an embodiment, the immunogenic compositions disclosed herein are for use as a medicament.

The immunogenic compositions described herein may be used in various therapeutic or prophylactic methods for preventing, treating or ameliorating a bacterial infection, disease or condition in a subject. In particular, immunogenic compositions described herein may be used to prevent, treat or ameliorate a S. pneumoniae infection, disease or condition in a subject.

Thus in one aspect, the invention provides a method of preventing, treating or ameliorating an infection, disease or condition associated with S. pneumoniae in a subject, comprising administering to the subject an immunologically effective amount of an immunogenic composition of the invention.

In one aspect, the invention provides a method of preventing, treating or ameliorating an infection, disease or condition associated with S. pneumoniae serotypes 18A, 18B and 18F in a subject, comprising administering to the subject an immunologically effective amount of an immunogenic composition of the invention.

In one aspect, the invention provides a method of preventing, treating or ameliorating an infection, disease or condition associated with S. pneumoniae serotype 18A in a subject, comprising administering to the subject an immunologically effective amount of an immunogenic composition of the invention.

In one aspect, the invention provides a method of preventing, treating or ameliorating an infection, disease or condition associated with S. pneumoniae serotype 18B in a subject, comprising administering to the subject an immunologically effective amount of an immunogenic composition of the invention.

In one aspect, the invention provides a method of preventing, treating or ameliorating an infection, disease or condition associated with S. pneumoniae serotype 18F in a subject, comprising administering to the subject an immunologically effective amount of an immunogenic composition of the invention.

In one aspect, the invention provides a method of preventing, treating or ameliorating an infection, disease or condition associated with S. pneumoniae serotype 18A and 18B in a subject, comprising administering to the subject an immunologically effective amount of an immunogenic composition of the invention.

In one aspect, the invention provides a method of preventing, treating or ameliorating an infection, disease or condition associated with S. pneumoniae serotype 18A and 18F in a subject, comprising administering to the subject an immunologically effective amount of an immunogenic composition of the invention.

In one aspect, the invention provides a method of preventing, treating or ameliorating an infection, disease or condition associated with S. pneumoniae serotype 18B and 18F in a subject, comprising administering to the subject an immunologically effective amount of an immunogenic composition of the invention.

In one aspect, the invention provides a method of inducing an immune response to S. pneumoniae serotypes 18A, 18B and/or 18F in a subject, comprising administering to the subject an immunologically effective amount of an immunogenic composition of the invention.

In one aspect, the invention provides a method of inducing an immune response to S. pneumoniae serotypes 18A in a subject, comprising administering to the subject an immunologically effective amount of an immunogenic composition of the invention.

In one aspect, the invention provides a method of inducing an immune response to S. pneumoniae serotypes 18B in a subject, comprising administering to the subject an immunologically effective amount of an immunogenic composition of the invention.

In one aspect, the invention provides a method of inducing an immune response to S. pneumoniae serotypes 18F in a subject, comprising administering to the subject an immunologically effective amount of an immunogenic composition of the invention.

In one aspect, the immunogenic compositions of the present invention are for use in a method for preventing, treating or ameliorating an infection, disease or condition caused by S. pneumoniae serotypes 18A, 18B and/or 18F in a subject.

In one aspect, the immunogenic compositions of the present invention are for use in a method for preventing, treating or ameliorating an infection, disease or condition caused by S. pneumoniae serotype 18A in a subject. In one aspect, the immunogenic compositions of the present invention are for use in a method for preventing, treating or ameliorating an infection, disease or condition caused by S. pneumoniae serotype 18B in a subject. In one aspect, the immunogenic compositions of the present invention are for use in a method for preventing, treating or ameliorating an infection, disease or condition caused by S. pneumoniae serotype 18F in a subject.

In one aspect, the immunogenic compositions of the present invention are for use in a method for preventing, treating or ameliorating an infection, disease or condition caused by S. pneumoniae serotypes 18A and 18B in a subject. In one aspect, the immunogenic compositions of the present invention are for use in a method for preventing, treating or ameliorating an infection, disease or condition caused by S. pneumoniae serotype 18A and 18F in a subject. In one aspect, the immunogenic compositions of the present invention are for use in a method for preventing, treating or ameliorating an infection, disease or condition caused by S. pneumoniae serotype 18B and 18F in a subject. In an embodiment, any of the immunogenic composition disclosed herein is for use in a method of immunizing a subject against infection by S. pneumoniae serotype 18A, 18B and/or 18F.

In an embodiment, any of the immunogenic composition disclosed herein is for use in a method of immunizing a subject against infection by S. pneumoniae serotype 18A. In an embodiment, any of the immunogenic composition disclosed herein is for use in a method of immunizing a subject against infection by S. pneumoniae serotype 18B. In an embodiment, any of the immunogenic composition disclosed herein is for use in a method of immunizing a subject against infection by S. pneumoniae serotype 18F.

In an embodiment, any of the immunogenic composition disclosed herein is for use in a method of immunizing a subject against infection by S. pneumoniae serotype 18A and 18B. In an embodiment, any of the immunogenic composition disclosed herein is for use in a method of immunizing a subject against infection by S. pneumoniae serotype 18A and 18F. In an embodiment, any of the immunogenic composition disclosed herein is for use in a method of immunizing a subject against infection by S. pneumoniae serotype 18B and 18F.

In one aspect, the present invention is directed toward the use of the immunogenic composition disclosed herein for the manufacture of a medicament for preventing, treating or ameliorating an infection, disease or condition caused by S. pneumoniae serotypes 18A, 18B and/or 18F in a subject.

In one aspect, the present invention is directed toward the use of the immunogenic composition disclosed herein for the manufacture of a medicament for preventing, treating or ameliorating an infection, disease or condition caused by S. pneumoniae serotypes 18A and 18B in a subject. In one aspect, the present invention is directed toward the use of the immunogenic composition disclosed herein for the manufacture of a medicament for preventing, treating or ameliorating an infection, disease or condition caused by S. pneumoniae serotype 18A and 18F in a subject. In one aspect, the present invention is directed toward the use of the immunogenic composition disclosed herein for the manufacture of a medicament for preventing, treating or ameliorating an infection, disease or condition caused by S. pneumoniae serotype 18B and 18F in a subject.

In an embodiment, the present invention is directed toward the use of the immunogenic composition disclosed herein for the manufacture of a medicament for immunizing a subject against infection by S. pneumoniae serotype 18A, 18B and/or 18F.

In an embodiment, the present invention is directed toward the use of the immunogenic composition disclosed herein for the manufacture of a medicament for immunizing a subject against infection by S. pneumoniae serotype 18A. In an embodiment, the present invention is directed toward the use of the immunogenic composition disclosed herein for the manufacture of a medicament for immunizing a subject against infection by S. pneumoniae serotype 18B. In an embodiment, the present invention is directed toward the use of the immunogenic composition disclosed herein for the manufacture of a medicament for immunizing a subject against infection by *S. pneumoniae* serotype 18F.

In an embodiment, the present invention is directed toward the use of the immunogenic composition disclosed herein for the manufacture of a medicament for immunizing a subject against infection by *S. pneumoniae* serotype 18A and 18B. In an embodiment, the present invention is directed toward the use of the immunogenic composition disclosed herein for the manufacture of a medicament for immunizing a subject against infection by *S. pneumoniae* serotype 18A and 18F. In an embodiment, the present invention is directed toward the use of the immunogenic composition disclosed herein for the manufacture of a medicament for immunizing a subject against infection by *S. pneumoniae* serotype 18B and 18F.

In one aspect, the present invention provides a method for inducing an immune response to *S. pneumoniae* serotypes 18A, 18B and/or 18F in a subject. In one aspect, the present invention provides a method for inducing an immune response to *S. pneumoniae* serotype 18A in a subject. In one aspect, the present invention provides a method for inducing an immune response to *S. pneumoniae* serotype 18B in a subject. In one aspect, the present invention provides a method for inducing an immune response to *S. pneumoniae* serotype 18F in a subject. In an embodiment, the immunogenic compositions disclosed herein are for use as a vaccine. More particularly, the immunogenic compositions described herein may be used to prevent serotypes 18A, 18B and/or 18F *S. pneumoniae* infections in a subject. Thus in one aspect, the invention provides a method of preventing, an infection by serotypes 18A, 18B and/or 18F *S. pneumoniae* in a subject, comprising administering to the subject an immunologically effective amount of an immunogenic composition of the invention. In some such embodiments, the infection is selected from the group consisting of pneumonia, sinusitis, otitis media, acute otitis media, meningitis, bacteremia, sepsis, pleural empyema, conjunctivitis, osteomyelitis, septic arthritis, endocarditis, peritonitis, pericarditis, mastoiditis, cellulitis, soft tissue infection and brain abscess. In one aspect, the subject to be vaccinated is a mammal, such as a human, cat, sheep, pig, horse, bovine or dog.

In one aspect, the immunogenic compositions disclosed herein are for use in a method of preventing, treating or ameliorating an infection, disease or condition associated *S. pneumoniae* with serotypes 18A, 18B and/or 18F in a subject. In some such embodiments, the infection, disease or condition is selected from the group consisting of pneumonia, sinusitis, otitis media, acute otitis media, meningitis, bacteremia, sepsis, pleural empyema, conjunctivitis, osteomyelitis, septic arthritis, endocarditis, peritonitis, pericarditis, mastoiditis, cellulitis, soft tissue infection and brain abscess.

In an aspect, the immunogenic composition disclosed herein are for use in a method of preventing, an infection by serotypes 18A, 18B and/or 18F of *S. pneumoniae* in a subject. In some such embodiments, the infection is selected from the group consisting of pneumonia, sinusitis, otitis media, acute otitis media, meningitis, bacteremia, sepsis, pleural empyema, conjunctivitis, osteomyelitis, septic arthritis, endocarditis, peritonitis, pericarditis, mastoiditis, cellulitis, soft tissue infection and brain abscess. In one aspect, the subject to be vaccinated is a mammal, such as a human, cat, sheep, pig, horse, bovine or dog.

In one aspect, the present invention is directed toward the use of the immunogenic composition disclosed herein for the manufacture of a medicament for preventing, treating or ameliorating an infection, disease or condition associated *S. pneumoniae* with serotypes 18A, 18B and/or 18F in a subject. In some such embodiments, the infection, disease or condition is selected from the group consisting of pneumonia, sinusitis, otitis media, acute otitis media, meningitis, bacteremia, sepsis, pleural empyema, conjunctivitis, osteomyelitis, septic arthritis, endocarditis, peritonitis, pericarditis, mastoiditis, cellulitis, soft tissue infection and brain abscess.

In an aspect, the present invention is directed toward the use of the immunogenic composition disclosed herein for the manufacture of a medicament for preventing, an infection by serotypes 18A, 18B and/or 18F of *S. pneumoniae* in a subject. In some such embodiments, the infection is selected from the group consisting of pneumonia, sinusitis, otitis media, acute otitis media, meningitis, bacteremia, sepsis, pleural empyema, conjunctivitis, osteomyelitis, septic arthritis, endocarditis, peritonitis, pericarditis, mastoiditis, cellulitis, soft tissue infection and brain abscess. In one aspect, the subject to be vaccinated is a mammal, such as a human, cat, sheep, pig, horse, bovine or dog.

The immunogenic compositions of the present invention can be used to protect or treat a human susceptible to *S. pneumoniae* serotypes 18A, 18B and/or 18F infection, by means of administering the immunogenic compositions via a systemic or mucosal route.

In an embodiment, the immunogenic compositions disclosed herein are administered by intramuscular, intraperitoneal, intradermal or subcutaneous routes. In an embodiment, the immunogenic compositions disclosed herein are administered by intramuscular, intraperitoneal, intradermal or subcutaneous injection. In an embodiment, the immunogenic compositions disclosed herein are administered by intramuscular or subcutaneous injection.

In an embodiment, the immunogenic compositions of the present disclosure comprise at least one glycoconjugate from *S. pneumoniae* 9V (such as the glycoconjugates of paragraph 1.3 above).

8 Subject to be Treated with the Immunogenic Compositions of the Invention

As disclosed herein, the immunogenic compositions described herein may be used in various therapeutic or prophylactic methods for preventing, treating or ameliorating a bacterial infection, disease or condition in a subject.

In a preferred embodiment, said subject is a human. In a most preferred embodiment, said subject is a newborn (i.e., under three months of age), an infant (i.e., from 3 months to one year of age) or a toddler (i.e., from one year to four years of age).

In an embodiment, the immunogenic compositions disclosed herein are for use as a vaccine.

In such embodiment, the subject to be vaccinated may be less than 1 year of age. For example, the subject to be vaccinated can be about 1, about 2, about 3, about 4, about 5, about 6, about 7, about 8, about 9, about 10, about 11 or about 12 months of age. In an embodiment, the subject to be vaccinated is about 2, 4 or 6 months of age. In another embodiment, the subject to be vaccinated is less than 2 years of age. For example the subject to be vaccinated can be about 12 to about 15 months of age. In some cases, as little as one dose of the immunogenic composition according to the invention is needed, but under some circumstances, a second, third or fourth dose may be given (see section 9 below).

In an embodiment of the present invention, the subject to be vaccinated is a human adult 50 years of age or older, more preferably a human adult 55 years of age or older.

In an embodiment, the subject to be vaccinated is a human adult 65 years of age or older, 70 years of age or older, 75 years of age or older or 80 years of age or older. In an embodiment the subject to be vaccinated is an immunocompromised individual, in particular a human. An immunocompromised individual is generally defined as a person who exhibits an attenuated or reduced ability to mount a normal humoral or cellular defense to challenge by infectious agents.

In an embodiment of the present invention, the immunocompromised subject to be vaccinated suffers from a disease or condition that impairs the immune system and results in an antibody response that is insufficient to protect against or treat pneumococcal disease.

In an embodiment, said disease is a primary immunodeficiency disorder. Preferably, said primary immunodeficiency disorder is selected from the group consisting of: combined T- and B-cell immunodeficiencies, antibody deficiencies, well-defined syndromes, immune dysregulation diseases, phagocyte disorders, innate immunity deficiencies, autoinflammatory disorders, and complement deficiencies. In an embodiment, said primary immunodeficiency disorder is selected from the one disclosed on page 24, line 11, to page 25, line 19, of WO 2010/125480.

In a particular embodiment of the present invention, the immunocompromised subject to be vaccinated suffers from a disease selected from the groups consisting of: HIV-infection, acquired immunodeficiency syndrome (AIDS), cancer, chronic heart or lung disorders, congestive heart failure, diabetes mellitus, chronic liver disease, alcoholism, cirrhosis, spinal fluid leaks, cardiomyopathy, chronic bronchitis, emphysema, chronic obstructive pulmonary disease (COPD), spleen dysfunction (such as sickle cell disease), lack of spleen function (asplenia), blood malignancy, leukemia, multiple myeloma, Hodgkin's disease, lymphoma, kidney failure, nephrotic syndrome and asthma.

In an embodiment of the present invention, the immunocompromised subject to be vaccinated suffers from malnutrition.

In a particular embodiment of the present invention, the immunocompromised subject to be vaccinated is taking a drug or treatment that lowers the body's resistance to infection. In an embodiment, said drug is selected from the one disclosed on page 26, line 33, to page 26, line 4, of WO 2010/125480.

In a particular embodiment of the present invention, the immunocompromised subject to be vaccinated is a smoker.

In a particular embodiment of the present invention, the immunocompromised subject to be vaccinated has a white blood cell count (leukocyte count) below $5 \times 10^9$ cells per liter, or below $4 \times 10^9$ cells per liter, or below $3 \times 10^9$ cells per liter, or below $2 \times 10^9$ cells per liter, or below $1 \times 10^9$ cells per liter, or below $0.5 \times 10^9$ cells per liter, or below $0.3 \times 10^9$ cells per liter, or below $0.1 \times 10^9$ cells per liter.

White blood cell count (leukocyte count): The number of white blood cells (WBC) in the blood. The WBC is usually measured as part of the CBC (complete blood count). White blood cells are the infection-fighting cells in the blood and are distinct from the red (oxygen-carrying) blood cells known as erythrocytes. There are different types of white blood cells, including neutrophils (polymorphonuclear leukocytes; PMN), band cells (slightly immature neutrophils), T-type lymphocytes (T-cells), B-type lymphocytes (B-cells), monocytes, eosinophils, and basophils. All the types of white blood cells are reflected in the white blood cell count. The normal range for the white blood cell count is usually between 4,300 and 10,800 cells per cubic millimeter of blood. This can also be referred to as the leukocyte count and can be expressed in international units as $4.3-10.8 \times 10^9$ cells per liter.

In a particular embodiment of the present invention, the immunocompromised subject to be vaccinated suffers from neutropenia. In a particular embodiment of the present invention, the immunocompromised subject to be vaccinated has a neutrophil count below $2 \times 10^9$ cells per liter, or below $1 \times 10^9$ cells per liter, or below $0.5 \times 10^9$ cells per liter, or below $0.1 \times 10^9$ cells per liter, or below $0.05 \times 10^9$ cells per liter.

A low white blood cell count or "neutropenia" is a condition characterized by abnormally low levels of neutrophils in the circulating blood. Neutrophils are a specific kind of white blood cell that help prevent and fight infections. The most common reason that cancer patients experience neutropenia is as a side effect of chemotherapy. Chemotherapy-induced neutropenia increases a patient's risk of infection and disrupts cancer treatment.

In a particular embodiment of the present invention, the immunocompromised subject to be vaccinated has a CD4+ cell count below 500/mm3, or CD4+ cell count below 300/mm3, or CD4+ cell count below 200/mm3, CD4+ cell count below 100/mm3, CD4+ cell count below 75/mm3, or CD4+ cell count below 50/mm3.

CD4 cell tests are normally reported as the number of cells in mm3. Normal CD4 counts are between 500 and 1600, and CD8 counts are between 375 and 1100. CD4 counts drop dramatically in people with HIV.

In an embodiment of the invention, any of the immunocompromised subject disclosed herein is a human male or a human female.

9 Regimen

In some cases, as little as one dose of the immunogenic composition according to the invention is needed, but under some circumstances, such as conditions of greater immune deficiency, a second, third or fourth dose may be given. Following an initial vaccination, subjects can receive one or several booster immunizations adequately spaced.

In an embodiment, the schedule of vaccination of the immunogenic composition according to the invention is a single dose. In a particular embodiment, said single dose schedule is for healthy persons being at least 2 years of age.

In an embodiment, the schedule of vaccination of the immunogenic composition according to the invention is a multiple dose schedule. In a particular embodiment, said multiple dose schedule consists of a series of 2 doses separated by an interval of about 1 month to about 2 months. In a particular embodiment, said multiple dose schedule consists of a series of 2 doses separated by an interval of about 1 month, or a series of 2 doses separated by an interval of about 2 months.

In another embodiment, said multiple dose schedule consists of a series of 3 doses separated by an interval of about 1 month to about 2 months. In another embodiment, said multiple dose schedule consists of a series of 3 doses separated by an interval of about 1 month, or a series of 3 doses separated by an interval of about 2 months.

In another embodiment, said multiple dose schedule consists of a series of 3 doses separated by an interval of about 1 month to about 2 months followed by a fourth dose about 10 months to about 13 months after the first dose. In another embodiment, said multiple dose schedule consists of a series of 3 doses separated by an interval of about 1 month followed by a fourth dose about 10 months to about 13 months after the first dose, or a series of 3 doses separated by an interval of about 2 months followed by a fourth dose about 10 months to about 13 months after the first dose.

In an embodiment, the multiple dose schedule consists of at least one dose (e.g., 1, 2 or 3 doses) in the first year of age followed by at least one toddler dose.

In an embodiment, the multiple dose schedule consists of a series of 2 or 3 doses separated by an interval of about 1 month to about 2 months (for example 28-56 days between doses), starting at 2 months of age, and followed by a toddler dose at 12-18 months of age. In an embodiment, said multiple dose schedule consists of a series of 3 doses separated by an interval of about 1 to 2 months (for example 28-56 days between doses), starting at 2 months of age, and followed by a toddler dose at 12-15 months of age. In another embodiment, said multiple dose schedule consists of a series of 2 doses separated by an interval of about 2 months, starting at 2 months of age, and followed by a toddler dose at 12-18 months of age.

In an embodiment, the multiple dose schedule consists of a 4-dose series of vaccine at 2, 4, 6, and 12-15 months of age.

In an embodiment, a prime dose is given at day 0 and one or more boosts are given at intervals that range from about 2 to about 24 weeks, preferably with a dosing interval of 4-8 weeks.

In an embodiment, a prime dose is given at day 0 and a boost is given about 3 months later.

10 Kit and Process

In an embodiment, the invention is directed toward a kit comprising an immunogenic composition disclosed herein and an information leaflet.

In an embodiment said information leaflet mentions the ability of the composition to elicit functional antibodies against S. pneumoniae serotypes 18B, 18F and/or 18A.

In an embodiment said information leaflet mentions the ability of the composition to elicit functional antibodies against S. pneumoniae serotype 18A.

In an embodiment said information leaflet mentions the ability of the composition to elicit anti-capsular antibodies against S. pneumoniae serotypes 18B, 18F and/or 18A at a concentration 0.35 µg/mL in a human population.

In an embodiment said information leaflet mentions the ability of the composition to elicit anti-capsular antibodies against S. pneumoniae serotype 18A at a concentration 0.35 µg/mL in a human population.

In an embodiment said information leaflet mentions the ability of the composition to elicit OPA titers against S. pneumoniae serotypes 18B, 18F and/or 18A in a human population.

In an embodiment said information leaflet mentions the ability of the composition to elicit OPA titers against S. pneumoniae serotypes 18A in a human population.

In an embodiment, the invention is directed toward a process for producing a kit comprising an immunogenic composition and an information leaflet, said process comprising the step of:
  producing an immunogenic composition of the present disclosure and
  combining in the same kit said immunogenic composition and information leaflet, wherein said information leaflet mentions the ability of said composition to elicit functional antibodies against S. pneumoniae serotypes 18B, 18F and/or 18A.

In an embodiment, the invention is directed toward a process for producing a kit comprising an immunogenic composition and an information leaflet, said process comprising the step of:
  producing an immunogenic composition of the present disclosure and
  combining in the same kit said immunogenic composition and information leaflet, wherein said information leaflet mentions the ability of the composition to elicit anti-capsular antibodies against S. pneumoniae serotypes 18B, 18F and/or 18A at a concentration 0.35 µg/mL in a human population.

In an embodiment, the invention is directed toward a process for producing a kit comprising an immunogenic composition and an information leaflet, said process comprising the step of:
  producing an immunogenic composition of the present disclosure and
  combining in the same kit said immunogenic composition and information leaflet, wherein said information leaflet mentions the ability of the composition to elicit OPA titers against S. pneumoniae serotypes 18B, 18F and/or 18A in a human population.

In an embodiment, the invention is directed toward a process for producing a kit comprising an immunogenic composition and an information leaflet, said process comprising the step of:
  producing an immunogenic composition of the present disclosure;
  printing an information leaflet wherein said information leaflet mentions the ability of said composition to elicit functional antibodies against S. pneumoniae serotypes 18B, 18F and/or 18A;
  combining in the same kit said immunogenic composition and said information leaflet.

In an embodiment, the invention is directed toward a process for producing a kit comprising an immunogenic composition and an information leaflet, said process comprising the step of:
  producing an immunogenic composition of the present disclosure;
  printing an information leaflet wherein said information leaflet mentions the ability of the composition to elicit anti-capsular antibodies against S. pneumoniae serotypes 18B, 18F and/or 18A at a concentration ≥0.35 µg/mL in a human population;
  combining in the same kit said immunogenic composition and said information leaflet.

In an embodiment, the invention is directed toward a process for producing a kit comprising an immunogenic composition and an information leaflet, said process comprising the step of:
  producing an immunogenic composition of the present disclosure;
  printing an information leaflet wherein said information leaflet mentions the ability of the composition to elicit OPA titers against S. pneumoniae serotypes 18B, 18F and/or 18A in a human population;
  combining in the same kit said immunogenic composition and said information leaflet.

11 Methods

In an embodiment, the invention is directed toward a method comprising the step of:
- injecting to a subject an immunologically effective amount of any of the immunogenic compositions defined in the present document;
- collecting a serum sample from said subject;
- testing said serum sample for opsonophagocytic killing activity against *S. pneumoniae* serotype 18A by in vitro opsonophagocytic killing assay (OPA).

In an embodiment, the invention is directed toward a method comprising the step of:
- injecting to a subject an immunologically effective amount of any of the immunogenic compositions defined in the present document;
- collecting a serum sample from said subject;
- testing said serum sample for opsonophagocytic killing activity against *S. pneumoniae* serotype 18B by in vitro opsonophagocytic killing assay (OPA).

In an embodiment, the invention is directed toward a method comprising the step of:
- injecting to a subject an immunologically effective amount of any of the immunogenic compositions defined in the present document;
- collecting a serum sample from said subject;
- testing said serum sample for opsonophagocytic killing activity against *S. pneumoniae* serotype 18F by in vitro opsonophagocytic killing assay (OPA).

In an embodiment, the invention is directed toward a method comprising the step of:
- injecting to a subject an immunologically effective amount of any of the immunogenic compositions defined in the present document;
- collecting a serum sample from said subject;
- testing said serum sample for opsonophagocytic killing activity against *S. pneumoniae* serotypes 18A, 18B and/or 18F by in vitro opsonophagocytic killing assay (OPA).

12 The Invention Also Provides the Following Embodiments as Defined in the Following Numbered Paragraphs 1 to 103

1. An immunogenic composition comprising at least one glycoconjugate from *S. pneumoniae* serotype 18C for use in a method of immunizing a subject against infection by *S. pneumoniae* serotype 18A, 18B and/or 18F.

2. The immunogenic composition of paragraph 1, wherein said composition does not comprise capsular saccharide from *S. pneumoniae* serotype 18A.

3. The immunogenic composition of any one of paragraphs 1-2, wherein said composition does not comprise capsular saccharide from *S. pneumoniae* serotype 18B.

4. The immunogenic composition of any one of paragraphs 1-3, wherein said composition does not comprise capsular saccharide from *S. pneumoniae* serotype 18F.

5. The immunogenic composition of paragraph 1, wherein said composition does not comprise capsular saccharide from *S. pneumoniae* serotypes 18A, 18B and 18F 6. The immunogenic composition of any one of paragraphs 1-5, further comprising at least one glycoconjugate from *S. pneumoniae* serotype 4.

7. The immunogenic composition of any one of paragraphs 1-6 further comprising at least one glycoconjugate from *S. pneumoniae* serotype 6B.

8. The immunogenic composition of any one of paragraphs 1-7 further comprising at least one glycoconjugate from *S. pneumoniae* serotype 9V.

9. The immunogenic composition of any one of paragraphs 1-8 further comprising at least one glycoconjugate from *S. pneumoniae* serotype 14.

10. The immunogenic composition of any one of paragraphs 1-9 further comprising at least one glycoconjugate from *S. pneumoniae* serotype 19F.

11. The immunogenic composition of any one of paragraphs 1-10 further comprising at least one glycoconjugate from *S. pneumoniae* serotype 23F.

12. The immunogenic composition of any one of paragraphs 1-5 further comprising glycoconjugates from *S. pneumoniae* serotypes 4, 6B, 9V, 14, 19F and 23F.

13. The immunogenic composition of any one of paragraphs 1-12 further comprising at least one glycoconjugate from *S. pneumoniae* serotype 1.

14. The immunogenic composition of any one of paragraphs 1-13 further comprising at least one glycoconjugate from *S. pneumoniae* serotype 5.

15. The immunogenic composition of any one of paragraphs 1-14 further comprising at least one glycoconjugate from *S. pneumoniae* serotype 7F.

16. The immunogenic composition of any one of paragraphs 1-15 further comprising glycoconjugates from *S. pneumoniae* serotypes 1, 5 and 7F.

17. The immunogenic composition of any one of paragraphs 1-16 further comprising at least one glycoconjugate from *S. pneumoniae* serotype 6A.

18. The immunogenic composition of any one of paragraphs 1-17 further comprising at least one glycoconjugate from *S. pneumoniae* serotype 19A.

19. The immunogenic composition of any one of paragraphs 1-15 further comprising glycoconjugates from *S. pneumoniae* serotypes 6A and 19A.

20. The immunogenic composition of any one of paragraphs 1-19 further comprising at least one glycoconjugate from *S. pneumoniae* serotype 3.

21. The immunogenic composition of any one of paragraphs 1-20 further comprising at least one glycoconjugate from *S. pneumoniae* serotype 15B.

22. The immunogenic composition of any one of paragraphs 1-21 further comprising at least one glycoconjugate from *S. pneumoniae* serotype 22F.

23. The immunogenic composition of any one of paragraphs 1-22 further comprising at least one glycoconjugate from *S. pneumoniae* serotype 33F.

24. The immunogenic composition of any one of paragraphs 1-23 further comprising at least one glycoconjugate from *S. pneumoniae* serotype 12F.

25. The immunogenic composition of any one of paragraphs 1-24 further comprising at least one glycoconjugate from *S. pneumoniae* serotype 10A.

26. The immunogenic composition of any one of paragraphs 1-25 further comprising at least one glycoconjugate from *S. pneumoniae* serotype 11A.

27. The immunogenic composition of any one of paragraphs 1-26 further comprising at least one glycoconjugate from *S. pneumoniae* serotype 8.

28. The immunogenic composition of any one of paragraphs 1-20 further comprising glycoconjugates from *S. pneumoniae* serotypes 22F and 33F.

29. The immunogenic composition of any one of paragraphs 1-20 further comprising glycoconjugates from *S. pneumoniae* serotypes 15B, 22F and 33F.

30. The immunogenic composition of any one of paragraphs 1-23 further comprising glycoconjugates from *S. pneumoniae* serotypes 12F, 10A, 11A and 8.

31. The immunogenic composition of any one of paragraphs 1-30 further comprising at least one glycoconjugate from *S. pneumoniae* serotype 2.

32. The immunogenic composition of any one of paragraphs 1-31 further comprising at least one glycoconjugate from *S. pneumoniae* serotype 17F.

33. The immunogenic composition of any one of paragraphs 1-32 further comprising at least one glycoconjugate from *S. pneumoniae* serotype 20.

34. The immunogenic composition of any one of paragraphs 1-30 further comprising glycoconjugates from *S. pneumoniae* serotypes 2, 17F and 20.

35. The immunogenic composition of any one of paragraphs 1-34 further comprising at least one glycoconjugate from *S. pneumoniae* serotype 15C.

36. The immunogenic composition of any one of paragraphs 1-35 further comprising at least one glycoconjugate from *S. pneumoniae* serotype 9N.

37. The immunogenic composition of any one of paragraphs 1-36 which is a 7, 8, 9, 10, 11, 12, 13, 14, 15, 16, 17, 18, 19, 20, 21, 22, 23, 24 or 25-valent pneumococcal conjugate composition.

38. The immunogenic composition of any one of paragraphs 1-36 which is a 14, 15, 16, 17, 18, 19 or 20 valent pneumococcal conjugate composition.

39. The immunogenic composition of any one of paragraphs 1-36 which is a 16-valent pneumococcal conjugate composition.

40. The immunogenic composition of any one of paragraphs 1-36 which is a 20-valent pneumococcal conjugate composition.

41. The immunogenic composition of any one of paragraphs 1-40 wherein said glycoconjugates are individually conjugated to $CRM_{197}$.

42. The immunogenic composition of any one of paragraphs 1-40 wherein all glycoconjugates are individually conjugated to $CRM_{197}$.

43. The immunogenic composition of any one of paragraphs 1-40 wherein, the glycoconjugates from *S. pneumoniae* serotypes 1, 4, 5, 6B, 7F, 9V, 14 and/or 23F are individually conjugated to PD.

44. The immunogenic composition of any one of paragraphs 1-40 or 43 wherein the glycoconjugate from *S. pneumoniae* serotype 18C is conjugated to TT.

45. The immunogenic composition of any one of paragraphs 10-40 or 43-44 wherein the glycoconjugate from *S. pneumoniae* serotype 19F is conjugated to DT.

46. The immunogenic composition of any one of paragraphs 1-40 wherein the glycoconjugate from *S. pneumoniae* serotype 18C is conjugated to $CRM_{197}$.

47. The immunogenic composition of any one of paragraphs 1-46 wherein said glycoconjugates are prepared using CDAP chemistry.

48. The immunogenic composition of any one of paragraphs 1-46 wherein said glycoconjugates are prepared by reductive amination.

49. The immunogenic composition of any one of paragraphs 1-48 wherein said glycoconjugate from *S. pneumoniae* serotype 18C is prepared by reductive amination.

50. The immunogenic composition of any one of paragraphs 1-49 wherein said glycoconjugate from *S. pneumoniae* serotype 18C comprise a saccharide which has a degree of O-acetylation ≤10%.

51. The immunogenic composition of any one of paragraphs 1-50 wherein said glycoconjugate from *S. pneumoniae* serotype 18C has a molecular weight of between 150 kDa and 2,000 kDa.

52. The immunogenic composition of any one of paragraphs 1-51 wherein said immunogenic composition further comprise antigens from other pathogens.

53. The immunogenic composition of any one of paragraphs 1-51 wherein said immunogenic composition further comprise antigens selected from: a diphtheria toxoid (D), a tetanus toxoid (T), a pertussis antigen (P), which is typically acellular (Pa), a hepatitis B virus (HBV) surface antigen (HBsAg), a hepatitis A virus (HAV) antigen, a conjugated *Haemophilus influenzae* type b capsular saccharide (Hib), inactivated poliovirus vaccine (IPV).

54. The immunogenic composition of any one of paragraphs 1-53 wherein said immunogenic composition further comprise at least one adjuvant, most preferably any of the adjuvant disclosed herein.

55. The immunogenic composition of any one of paragraphs 1-53 wherein said immunogenic composition further comprise at least one adjuvant selected from the group consisting of aluminum phosphate, aluminum sulfate and aluminum hydroxide.

56. The immunogenic composition of any one of paragraphs 1-53 wherein said immunogenic composition comprise from 0.1 mg/mL to 1 mg/mL of elemental aluminum in the form of aluminum phosphate as adjuvant.

57. The immunogenic composition of any one of paragraphs 1-56 which is able to elicit IgG antibodies in human which are capable of binding *S. pneumoniae* serotypes 18A polysaccharide at a concentration of at least 0.35 µg/ml as determined by ELISA assay.

58. The immunogenic composition of any one of paragraphs 1-57 which is able to elicit IgG antibodies in human which are capable of binding *S. pneumoniae* serotypes 18B polysaccharide at a concentration of at least 0.35 µg/ml as determined by ELISA assay.

59. The immunogenic composition of any one of paragraphs 1-58 which is able to elicit IgG antibodies in human which are capable of binding *S. pneumoniae* serotypes 18F polysaccharide at a concentration of at least 0.35 µg/ml as determined by ELISA assay.

60. The immunogenic composition of any one of paragraphs 1-59 which is able to elicit functional antibodies in human which are capable of killing *S. pneumoniae* serotype 18A, 18B and/or 18F as determined by in vitro opsonophagocytic assay (OPA).

61. The immunogenic composition of any one of paragraphs 1-60 which is able to elicit a titer of at least 1:8 against *S. pneumoniae* serotype 18A in at least 50% of the subjects as determined by in vitro opsonophagocytic killing assay (OPA).

62. The immunogenic composition of any one of paragraphs 1-61 which is able to elicit a titer of at least 1:8 against *S. pneumoniae* serotype 18B in at least 50% of the subjects as determined by in vitro opsonophagocytic killing assay (OPA).

63. The immunogenic composition of any one of paragraphs 1-62 which is able to elicit a titer of at least 1:8 against *S. pneumoniae* serotype 18F in at least 50% of the subjects as determined by in vitro opsonophagocytic killing assay (OPA).

64. The immunogenic composition of any one of paragraphs 1-63 which is able to significantly increase the proportion of responders against *S. pneumoniae* serotype 18A as compared to the pre-immunized population.

65. The immunogenic composition of any one of paragraphs 1-64 which is able to significantly increase the proportion of responders against *S. pneumoniae* serotype 18B as compared to the pre-immunized population.

66. The immunogenic composition of any one of paragraphs 1-65 which is able to significantly increase the proportion of responders against *S. pneumoniae* serotype 18F as compared to the pre-immunized population 67. The immunogenic composition of any one of paragraphs 1-66 which is able to significantly increase the OPA titers of human subjects against *S. pneumoniae* serotype 18A as compared to the pre-immunized population.

68. The immunogenic composition of any one of paragraphs 1-67 which is able to significantly increase the OPA titers of human subjects against *S. pneumoniae* serotype 18B as compared to the pre-immunized population.

69. The immunogenic composition of any one of paragraphs 1-68 which is able to significantly increase the OPA titers of human subjects against *S. pneumoniae* serotype 18F as compared to the pre-immunized population.

70. The immunogenic composition of any one of paragraphs 1-69, for use in a method of immunizing a subject against infection by *S. pneumoniae* serotype 18A.

71. The immunogenic composition of any one of paragraphs 1-69, for use in a method of immunizing a subject against infection by *S. pneumoniae* serotype 18B.

72. The immunogenic composition of any one of paragraphs 1-69, for use in a method of immunizing a subject against infection by *S. pneumoniae* serotype 18F.

73. The immunogenic composition of any one of paragraphs 1-69, for use in a method of immunizing a subject against infection by *S. pneumoniae* serotype 18A and 18B.

74. The immunogenic composition of any one of paragraphs 1-69, for use in a method of immunizing a subject against infection by *S. pneumoniae* serotype 18A and 18F.

75. The immunogenic composition of any one of paragraphs 1-69, for use in a method of immunizing a subject against infection by *S. pneumoniae* serotype 18B and 18F.

76. The immunogenic composition of any one of paragraphs 1-69, for use in a method of immunizing a subject against infection by *S. pneumoniae* serotype 18A, 18B and 18F.

77. The immunogenic composition of any one of paragraphs 1-69 for use in a method for preventing, treating or ameliorating an infection, disease or condition caused by *S. pneumoniae* serotypes 18A, 18B and/or 18F in a subject.

78. The immunogenic composition of any one of paragraphs 1-69 for use to prevent serotypes 18A, 18B and/or 18F *S. pneumoniae* infection in a subject.

79. The immunogenic composition of any one of paragraphs 1-69 for use in a method to protect or treat a human susceptible to *S. pneumoniae* serotypes 18A, 18B and/or 18F infection, by means of administering said immunogenic compositions via a systemic or mucosal route.

80. A method of preventing, treating or ameliorating an infection, disease or condition associated with *S. pneumoniae* serotypes 18A, 18B and/or 18F in a subject, comprising administering to the subject an immunologically effective amount of an immunogenic composition of any one of paragraphs 1-69.

81. A method of preventing an infection by *S. pneumoniae* serotypes 18A, 18B and/or 18F in a subject, comprising administering to the subject an immunologically effective amount of an immunogenic composition of any one of paragraphs 1-69.

82. The immunogenic composition of any one of paragraphs 1-69, wherein said subject is a human being less than 1 year of age.

83. The immunogenic composition of any one of paragraphs 1-69, wherein said subject is a human is a human being less than 2 year of age.

84. The immunogenic composition of any one of paragraphs 1-69, wherein said subject is a human adult 50 years of age or older.

85. The immunogenic composition of any one of paragraphs 1-84 for use in a multiple dose vaccination schedule.

86. A kit comprising an immunogenic composition disclosed herein and an information leaflet.

87. A kit comprising an immunogenic composition of any one of paragraphs 1-69 and an information leaflet.

88. The kit of paragraph 86 or 87 wherein said information leaflet mentions the ability of the composition to elicit functional antibodies against *S. pneumoniae* serotypes 18B, 18F and/or 18A.

89. The kit of paragraph 86 or 87 wherein said information leaflet mentions the ability of the composition to elicit functional antibodies against *S. pneumoniae* serotype 18A.

90. The kit of paragraph 86 or 87 wherein said information leaflet mentions the ability of the composition to elicit anti-capsular antibodies against *S. pneumoniae* serotypes 18B, 18F and/or 18A at a concentration $\geq 0.35$ µg/mL in a human population.

91. The kit of paragraph 86 or 87 wherein said information leaflet mentions the ability of the composition to elicit anti-capsular antibodies against *S. pneumoniae* serotype 18A at a concentration $\geq 0.35$ µg/mL in a human population.

92. The kit of any one of paragraphs 86-91 wherein said information leaflet mentions the ability of the composition to elicit OPA titers against *S. pneumoniae* serotypes 18B, 18F and/or 18A in a human population.

93. A process for producing a kit comprising an immunogenic composition and an information leaflet, said process comprising the step of:
producing an immunogenic composition of any one of paragraphs 1-69 and
combining in the same kit said immunogenic composition and information leaflet, wherein said information leaflet mentions the ability of said composition to elicit functional antibodies against *S. pneumoniae* serotypes 18B, 18F and/or 18A.

94. A process for producing a kit comprising an immunogenic composition and an information leaflet, said process comprising the step of:
producing an immunogenic composition of any one of paragraphs 1-69 and
combining in the same kit said immunogenic composition and information leaflet, wherein said information leaflet mentions the ability of the composition to elicit anti-capsular antibodies against *S. pneumoniae* serotypes 18B, 18F and/or 18A at a concentration $\geq 0.35$ µg/mL in a human population.

95. A process for producing a kit comprising an immunogenic composition and an information leaflet, said process comprising the step of:
producing an immunogenic composition of any one of paragraphs 1-69 and
combining in the same kit said immunogenic composition and information leaflet, wherein said information leaflet mentions the ability of the composition to elicit OPA titers against *S. pneumoniae* serotypes 18B, 18F and/or 18A in a human population.

96. A process for producing a kit comprising an immunogenic composition and an information leaflet, said process comprising the step of:
producing an immunogenic composition of any one of paragraphs 1-69;
printing an information leaflet wherein said information leaflet mentions the ability of said composition to elicit functional antibodies against S. pneumoniae serotypes 18B, 18F and/or 18A;
combining in the same kit said immunogenic composition and said information leaflet.

97. A process for producing a kit comprising an immunogenic composition and an information leaflet, said process comprising the step of:
producing an immunogenic composition of any one of paragraphs 1-69;
printing an information leaflet wherein said information leaflet mentions the ability of the composition to elicit anti-capsular antibodies against S. pneumoniae serotypes 18B, 18F and/or 18A at a concentration 0.35 μg/mL in a human population;
combining in the same kit said immunogenic composition and said information leaflet.

98. A process for producing a kit comprising an immunogenic composition and an information leaflet, said process comprising the step of:
producing an immunogenic composition of any one of paragraphs 1-69;
printing an information leaflet wherein said information leaflet mentions the ability of the composition to elicit OPA titers against S. pneumoniae serotypes 18B, 18F and/or 18A in a human population;
combining in the same kit said immunogenic composition and said information leaflet.

99. A method comprising the step of:
injecting to a subject an immunologically effective amount of the immunogenic composition defined at any one of paragraphs 1-69;
collecting a serum sample from said subject;
testing said serum sample for opsonophagocytic killing activity against S. pneumoniae serotype 18A, 18B and/or 18F by in vitro opsonophagocytic killing assay (OPA).

100. A method of inducing an immune response to S. pneumoniae serotypes 18A, 18B and/or 18F in a subject, comprising administering to the subject an immunologically effective amount of an immunogenic composition of any one of paragraphs 1-69.

101. Use of an immunogenic composition of any one of paragraphs 1-69 for the manufacture of a medicament for immunizing a subject against infection by S. pneumoniae serotype 18A, 18B and/or 18F.

102. Use of an immunogenic composition of any one of paragraphs 1-69 for the manufacture of a medicament for preventing, treating or ameliorating an infection, disease or condition caused by S. pneumoniae serotypes 18A, 18B and/or 18F in a subject.

103. Use of an immunogenic composition of any one of paragraphs 1-69 for the manufacture of a medicament for preventing infection by serotypes 18A, 18B and/or 18F S. pneumoniae in a subject.

As used herein, the term "about" means within a statistically meaningful range of a value, such as a stated concentration range, time frame, molecular weight, temperature or pH. Such a range can be within an order of magnitude, typically within 20%, more typically within 10%, and even more typically within 5% or within 1% of a given value or range. Sometimes, such a range can be within the experimental error typical of standard methods used for the measurement and/or determination of a given value or range. The allowable variation encompassed by the term "about" will depend upon the particular system under study, and can be readily appreciated by one of ordinary skill in the art. Whenever a range is recited within this application, every whole number integer within the range is also contemplated as an embodiment of the disclosure.

The terms "comprising", "comprise" and "comprises" herein are intended by the inventors to be optionally substitutable with the terms "consisting of", "consist of" and "consists of", respectively, in every instance.

All references or patent applications cited within this patent specification are incorporated by reference herein.

The invention is illustrated in the accompanying examples. The examples below are carried out using standard techniques, which are well known and routine to those of skill in the art, except where otherwise described in detail. The examples are illustrative, but do not limit the invention.

EXAMPLE

Example 1. Evaluation of Cross-Reactive Opsonophagocytic Immune Responses within Serogroup 18 of Streptococcus pneumoniae Host protection against S. pneumoniae is mediated primarily through anticapsular antibodydependent opsonophagocytosis. The pneumococcal opsonophagocytic assay (OPA), which measures killing of S. pneumoniae cells by phagocytic effector cells in the presence of functional antibody and complement, is considered to be an important surrogate for evaluating the effectiveness of pneumococcal vaccines.

Materials and Methods

Sera

Two randomly selected subsets of immune sera from adults vaccinated with a 13-valent pneumococcal conjugate vaccine (13vPnC) were tested in OPA assays for the serotypes 18F, 18A, 18B and 18C. The sera were collected from U.S. clinical trials 6115A1-004 (N=59, post-vaccinated) and 6115A1-3005 (N=66, matched pre- and post-vaccination), respectively.

Study 6115A1-3005 (ClinicalTrials.gov Identifier: NCT00546572) was a phase 3, randomized, active-controlled, modified double-blind trial evaluating the safety, tolerability, and immunogenicity of PREVNAR 13® compared with a 23-valent pneumococcal polysaccharide vaccine (23vPS) in ambulatory elderly individuals aged 70 years and older who received 1 dose of 23vPS at least 5 years before study enrollment (see http://clinicaltrials.gov/ct2/show/NCT00546572, accessed on Oct. 4, 2016).

Study 6115A1-004 (ClinicalTrials.gov Identifier: NCT00427895) was a phase 3, randomized, active-controlled, modified double-blind trial evaluating the safety, tolerability, and immunogenicity of a 13-valent pneumococcal conjugate vaccine (13vPnC) compared to a 23-valent pneumococcal polysaccharide vaccine (23vPS) in adults 60 to 64 years old who are naive to 23vPS and the safety, tolerability, and immunogenicity of 13vPnC in adults 18 to 59 years old ho are naïve to 23vPS (see: http://clinicaltrials.gov/show/NCT00427895, accessed on Oct. 4, 2016).

The 13-valent pneumococcal conjugate vaccine (13vPnC) tested in these studies contained conjugates from pneumococcal serotypes 1, 3, 4, 5, 6A, 6B, 7F, 9V, 14, 18C, 19A, 19F, and 23F, individually conjugated to diphtheria cross-reacting material 197 (CRM$_{197}$) carrier protein (Prevenar 13 ®).

Microcolony Opsonophagocytic Assay (mcOPA) Procedure

Opsonophagocytic assays (OPAs) are used to measure functional antibodies in human sera against S. pneumoniae serotypes 18F, 18A, 18B and/or 18C. Test serum is set up in assay reactions that measure the ability of capsular polysaccharide specific immunoglobulin to opsonize bacteria, trigger complement deposition, thereby facilitating phagocytosis and killing of bacteria by phagocytes. The OPA titer is defined as the reciprocal dilution that results in a 50% reduction in bacterial count over control wells without test serum. The OPA titer is interpolated from the two dilutions that encompass this 50% killing cut-off.

OPA procedures were based on methods described in Hu et al., (2005) Clin Diagn Lab Immunol 12:287-295.

Microcolony Opsonophagocytic Assay quantitatively assesses functional anti-S. pneumoniae antibodies by measuring bacterial survival in microcolony OPA (mcOPA) reactions containing the test serum. Serial dilutions (2.5-fold) of heat-inactivated serum were added to the target bacteria in assay plates and incubated for 30 minutes with shaking. Baby rabbit complement (3-4 week old, 12.5% final concentration) and differentiated HL-60 cells, were then added to each well at an approximate effector to target ratio of 200:1 and incubated at 37° C. with shaking. To terminate the reaction, 80 µL of 0.9% NaCl was added to all wells, the reaction solution was mixed, and a 10-µL aliquot were transferred to the wells of Millipore, MultiScreenHTS HV filter plates containing 200 µL of water. Liquid was filtered through the plates under vacuum, and 150 µL of HySoy medium was added to each well and filtered through.

Following filtration, the filter plates were incubated overnight in a 5% CO2 incubator at 37° C. and were then fixed with Destain Solution (Bio-Rad). The plates were then stained with Coomassie Blue and destained once. Colonies were imaged and enumerated on a Cellular Technology Limited (CTL) ImmunoSpot Analyzer®. The OPA antibody titer was determined as the reciprocal of the lowest serum dilution resulting in 50% reduction in the number of bacterial colonies when compared to the bacteria-effector cell-complement control wells that did not contain serum.

Results—OPA Responses in 18F, 18A, 18B and 18C

The cross-functional response of immune sera from adults immunized with 13vPnC against serotypes 18F, 18A and 18B, was evaluated in the respective microcolony Opsonophagocytic Assays (mcOPAs), along with the homologous functional response to serotype 18C. Two randomly selected subsets of immune sera from adults vaccinated with 13vPnC were tested. The sera were collected from U.S. clinical trials 6115A1-004 (N=59, post-vaccinated) and 6115A1-3005 (N=66, matched pre- and post-vaccination), respectively (see above).

Subjects in study 6115A1-004 were previously naïve to any pneumococcal vaccination and received a single dose of 13vPnC as part of the study protocol. As shown in FIG. 1, the immune sera from study 6115A1-004 (59/59) all show positive titers not only to serotype 18C, which is the antigen in the vaccine, but also to serotypes 18F, 18A and 18B, suggesting cross-protection as measured by OPA. 100% of responders were found for all the serogroups (18C, 18F, 18A and 18B) (FIG. 1), supporting the results from 6115A1-3005 (FIG. 2).

Subjects in study 6115A1-3005 had previously received 1 dose of 23vPS at least 5 years before study enrollment and received a single dose of 13vPnC as part of the study protocol. Matched pre- and post-vaccination serum panel (N=66) from adults immunized with 13vPnC (study 6115A1-3005) was evaluated on OPA for the homologous response to serotype 18C and for cross-reactivity of anti-18C antibodies to serotypes 18F, 18A and 18B. As shown in FIG. 2, a relatively high immunity (percentage responders) to 18C (77%), 18A (73%), 18B (74%) and 18F (77%) was detected in the OPA assay likely due to their previous immunization with 23vPS, which includes unconjugated polysaccharide from serotype 18C. However, the percentage responders increased to 92% or more for all four serotypes after vaccination with 13vPnC, which only contains serotype 18C conjugate from serogroup 18. The fold-rise in titer values are shown in Table 1 and are similar between the serotypes also suggesting cross-reactivity.

TABLE 1

OPA Titer Fold-Rise Matched Pre- and Post-Vaccination, 13vPnC

| | OPA Titers | | | | | | | |
|---|---|---|---|---|---|---|---|---|
| | 18C | | 18A | | 18B | | 18F | |
| | Pre | Post | Pre | Post | Pre | Post | Pre | Post |
| GMT | 134 | 797 | 35 | 295 | 41 | 658 | 108 | 646 |
| Fold-rise | 5.9 | | 8.4 | | 16.0 | | 6.0 | |

A more comprehensive analysis of the OPA titer distribution is shown in the reverse cumulative distribution curves (RCDC) in FIGS. 3-6. The RCDCs show an increase in serotype-specific immune response post vaccination for serotypes 18C, 18F, 18A and 18B.

Conclusion

Cross-serotype functional killing of serogroup 18 strains (18F, 18A, 18B, and 18C) was observed in mcOPAs. Based on these data, the 13vPnC vaccine is likely to provide broader serotype coverage than previously anticipated by providing additional protection against serotypes 18F, 18A, and 18B in addition to the expected protection against 18C.

All publications and patent applications mentioned in the specification are indicative of the level of those skilled in the art to which this invention pertains. All publications and patent applications are hereby incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

The invention claimed is:

1. A method for preventing, treating, or ameliorating an infection, disease or condition caused by S. pneumoniae serotype 18A, 18B and/or 18F in a subject, said method comprising administering an immunogenic composition comprising:
   (a) at least one glycoconjugate from S. pneumoniae serotype 18C capsular polysaccharide, wherein said glycoconjugate is prepared by reductive amination;
   (b) glycoconjugates from S. pneumoniae serotypes 1, 3, 4, 5, 6A, 6B, 7F, 9V, 14, 19A, 19F and 23F capsular polysaccharides; and
   (c) at least one glycoconjugate from S. pneumoniae serotypes 8, 10A, 11A, 12F, 15B, 22F and 33F;
   wherein said immunogenic composition comprises 0.5 μg to 20 μg of each polysaccharide, and does not comprise capsular saccharide from S. pneumoniae serotypes 18A, 18B and 18F; and
   wherein said subject has previously received a 23-valent pneumococcal unconjugated polysaccharide vaccine.

2. The method of claim 1, wherein said immunogenic composition comprises a 14, 15, 16, 17, 18, 19, 20, 21, 22, 23, 24 or 25-valent pneumococcal conjugate composition.

3. The method of claim 1, wherein said glycoconjugates are individually conjugated to $CRM_{197}$.

4. The method of claim 1, wherein said glycoconjugate from S. pneumoniae serotype 18C comprises a saccharide which has a degree of O-acetylation ≤10%.

5. The method of claim 1, wherein said immunogenic composition further comprises at least one adjuvant.

6. The method of claim 1, wherein said immunogenic composition is able to elicit IgG antibodies in human which are capable of binding S. pneumoniae serotypes 18A, 18B and/or 18F polysaccharide at a concentration of at least 0.35 μg/ml as determined by ELISA assay.

7. The method of claim 1, wherein said immunogenic composition is able to elicit functional antibodies in human which are capable of killing S. pneumoniae serotype 18A, 18B and/or 18F as determined by in vitro opsonophagocytic assay (OPA).

8. The method of claim 1, wherein said immunogenic composition is able to elicit a titer of at least 1:8 against S. pneumoniae serotype 18A, 18B and/or 18F in at least 50% of the subjects as determined by in vitro opsonophagocytic killing assay (OPA).

9. The method of claim 1, wherein said immunogenic composition is able to increase the proportion of responders against S. pneumoniae serotype 18A, 18B and/or 18F as compared to the pre-immunized population.

10. The method of claim 1, wherein said immunogenic composition is able to increase the OPA titers of human subjects against S. pneumoniae serotype 18A, 18B and/or 18F as compared to the pre-immunized population.

* * * * *

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: "B class" CpG oligonucleotide

<400> SEQUENCE: 1
tcgtcgtttt tcggtgcttt t                                    21

<210> SEQ ID NO 2
<211> LENGTH: 21
<212> TYPE: DNA
<213> ORGANISM: Artificial Sequence
<220> FEATURE:
<223> OTHER INFORMATION: "B class" CpG oligonucleotide

<400> SEQUENCE: 2
tcgtcgtttt tcggtcgttt t                                    21

<210> SEQ ID NO 3
<211> LENGTH: 24
<212> TYPE: DNA
<213> ORGANISM: Artificial Sequence
<220> FEATURE:
<223> OTHER INFORMATION: "B class" CpG oligonucleotide

<400> SEQUENCE: 3
tcgtcgtttt gtcgttttgt cgtt                                 24

<210> SEQ ID NO 4
<211> LENGTH: 24
<212> TYPE: DNA
<213> ORGANISM: Artificial Sequence
<220> FEATURE:
<223> OTHER INFORMATION: "B class" CpG oligonucleotide

<400> SEQUENCE: 4
tcgtcgtttc gtcgttttgt cgtt                                 24

<210> SEQ ID NO 5
<211> LENGTH: 24
<212> TYPE: DNA
<213> ORGANISM: Artificial Sequence
<220> FEATURE:
<223> OTHER INFORMATION: "B class" CpG oligonucleotide

<400> SEQUENCE: 5
tcgtcgtttt gtcgtttttt tcga                                 24

<210> SEQ ID NO 6
<211> LENGTH: 21
<212> TYPE: DNA
<213> ORGANISM: Artificial Sequence
<220> FEATURE:
<223> OTHER INFORMATION: "B class" CpG oligonucleotide

<400> SEQUENCE: 6
tcgtcgtttt tcggtgcttt t                                    21

<210> SEQ ID NO 7
<211> LENGTH: 21
<212> TYPE: DNA
<213> ORGANISM: Artificial Sequence

```
<220> FEATURE:
<223> OTHER INFORMATION: "B class" CpG oligonucleotide

<400> SEQUENCE: 7
tcgtcgtttt tcggtcgttt t                                              21

<210> SEQ ID NO 8
<211> LENGTH: 24
<212> TYPE: DNA
<213> ORGANISM: Artificial Sequence
<220> FEATURE:
<223> OTHER INFORMATION: "B class" CpG oligonucleotide

<400> SEQUENCE: 8
tcgtcgtttt gtcgttttgt cgtt                                           24

<210> SEQ ID NO 9
<211> LENGTH: 24
<212> TYPE: DNA
<213> ORGANISM: Artificial Sequence
<220> FEATURE:
<223> OTHER INFORMATION: "B class" CpG oligonucleotide

<400> SEQUENCE: 9
tcgtcgtttc gtcgttttgt cgtt                                           24

<210> SEQ ID NO 10
<211> LENGTH: 24
<212> TYPE: DNA
<213> ORGANISM: Artificial Sequence
<220> FEATURE:
<223> OTHER INFORMATION: "B class" CpG oligonucleotide

<400> SEQUENCE: 10
tcgtcgtttt gtcgttttt tcga                                            24
```